(12) United States Patent
Look et al.

(10) Patent No.: US 7,525,011 B2
(45) Date of Patent: Apr. 28, 2009

(54) TRANSGENIC CANCER MODELS IN FISH

(75) Inventors: A. Thomas Look, North Reading, MA (US); David M. Langenau, Boston, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 377 days.

(21) Appl. No.: 10/659,705

(22) Filed: Sep. 11, 2003

(65) Prior Publication Data
US 2004/0117867 A1 Jun. 17, 2004

Related U.S. Application Data

(60) Provisional application No. 60/409,585, filed on Sep. 11, 2002.

(51) Int. Cl.
*A01K 67/027* (2006.01)
*G01N 33/00* (2006.01)
*A01K 43/04* (2006.01)
*A61K 31/70* (2006.01)

(52) U.S. Cl. .............................. 800/20; 514/44; 800/3
(58) Field of Classification Search .................. 800/20
See application file for complete search history.

(56) References Cited

U.S. PATENT DOCUMENTS

2003/0028909 A1 2/2003 Uckun et al.

FOREIGN PATENT DOCUMENTS

WO WO 01/40273 A2 6/2001

OTHER PUBLICATIONS

Wall, RJ, 1997, Transgenic Animal Technology, Journal of Andrology, 18:236-239.*
Houdebine, 1994, J. Biotech. vol. 34, pp. 269-287.*
Cameron, 1997, Molec. Biotech. vol. 7, pp. 253-265.*
Higashijima, S., 1997, High-frequency generation of transgenic zebrafish which reliably express GFP in whole muscles or the whole body using promoters of zebrafish origin, Dev. Biol., 192:289-299*
Niemann, 1997, Transg. Res. vol. 7, pp. 73-75.*
Wall, 1996, Transgenic livestock:progress and prospects for the future, Theriogenology, vol. 45, pp. 57-68.*
Langenau, DM et al, 2005, PNAS, 102:6068-6073.*
Sabaawy, PNAS, 2006, 103:15166-15171.*
Langenau, DM et al, 2007, Genes and Development, 21:1382-1395.*
Patton, 2005, Current Biology, 15:249-254.*
Yang, 2004, Cancer Research, 64:7256-7262.*
Aug. 3, 2004. International Search Report from PCT/US03/28223.
Rounbehler, Robert J. et al. 2001. "Myc Lacks E2F1's Ability to Suppress Skin Carcinogenesis," *Oncogene*. vol. 20, pp. 5341-5349.
Stec, David E. and Curt D. Sigmund. Nov.-Dec. 1998. "Modifiable Gene Expression in Mice: Kidney-Specific Deletion of a Target Gene via the Cre-loxP System." *Experimental Nephrology*. vol. 6, No. 6, pp. 568-575.

Winkler, Christoph and Manfred Schartl. 1997. "Gene Transfer in Laboratory Fish: Model Organisms for the Analysis of Gene Function," *Transgenic Animals*. pp. 387-395.
Langenau, David M. et al. Feb. 7, 2003. "Myc-Induced T Cell Leukemia in Transgenic Zebrafish." *Science*. vol. 299, pp. 887-890.
Ryffel, Gerhart U. et al. 2003. "Tagging Mucle Cell Lineages in Development and Tail Regeneration Using Cre Recombinase in Transgenic *Xenopus*." *Nucleic Acids Research*. vol. 31, No. 8, e44.
Golling, Gregory et al. Jun. 2002. "Insertional Mutagenesis in Zebrafish Rapidly Identifies Genes Essential for Early Vertebrate Development." *Nature Genetics*. vol. 31, pp. 135-140.
Lee, Nan Sook et al. May 2002. "Expression of Small Interfering RNAs Targeted Against HIV-1 *rev* Transcripts in Human Cells." *Nature Biotechnology*. vol. 20, pp. 500-505.
Kelly, Louise M. et al. Jan. 1, 2002. "FLT3 Internal Tandem Duplication Mutations Associated with Human Acute Myeloid Leukemias Induce Myeloproliferative Disease in a Murine Bone Marrow Transplant Model." *Blood*. vol. 99, No. 1, pp. 310-318.
Langenau, D.M. et al. 2002. "Molecular Cloning and Developmental Expression of *Tlx* (*Hox11*) Genes in Zebrafish (*Danio rerio*)." *Mechanisms of Development*. vol. 117, pp. 243-248.
Peterson, Randall T. et al. Oct. 2, 2001. "Convergence of Distinct Pathways to Heart Patterning Revealed by the Small Molecule Concentramide and the Mutation *heart-and-soul*." *Current Biology*. vol. 11, pp. 1481-1491.
Bennett, Carolyn M. et al. Aug. 1, 2001. "Myelopoiesis in the Zebrafish, *Danio rerio*." *Blood*. vol. 98, No. 3, pp. 643-651.
Huang, Haigen et al. Jul. 23, 2001. "*Pdx-1*Knockdown Reduces Insulin Promoter Activity in Zebrafish." *Genesis*. vol. 30, pp. 134-136.
Yamamoto, Yukiya et al. Apr. 15, 2001. "Activating Mutation of D835 Within the Activation Loop of FLT3 in Human Hematologic Malignancies." *Blood*. vol. 97, No. 8, pp. 2434-2439.
Jessen, Jason R. et al. Apr. 9, 2001. "Concurrent Expression of Recombination Activating Genes 1 and 2 in Zebrafish Olfactory Sensory Neurons." *Genesis*. vol. 29, pp. 156-162.

(Continued)

*Primary Examiner*—Valarie Bertoglio
(74) *Attorney, Agent, or Firm*—Wilmer Cutler Pickering Hale and Dorr LLP

(57) ABSTRACT

The present invention provides transgenic fish whose genome has stably-integrated therein an oncogene operably linked to a promoter. Methods of making the transgenic fish and methods for their use are also provided. In one embodiment, the transgenic fish may advantageously be utilized in methods of screening for drugs or agents that modulate oncogene-mediated neoplastic or hyperplasic transformation, or that modulate sensitivity to chemotherapy or radiation therapy. In another embodiment, the transgenic fish may be used methods of identifying mutations that modulate oncogene-mediated neoplastic or hyperplastic transformation, or that modulate sensitivity to chemotherapy or radiation therapy.

14 Claims, 24 Drawing Sheets

OTHER PUBLICATIONS

Hsu, Karl et al. 2001. "Zebrafish Myelopoiesis and Blood Cell Development." *Current Opinion in Hematology.* vol. 81, pp. 245-251.

Werdien, Dagmar et al. 2001. "FLP and Cre Recombinase Function in *Xenopus* Embryos." *Nucleic Acids Research.* vol. 29, No. 11, e53.

Yin, Xiao-ying et al. 2001. "Dynamic in vivo Interactions Among Myc Network Members." *Oncogene.* vol. 20, pp. 4650-4664.

Peterson, Randall T. et al. Nov. 21, 2000. "Small Molecule Developmental Screens Reveal the Logic and Timing of Vertebrate Development." *PNAS.* vol. 97, No. 24, pp. 12965-12969.

Haire, Robert N. et al. Aug. 8, 2000. "Characterization of Three Isotypes of Immunoglobulin Light Chains and T-cell Antigen Receptor $\alpha$ in Zebrafish." *Immunogenetics.* vol. 51, pp. 915-923.

Lever, Andrew ML. 2000. "Lentiviral Vectors: Progress and Potential." *Current Opinion in Molecular Therapeutics.* vol. 2, No. 5, pp. 488-496.

Motolke, Toshiyuki et al. 2000. "Universal GFP Reporter for the Study of Vascular Development." *Genesis.* vol. 28, pp. 75-81.

Jessen, Jason R. et al. Sep. 1999. "Artificial Chromosome Transgenesis Reveals Long-Distance Negative Regulation of *rag1* in Zebrafish." *Nature Genetics.* vol. 23, pp. 15-16.

Herbomel, Philippe et al. Aug. 5, 1999. "Ontogeny and Behaviour of Early Macrophages in the Zebrafish Embryo." *Development.* vol. 126, pp. 3735-3745.

Chervinsky, David S. et al. Jul. 1999. "Disordered T-Cell Development and T-Cell Malignancies in SCL LMO1 Double-Transgenic Mice: Parallels with E2A-Deficient Mice." *Molecular and Cellular Biology.* vol. 19, No. 7, pp. 5025-5035.

Yang, Hui et al. 1999. "An Optimized Method for In Situ Hybridization with Signal Amplification That Allows the Detection of Rare mRNAs." *The Journal of Histochemistry & Cytochemistry.* vol. 47, No. 4, pp. 431-445.

Look, A. Thomas. 1998. "Genes Altered by Chromosomal Translocations in Leukemias and Lymphomas." *The Genetic Basis of Human Cancer.* pp. 109-141. New York, NY: McGraw Hill.

Yuan, Jeffrey et al. 1998. "The *C. elegans* MDL-1 and MXL-1 Proteins Can Functionally Substitute for Vertebrate MAD and MAX." *Oncogene.* vol. 17, pp. 1109-1118.

He, Li-Zhen et al. May 1997. "Acute Leukemia with Promyelocytic Features in PML/RAR$\alpha$ Transgenic Mice." *Proc. Natl. Acad. Sci. USA.* vol. 94, pp. 5302-5307.

Schreiber-Agus, Nicole et al. Feb. 1997. "*Drosophila* Myc is Oncogenic in Mammalian Cells and Plays a Role in the *diminutive* Phenotype." *Proc. Natl. Acad. Sci. USA.* vol. 94, pp. 1235-1240.

Grisolano, Jay L. et al. Jan. 15, 1997. "Altered Myeloid Development and Acute Leukemia in Transgenic Mice Expressing PML-RAR$\alpha$ Under Control of Cathepsin G Regulatory Sequences." *Blood.* vol. 89, No. 2, pp. 376-387.

Altschul, Stephen F. et al. 1997. "Gapped BLAST and PSI-BLAST: A New Generation of Protein Database Search Programs." *Nucleic Acids Research.* vol. 25, No. 17, pp. 3389-3402.

Aplan, Peter D. et al. 1997. "An *scl* Gene Product Lacking the Transactivation Domain Induces Bony Abnormalities and Cooperates with LMO1 to Generate T-cell Malignancies in Transgenic Mice." *The EMBO Journal.* vol. 16, No. 9, pp. 2408-2419.

Martin, CS et al. 1997. "Continuous Sensitive Detection of $\beta$-Galactosidase with a Novel Chemiluminescent 1,2-Dioxetane." *Bioluminescence and Chemiluminscence: Molecular Reporting with Photons.* pp. 525-528. John Wiley & Sons.

Condorelli, G. L. et al. Nov. 15, 1996. "T-Cell directed *TAL-1* Expression Induces T-Cell Malignancies in Transgenic Mice." *Cancer Research.* vol. 56, pp. 5113-5119.

Druker, Brian J. et al. May 1996. "Effects of a Selective Inhibitor of the Abl Tyrosine Kinase on the Growth of Bcr-Abl Positive Cells." *Nature Medicine.* vol. 2, No. 5, pp. 561-566.

Chen, Thomas T. et al. 1996. "Transgenic Fish and its Application in Basic and Applied Research." *Biotechnology Annual Review.* vol. 2, pp. 205-236.

Kelliher, Michelle A. et al. 1996. "Tal-1 Induces T Cell Acute Lymphoblastic Leukemia Accelerated by Casein Kinase II$\alpha$." *The EMBO Journal.* vol. 15, No. 19, pp. 5160-5166.

Larson, R.C. et al. 1996. "Protein Dimerization Between Lmo2 (Rbtn2) and Tal1 Alters Thymocyte Development and Potentiates T Cell Tumorigenesis in Transgenic Mice." *The EMBO Journal.* vol. 15, No. 5, pp. 1021-1027.

Laneuville, Pierre et al. Mar. 1, 1994. "*bcr/abl* Expression in 32D cl3(G) Cells Inhibits Apoptosis Induced by Protein Tyrosine Kinase Inhibitors." *Cancer Research.* vol. 54, pp. 1360-1366.

Zabner, Joseph et al. Jan. 1994. "Safety and Efficacy of Repetitive Adenovirus-Mediated Transfer of CFTR cDNA to Airway Epithelia of Primates and Cotton Rats." *Nature Genetics.* vol. 6, pp. 75-83.

Bronstein, I. et al. 1994. "Chemiluminescent Reporter Gene Assays for $\beta$-Galactosidase, $\beta$-Glucuronidase and Secreted Alkaline Phosphatase." *Bioluminescence and Chemiluminscence: Fundamentals and Applied Aspects.* pp. 20-23. John Wiley & Sons.

Carlesso, Nadia et al. 1994. "Use of a Temperature-Sensitive Mutant to Define the Biological Effects of the $p210^{BCR-ABL}$Tryosine Kinase on Proliferation of a Factor-Dependent Murine Myeloid Cell Line." *Oncogene.* vol. 9, pp. 149-156.

Flotte, Terence R. et al. Nov. 1993. "Stable in vivo Expression of the Cystic Fibrosis Transmembrane Conductance Regulator with an Adeno-Associated Virus Vector." *Proc. Natl. Acad. Sci. USA.* vol. 90, pp. 10613-10617.

Burns, Jane C. et al. Sep. 1993. "Vesicular Stomatitis Virus G Glycoprotein Pseudotyped Retroviral Vectors: Concentration to Very High Titer and Efficient Gene Transfer into Mammalian and Nonmammalian Cells." *Proc. Natl. Acad. Sci. USA.* vol. 90, pp. 8033-8037.

Karlin, Samuel et al. Jun. 1993. "Applications and Statistics for Multiple High-Scoring Segments in Molecular Sequences." *Proc. Natl. Acad. Sci. USA.* vol. 90, pp. 5873-5877.

Schreiber-Agus, Nicole et al. May 1993. "Zebra Fish *myc* Family and *max* Genes: Differential Expression and Oncogenic Activity Throughout Vertebrate Evolution." *Molecular and Cellular Biology.* vol. 13, No. 5, pp. 2765-2775.

Evans, Caroline A. et al. Apr. 15, 1993. "Activation of the Abelson Tyrosine Kinase Activity Is Associated with Suppression of Apoptosis in Hemopoietic Cells." *Cancer Research.* vol. 53, pp. 1735-1738.

Davidson, Beverly L. et al. Mar. 1993. "A Model System for in vivo Gene Transfer into the Central Nervous System Using an Adenoviral Vector." *Nature Genetics.* vol. 3, pp. 219-223.

Erzurum, Serpil C. et al. 1993. "Protection of Human Endothelial Cells from Oxidant Injury by Adenovirus-Mediated Transfer of the Human Catalase cDNA." *Nucleic Acids Research.* vol. 21, No. 7, pp. 1607-1612.

Andersen, Julue K. et al. 1993. "Herpersvirus-Mediated Gene Delivery into the Rat Brain: Specificity and Enfficiency of the Neuron-Specific Enolase Promoter." *Cellular and Molecular Neurobiology.* vol. 13, No. 5, pp. 503-515.

Chen, Thomas T. et al. 1993. "Expression and Inheritance of RSVLTR-rtGH1 Complementary DNA in the Transgenic Common Carp, *Cyprinus Carpio.*" *Molecular Marine Biology and Biotechnology.* vol. 2, No. 2, pp. 88-95.

Miller, A. Dusty et al. 1993. "Use of Retroviral Vectors for Gene Transfer and Expression." *Methods in Enzymology.* vol. 217, pp. 581-599.

Lu, Jenn-Kan et al. 1992. "Integration, Expression, and Germ-Line Transmission of Foreign Growth Hormone Genes in Medaka (*Oryzias latipes*)." *Molecular Marine Biology and Biotechnology.* vol. 1, Nos. 4-5, pp. 366-375.

Hruby, Dennis E. et al. 1992. "Use of Fluorescent Chloramphenicol Derivative as a Substrate for Chloramphenicol Acetyltransferase Assays." *Methods in Enzymology.* vol. 216, pp. 369-376.

Powers, Dennis A. et al. 1992. "Electroporation: A Method for Transferring Genes into the Gametes of Zebrafish (*Brachydanio rerio*), Channel Catfish (*Ictalurus punctatus*), and Common Carp (*Cyprinus carpio*)." *Molecular Marine Biology and Biotechnology.* vol. 1, Nos. 4-5, pp. 301-308.

Culp, Patricia et al. Sep. 1991. "High-Frequency Germ-Line Transmission of Plasmid DNA Sequences Injected into Fertilized Zebrafish Eggs." *Proc. Natl. Acad. Sci. USA.* vol. 88, pp. 7953-7957.

Jain, Vinay K. et al. 1991. "A Chemiluminescent Assay for Quantitation of $\beta$-Galactosidase in the Femtogram Range: Application to Quantitation of β-Galactosidase in *lacZ*-Transfected Cells." *Analytical Biochemistry*. vol. 199, pp. 119-124.

Strasser, Andreas et al. Nov. 22, 1990. "Novel Primitive Lymphoid Tumours Induced in Transgenic Mice by Cooperation Between *myc* and *bcl-2*." *Nature*. vol. 348, pp. 331-333.

Chen, Thomas T. and Dennis A. Powers. Aug. 1990. "Transgenic Fish." *Tibtech*. vol. 8, pp. 209-215.

Altschul, Stephen F. et al. 1990. "Basic Local Alighment Search Tool." *J. Mol. Biol*. vol. 215, pp. 403-410.

Karlin, Samuel and Stephen F. Altschul. Mar. 1990. "Methods for Assessing the Statistical Significance of Molecular Sequence Features by Using General Scoring Schemes." *Proc. Natl. Acad. Sci. USA*. vol. 87, pp. 2264-2268.

Wilcox, Josiah N. and Rik Derynck. Aug. 1988. "Developmental Expression of Transforming Growth Factors Alpha and Beta in Mouse Fetus." *Molecular and Cellular Biology*. vol. 8, No. 8, pp. 3415-3422.

Wilcox, Josiah N. and Rik Derynck. Jun. 1988. "Localization of Cells Synthesizing Transforming Growth Factor-Alpha mRNA in the Mouse Brain." *The Journal of Neuroscience*. vol. 8, No. 6, pp. 1901-1904.

Nguyen, Van Trung et al. 1988. "Firefly Luciferase Luminescence Assays Using Scintillation Counters for Quantitation in Transfected Mammalian Cells." *Analytical Biochemistry*. vol. 171, pp. 404-408.

Miner, Jeffery N. et al. Jan. 1988. "Molecular Dissection of *cis*-Acting Regulatory Elements from 5'-Proximal Regions of a Vaccinia Virus Late Gene Cluster." *Journal of Virology*. vol. 62, No. 1, pp. 297-304.

Cullen, Bryan R. 1987. "Use of Eukaryotic Expression Technology in the Functional Analysis of Cloned Genes." *Methods in Enzymology*. vol. 152, pp. 684-704.

Rosenthal, A. et al. 1987. "Primary Structure and mRNA Localization of Protein F1, a Growth-Related Protein Kinase C Substrate Associated with Synaptic Plasticity." *The EMBO Journal*. vol. 6, No. 12, pp. 3641-3646.

Sleigh, Merilyn J. 1986. "A Nonchromatographic Assay for Expression of the Chloramphenicol Acetyltransferase Gene in Eucaryotic Cells." *Analyticalal Biochemistry*. vol. 156, pp. 251-256.

Wilcox, Josiah N. et al. 1986. "In Situ cDNA:mRNA Hybridization: Development of a Technique to Measure mRNA Levels in Individual Cells." *Methods in Enzymology*. vol. 124, pp. 510-533.

Melton, D.A. et al. 1984. "Efficient in vitro Synthesis of Biologically Active RNA and RNA Hybridization Probes from Plasmids Containing a Bacteriophage SP6 Promoter." *Nucleic Acids Research*. vol. 12, No. 18, pp. 7035-7056.

Gorman, Cornelia M. et al. Sep. 1982. "Recombinant Genomes Which Express Chloramphenicol Acetyltransferase in Mammalian Cells." *Molecular and Cellular Biology*. vol. 2, No. 9, pp. 1044-1051.

* cited by examiner

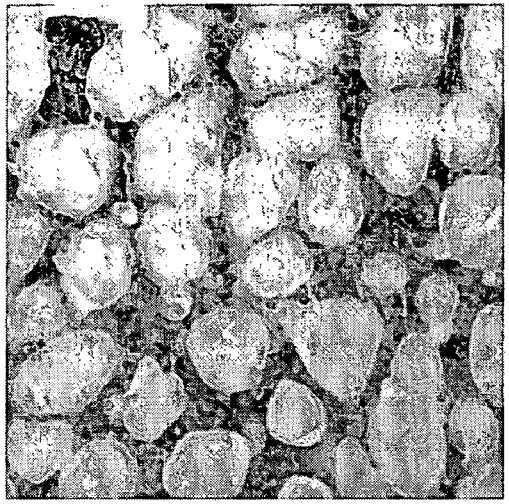 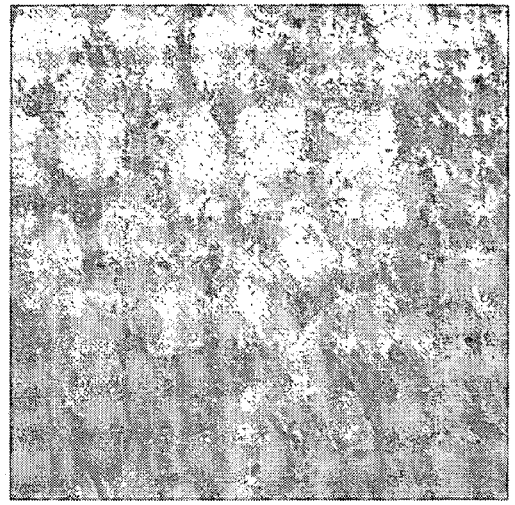
FIG. 2A  FIG. 2B
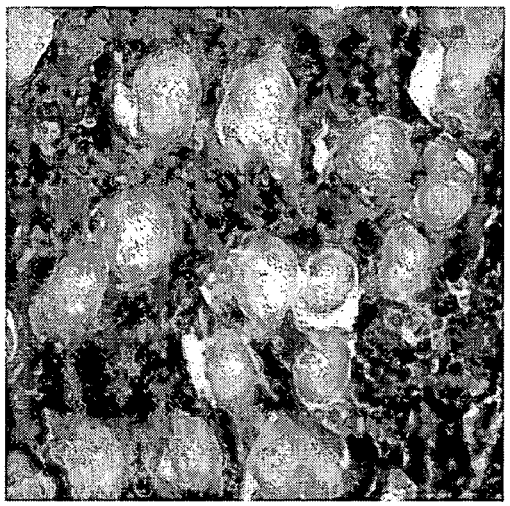 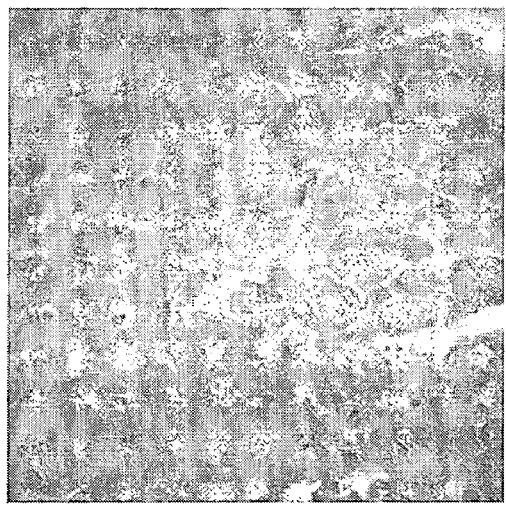
FIG. 2C  FIG. 2D ated adult brain tumors, spreading so rapidly that patients seldom survive more than 9-12 months. Despite progress in surgical, radiation and chemotherapy technologies, there has been little improvement in the outcome of patients with astrocytoma over the last twenty years. Clearly, novel approaches are needed to better understand the biological basis of this disease before effective therapies can be developed.

SEQUENCE LISTING

```
<160> NUMBER OF SEQ ID NOS: 8

<210> SEQ ID NO 1
<211> LENGTH: 228
<212> TYPE: PRT
<213> ORGANISM: Artificial Sequence
<220> FEATURE:
<223> OTHER INFORMATION: BCL2 proteins

<400> SEQUENCE: 1

Met Ala Asn Glu Ile Ser Tyr Asp Asn Arg Asn Ile Val Glu Lys Tyr
1               5                   10                  15

Leu Lys His Lys Leu Ser Lys Arg Gly Tyr Val Trp Lys Cys Gln Ser
            20                  25                  30

Ser Ala Glu Glu Asp Asp Thr Phe Asn Lys Ala Val Glu Glu Ser Ser
        35                  40                  45

Pro Asn Ser Asp Arg Arg Leu Gln Ala Pro Ser Ala Gly Gly Gly Asn
    50                  55                  60

Asn Ser Glu Cys Leu Ile Ala Arg Val Thr Arg Ser Asp Pro His Leu
65                  70                  75                  80
```

```
Arg Leu Tyr Arg Val Leu Arg Asp Ala Gly Asp Glu Ile Glu Arg Ile
                85                  90                  95

Tyr Gln Arg Glu Phe Glu Met Ser Gln Gln Met Val Phe Asn Pro
                100                 105                 110

Asn Ser Ala Gln Arg Ser Pro Leu Thr Val Ala Glu Glu Leu Phe Arg
                115                 120                 125

Asp Gly Val Asn Trp Gly Arg Ile Ile Ala Phe Phe Glu Phe Gly Gly
    130                 135                 140

Thr Met Cys Val Glu Ser Val Asn Arg Glu Met Ala Ser Gln Val Asp
145                 150                 155                 160

Asn Ile Ala His Trp Met Thr Asp Tyr Leu Asn Gly Pro Leu Glu Asn
                165                 170                 175

Trp Ile Glu Glu Asn Gly Gly Trp Asp Ala Phe Val Glu Met Tyr Gly
                180                 185                 190

Gln Gln Arg Asp Ser Val Phe His Pro Phe Ser Tyr Leu Thr Lys Val
                195                 200                 205

Leu Gly Leu Ala Ala Leu Gly Leu Ala Gly Val Thr Ile Gly Ala Phe
    210                 215                 220

Phe Ala Gln Lys
225

<210> SEQ ID NO 2
<211> LENGTH: 228
<212> TYPE: PRT
<213> ORGANISM: Artificial Sequence
<220> FEATURE:
<223> OTHER INFORMATION: BCL2 proteins

<400> SEQUENCE: 2

Leu Asn Pro Lys Lys Glu Asn Asn Gly Val Lys Asn Gly Asp Arg
  1               5                   10                  15

Glu Lys Gln His Glu Thr Gly Asn Thr Ile Phe Arg Gly Ser Pro Asp
                20                  25                  30

Lys Tyr Leu Thr Glu Gln Gly Trp Met Ala Gln Ser Asp Leu Gly Ser
                35                  40                  45

Arg Ala Leu Val Glu Asp Leu Val Arg Tyr Lys Leu Cys Gln Arg Ser
    50                  55                  60

Leu Val Pro Glu Pro Ser Gly Ala Ala Ser Cys Ala Leu His Ser Ala
65                  70                  75                  80

Met Arg Ala Ala Gly Asp Glu Phe Glu Glu Arg Pro Arg Gln Ala Phe
                85                  90                  95

Ser Glu Ile Ser Thr Gln Ile His Val Thr Pro Gly Thr Ala Tyr Ala
                100                 105                 110

Arg Phe Ala Glu Val Ala Gly Ser Leu Phe Gln Gly Gly Val Asn Trp
                115                 120                 125

Gly Arg Ile Val Ala Phe Phe Val Phe Gly Ala Ala Leu Cys Ala Glu
    130                 135                 140

Ser Val Asn Lys Glu Met Ser Pro Leu Leu Pro Arg Ile Gln Asp Trp
145                 150                 155                 160

Met Val Thr Tyr Leu Glu Thr Asn Leu Asp Arg Trp Ile Gln Ser Asn
                165                 170                 175

Gly Gly Trp Asn Gly Phe Leu Thr Leu Tyr Gly Asp Gly Ala Ile Glu
                180                 185                 190

Glu Ala Arg Arg Gln Arg Glu Gly Asn Trp Ala Ser Leu Lys Thr Val
                195                 200                 205
```

```
Leu Thr Gly Ala Val Ala Leu Gly Ala Leu Met Thr Val Gly Ala Leu
    210                 215                 220

Phe Ala Ser Lys
225

<210> SEQ ID NO 3
<211> LENGTH: 233
<212> TYPE: PRT
<213> ORGANISM: Artificial Sequence
<220> FEATURE:
<223> OTHER INFORMATION: BCL2 proteins

<400> SEQUENCE: 3

Met Ala His Pro Gly Arg Arg Gly Tyr Asp Asn Arg Glu Ile Val Leu
1               5                   10                  15

Lys Tyr Ile His Tyr Lys Leu Ser Gln Arg Gly Tyr Asp Trp Ala Ala
            20                  25                  30

Gly Glu Asp Arg Pro Pro Val Pro Ala Pro Ala Ala Ala
        35                  40                  45

Pro Ala Ala Val Ala Ala Gly Ala Ser Ser His His Arg Pro Glu
    50                  55                  60

Pro Pro Gly Ser Ala Ala Ala Ser Glu Val Pro Ala Glu Gly Leu
65                  70                  75                  80

Arg Pro Ala Pro Pro Gly Val His Leu Ala Leu Arg Gln Ala Gly Asp
                85                  90                  95

Glu Phe Ser Arg Arg Tyr Gln Arg Asp Phe Ala Gln Met Ser Gly Gln
            100                 105                 110

Leu His Leu Thr Pro Phe Thr Ala His Gly Arg Phe Val Ala Val Val
        115                 120                 125

Glu Glu Leu Phe Arg Asp Gly Val Asn Trp Gly Arg Ile Val Ala Phe
    130                 135                 140

Phe Glu Arg Gly Gly Val Met Cys Val Glu Ser Val Asn Arg Glu Met
145                 150                 155                 160

Ser Pro Leu Val Asp Asn Ile Ala Thr Trp Met Thr Glu Tyr Leu Asn
                165                 170                 175

Arg His Leu His Asn Trp Ile Gln Asp Asn Gly Gly Trp Asp Ala Phe
            180                 185                 190

Val Glu Leu Tyr Gly Asn Ser Met Arg Pro Leu Phe Asp Phe Ser Trp
        195                 200                 205

Ile Ser Leu Lys Thr Ile Leu Ser Leu Val Leu Val Gly Ala Cys Ile
    210                 215                 220

Thr Leu Gly Ala Tyr Leu Gly His Lys
225                 230

<210> SEQ ID NO 4
<211> LENGTH: 239
<212> TYPE: PRT
<213> ORGANISM: Artificial Sequence
<220> FEATURE:
<223> OTHER INFORMATION: BCL2 proteins

<400> SEQUENCE: 4

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45
```

```
Phe Ser Ser Gln Pro Gly His Thr Pro His Thr Ala Ala Ser Arg Asp
 50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                 85                  90                  95

Leu Arg Gln Ala Gly Asp Asp Phe Ser Arg Arg Tyr Arg Arg Asp Phe
                100                 105                 110

Ala Glu Met Ser Arg Gln Leu His Leu Thr Pro Phe Thr Ala Arg Gly
            115                 120                 125

Arg Pro Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
            210                 215                 220

Leu Val Gly Ala Cys Ile Thr Leu Gly Ala Tyr Leu Gly His Lys
225                 230                 235

<210> SEQ ID NO 5
<211> LENGTH: 237
<212> TYPE: PRT
<213> ORGANISM: Artificial Sequence
<220> FEATURE:
<223> OTHER INFORMATION: BCL2 proteins

<400> SEQUENCE: 5

Met Ser Tyr Tyr Asn Arg Glu Leu Val Val Phe Phe Ile Lys Tyr Lys
 1               5                  10                  15

Leu Ser Gln Arg Asn Tyr Pro Cys Asn His Ile Gly Leu Thr Glu Asp
                20                  25                  30

Thr Asn Arg Thr Asp Gly Ala Glu Glu Asn Gly Glu Gly Ala Ala Gly
             35                  40                  45

Ala Thr Thr Leu Val Asn Gly Thr Met Asn Arg Thr Asn Ala Ser Ser
 50                  55                  60

Thr Gly Thr Pro Pro Gln Ser Pro Ala Ser Ser Pro Gln Arg Gln Thr
 65                  70                  75                  80

Asn Gly Ser Gly Gly Leu Asp Ala Val Lys Glu Ala Leu Arg Asp Ser
                 85                  90                  95

Ala Asn Glu Phe Glu Leu Arg Tyr Ser Arg Ala Phe Asn Asp Leu Ser
                100                 105                 110

Gln Leu His Ile Thr Pro Ala Thr Ala Tyr Gln Ser Phe Glu Ser Val
            115                 120                 125

Met Asp Glu Val Phe Arg Asp Gly Val Asn Trp Gly Arg Ile Val Gly
130                 135                 140

Leu Phe Ala Phe Gly Gly Ala Leu Cys Val Glu Cys Val Glu Lys Glu
145                 150                 155                 160

Met Ser Pro Leu Val Gly Arg Ile Ala Glu Trp Met Thr Val Tyr Leu
                165                 170                 175
```

```
Asp Asn His Ile Gln Pro Trp Ile Gln Ser Gln Gly Gly Trp Glu Arg
            180                 185                 190
Phe Ala Glu Ile Pro Gly Lys Asp Ala Ala Glu Ser Arg Lys Ser
        195                 200                 205
Gln Glu Ser Pro Lys Lys Trp Leu Phe Ala Gly Met Thr Leu Leu Thr
    210                 215                 220
Gly Val Val Gly Gly Leu Ile Ala Gln Lys Arg Leu
225                 230                 235

<210> SEQ ID NO 6
<211> LENGTH: 204
<212> TYPE: PRT
<213> ORGANISM: Artificial Sequence
<220> FEATURE:
<223> OTHER INFORMATION: BCL2 proteins

<400> SEQUENCE: 6

Met Glu Gly Ser Ser Arg Asp Leu Val Glu Lys Phe Val Ser Lys Lys
 1               5                  10                  15
Leu Ser Gln Asn Glu Ala Cys Arg Lys Phe Ser Asn Asn Pro Gln Pro
                20                  25                  30
Asn Ala Ile Ser Asn Gly Thr Ser Thr Ser Glu Arg Pro Gly Glu Gly
            35                  40                  45
Ala Thr Gln Gly Ile Val Glu Glu Val Leu Gln Ala Leu Leu Glu
        50                  55                  60
Ala Thr Glu Glu Phe Glu Leu Arg Tyr Gln Arg Ala Phe Ser Asp Leu
65                  70                  75                  80
Thr Ser Gln Leu His Ile Thr Gln Asp Thr Ala Gln Gln Ser Phe Gln
                85                  90                  95
Gln Val Met Gly Glu Leu Phe Arg Asp Gly Thr Asn Trp Gly Arg Ile
            100                 105                 110
Val Ala Phe Phe Ser Phe Gly Arg Ala Leu Cys Val Glu Ser Ala Asn
        115                 120                 125
Lys Glu Met Thr Asp Leu Leu Pro Arg Ile Val Gln Trp Met Val Asn
    130                 135                 140
Tyr Leu Glu His Thr Leu Gln Pro Trp Met Gln Glu Asn Gly Gly Trp
145                 150                 155                 160
Glu Ala Phe Val Gly Leu Tyr Gly Lys Asn Ala Ala Ala Gln Ser Arg
                165                 170                 175
Glu Ser Gln Glu Arg Phe Gly Arg Leu Leu Thr Ile Val Met Leu Thr
            180                 185                 190
Gly Val Phe Ala Leu Val Cys Tyr Met Arg Arg Arg
        195                 200

<210> SEQ ID NO 7
<211> LENGTH: 229
<212> TYPE: PRT
<213> ORGANISM: Artificial Sequence
<220> FEATURE:
<223> OTHER INFORMATION: BCL2 proteins

<400> SEQUENCE: 7

Met Ser Ser Asn Arg Glu Leu Val Ile Asp Phe Val Ser Tyr Lys
 1               5                  10                  15
Leu Ser Gln Arg Gly His Cys Trp Ser Glu Leu Glu Glu Asp Glu
                20                  25                  30
Asn Arg Thr Asp Thr Ala Ala Glu Ala Glu Met Asp Ser Val Leu Asn
```

```
            35                  40                  45
Gly Ser Pro Ser Trp His Pro Ala Gly His Val Val Asn Gly Ala
 50                  55                  60

Thr Val His Arg Ser Ser Leu Glu Val His Glu Ile Val Arg Ala Ser
 65                  70                  75                  80

Asp Val Arg Gln Ala Leu Arg Asp Ala Gly Asp Glu Phe Glu Leu Arg
                 85                  90                  95

Tyr Arg Arg Ala Phe Ser Asp Leu Thr Ser Gln Leu His Ile Thr Pro
            100                 105                 110

Gly Thr Ala Tyr Gln Ser Phe Glu Gln Val Val Asn Glu Leu Phe His
            115                 120                 125

Asp Gly Val Asn Trp Gly Arg Ile Val Ala Phe Phe Ser Phe Gly Gly
130                 135                 140

Ala Leu Cys Val Glu Ser Val Asp Lys Glu Met Arg Val Leu Val Gly
145                 150                 155                 160

Arg Ile Val Ser Trp Met Thr Thr Tyr Leu Thr Asp His Leu Asp Pro
                165                 170                 175

Trp Ile Gln Glu Asn Gly Gly Trp Glu Arg Phe Val Asp Leu Tyr Gly
            180                 185                 190

Asn Asn Ala Ala Ala Glu Leu Arg Lys Gly Gln Glu Thr Phe Asn Lys
            195                 200                 205

Trp Leu Leu Thr Gly Ala Thr Val Ala Gly Val Leu Leu Gly Ser
210                 215                 220

Leu Leu Ser Arg Lys
225

<210> SEQ ID NO 8
<211> LENGTH: 233
<212> TYPE: PRT
<213> ORGANISM: Artificial Sequence
<220> FEATURE:
<223> OTHER INFORMATION: BCL2 proteins

<400> SEQUENCE: 8

Met Ser Gln Ser Asn Arg Glu Leu Val Val Asp Phe Leu Ser Tyr Lys
 1               5                   10                  15

Leu Ser Gln Lys Gly Tyr Ser Trp Ser Gln Phe Ser Asp Val Glu Glu
             20                  25                  30

Asn Arg Thr Glu Ala Pro Glu Gly Thr Glu Ser Glu Met Glu Thr Pro
         35                  40                  45

Ser Ala Ile Asn Gly Asn Pro Ser Trp His Leu Ala Asp Ser Pro Ala
 50                  55                  60

Val Asn Gly Ala Thr Ala His Ser Ser Ser Leu Asp Ala Arg Glu Val
 65                  70                  75                  80

Ile Pro Met Ala Ala Val Lys Gln Ala Leu Arg Glu Ala Gly Asp Glu
                 85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160
```

-continued

```
Val Leu Val Ser Arg Ile Ala Ala Trp Met Ala Thr Tyr Leu Asn Asp
            165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
            195                 200                 205

Arg Phe Asn Arg Trp Phe Leu Thr Gly Met Thr Val Ala Gly Val Val
            210                 215                 220

Leu Leu Gly Ser Leu Phe Ser Arg Lys
225             230
```

TRANSGENIC CANCER MODELS IN FISH

RELATED APPLICATION

This application claims priority from U.S. Provisional Application No. 60/409,585, filed Sep. 11, 2002.

BACKGROUND OF THE INVENTION

The present invention relates to transgenic animals. Specifically, the invention relates to transgenic fish and methods for their use.

Animal models of disease states play an important role in identifying the underlying biochemical mechanisms of particular diseases, as well as discovering therapeutic agents to eradicate the disease or otherwise lessen its symptoms. For example, rabbit models of familial hypercholesterolemia, rat models of non-insulin-dependent diabetes mellitus, mouse models of cancer and hamster models for spontaneous atrial thrombosis are known. Additionally, animal models for genetic diseases have arisen spontaneously in a variety of species, including mice, cats and dogs. Working with such large animals poses several drawbacks.

For example, many of the animals used in such models are relatively large vertebrates which take up a large amount of research space, are costly to feed and otherwise maintain, have slow reproductive cycles, produce relatively few offspring at one time, and cannot effectively mimic all desired disease states. Researchers have attempted to obtain animal models that solve some of these problems, but have not yet obtained such animal models for all desired diseases. For example, transgenic fish models of premalignant and non-neoplastic or non-malignant hyperproliferative disorders (e.g., inflammation and retinopathy) would also be useful. Additionally, although fish have been utilized to detect mutagens in aquatic environments, there are currently no transgenic fish models that develop any cancers relevant in human cancer research, including, for example, human T-cell leukemias, non-Hodgkin's lymphoma, high-grade astrocytoma, rhabdomyosarcoma, neuroblastoma, neuorendocrine carcinoma, pancreatic carcinoma, ovarian carcinoma, testicular carcinoma, stomach cancer, colon cancer, renal cancer, melanoma and acute or chronic myeloid leukemia.

Human T-cell leukemias can arise from oncogenes activated by specific chromosomal translocations involving T-cell receptor genes. In particular, T-cell acute lymphoblastic leukemia is a malignant disease of thymocytes, accounting for about 10% to about 15% of pediatric and about 25% of adult acute lymphoblastic leukemia cases. Although some therapies are available for T-cell acute lymphoblastic leukemia, they are not as effective as desired.

Follicular center cell non-Hodgkin's lymphomas are a common and generally indolent type of B-cell lymphoma that occurs almost exclusively in adults, and 80% of follicular center cell lymphomas have a t(14;18) chromosomal translocation. Molecular analysis of the breakpoints of the 14;18 translocation identified BCL2 as the gene on chromosome 18 that is overexpressed due to its translocation into the IgH locus on chromosome 14. Functional studies revealed that BCL2 defines a new class of proto-oncogene products that act to prolong cell survival, rather than through more typical effects on cell differentiation or proliferation. It has since been learned that BCL2 is a member of a large family of highly conserved proteins that either inhibit or promote apoptosis. In addition, BCL2 and it's pro-survival relatives may be important for the aberrant survival of many human cancers, not just those with overexpression of BCL2 due to the t(14;18).

High-grade astrocytomas are among the most common and devastating adult brain tumors, spreading so rapidly that patients seldom survive more than 9-12 months. Despite progress in surgical, radiation and chemotherapy technologies, there has been little improvement in the outcome of patients with astrocytoma over the last twenty years. Clearly, novel approaches are needed to better understand the biological basis of this disease before effective therapies can be developed.

Rhabdomyosarcomas are a heterogeneous group of malignant tumors of skeletal muscle progenitors and are the most common soft-tissue sarcoma in children of 15 years or younger. Rhabdomyosarcoma consists of two histologic subtypes, alveolar and embryonal, each characterized by the misexpression of different subsets of genes. The aggressive nature of these tumors makes their effective treatment particularly difficult. While rhabdomyosarcomas can be observed in genetically engineered, mammalian disease models, they are often associated with other tumor types. While informative, a more specific model of rhabdomyosarcoma is necessary to elucidate its molecular basis and to identify novel genes that may ultimately be used as targets for the development of novel therapeutic strategies.

The mutations and gene rearrangements commonly seen in acute myeloid leukemias typically result from a chromosomal translocations such as the t(8;21) or t(15;17), generate chimeric oncoproteins by fusing one or two transcription factors (Look, 1997). However, these alterations are not sufficient to explain the induction of acute leukemia. Additional animal models are needed, for example, to permit the unbiased detection of mutations in many potentially novel genes that lead to leukemia, which is currently not possible in other mammalian models.

Many of the underlying mechanisms that lead to neuroblastoma, neuorendocrine carcinoma, pancreatic carcinoma, ovarian carcinoma, testicular carcinoma, stomach cancer, colon cancer, renal cancer, melanoma and acute or chronic myeloid leukemia have yet to be fully understood. Identifying the genes mutated in these diseases will lead to new insights into cancer as a whole. Additionally, using a vertebrate model system in which genetic or chemical suppressors can be identified that inhibit or delay disease progression, or sensitivity to chemotherapy or radiation-induced programmed cell death, will be necessary to identify new drug targets for the development of targeted chemotherapies. For example, a model system is needed, which does not require an a priori knowledge of the specific target. Target elucidation may be accomplished after the modulating target drug or agent is demonstrated safe and effective, which, thus, saves both time and expense in the drug discovery process.

A further understanding of the cellular and molecular genetic features of various disease states such as the cancers listed above are needed. An appropriate animal model would be invaluable to elucidate the multistep process of genetic mutations, as well as to develop more effective drugs. The present invention addresses these needs.

SUMMARY OF THE INVENTION

It has been discovered that transgenic fish may be produced that can advantageously be utilized as a fish model of mammalian disease, including cancers, and particularly human cancers. Accordingly, transgenic fish are provided, as are methods of their production and use.

In one aspect of the invention, a transgenic fish is provided whose genome has stably-integrated therein an oncogene operably linked to a promoter. In one form, transgenic fish is provided whose genome has stably integrated therein a ubiquitous gene promoter, a reporter gene comprising a strong transcription stop-site, and an oncogene, wherein the reporter gene is flanked by site-specific recombinase recognition sites. Preferably the promoter is an organ- or tissue-specific promoter. In one embodiment, the promoter is a lymphoid-specific promoter. In certain forms of the invention, the oncogene induces a leukemia or lymphoma, including a T-cell lymphoma or a T-cell acute lymphoblastic leukemia. In other embodiments, the oncogene induces non-Hodgkin's lymphoma, high-grade astrocytoma, rhabdomyosarcoma, neuroblastoma, neuorendocrine carcinoma, pancreatic carcinoma, ovarian carcinoma, testicular carcinoma, stomach cancer, colon cancer, renal cancer melanoma and acute or chronic myeloid leukemia.

In a second aspect of the invention, methods of making a transgenic fish are provided. In one form, a method includes introducing nucleic acid into a fertilized fish embryo, wherein the nucleic acid comprises an oncogene operably linked to a promoter, and developing the fish embryo into a transgenic fish. In another form, a method includes introducing nucleic acid into a unfertilized fish egg, wherein the nucleic acid comprises an oncogene operably linked to a promoter, fertilizing the fish egg, and developing the fish embryo into a transgenic fish.

In another aspect of the invention, methods of screening for drugs or agents that modulate (e.g., enhance or suppress) oncogene-mediated neoplastic or hyperplastic transformation. In one embodiment, a method includes (a) contacting or otherwise exposing a transgenic fish (e.g., an adult transgenic fish or a transgenic fish embryo) to a test drug or agent, wherein the transgenic fish has a genome that has stably-integrated therein an oncogene operably linked to a promoter; (b) determining if the test drug or agent modulates (e.g., enhances or suppresses) oncogene-mediated neoplastic or hyperplastic transformation; and (c) classifying the test drug or agent as an drug or agent that modulates oncogene-mediated neoplastic or hyperplastic transformation if the test drug or agent suppresses or enhances oncogene-mediated neoplastic or hyperplastic transformation.

In another embodiment, a method includes (a) contacting or otherwise exposing a transgenic fish (e.g., an adult transgenic fish or a transgenic fish embryo) to a test drug or agent, wherein the transgenic fish has a genome that has stably integrated therein a ubiquitous gene promoter, a reporter gene comprising a strong transcription stop-site, and an oncogene, and wherein the reporter gene is flanked by site-specific recombinase recognition sites; (b) determining if the test drug or agent modulates oncogene-mediated neoplastic or hyperplastic transformation; and (c) classifying the test drug or agent that modulates oncogene-mediated neoplastic or hyperplastic transformation.

In yet another aspect of the invention, methods of screening for drugs or agents that modulate the sensitivity of transgenic cells to treatment with radiation or chemotherapy are provided. A method includes (a) contacting or otherwise exposing a transgenic fish (e.g., an adult transgenic fish or a transgenic fish embryo) to a test drug or agent, wherein the transgenic fish has a genome that has stably-integrated therein an oncogene operably linked to a promoter; (b) determining if the test drug or agent modulates (e.g., suppresses or enhances) sensitivity to radiation- or chemotherapy-induced programmed cell death; and (c) classifying the test drug or agent as an drug or agent that modulates sensitivity to radiation- or chemotherapy-induced programmed cell death if the test drug or agent suppresses or enhances sensitivity to radiation- or chemotherapy-induced programmed cell death.

In another embodiment, a method includes (a) contacting or otherwise exposing a transgenic fish (e.g., an adult transgenic fish or a transgenic fish embryo) to a test drug or agent, wherein the transgenic fish has a genome that has stably integrated therein a ubiquitous gene promoter, a reporter gene comprising a strong transcription stop-site, and an oncogene, and wherein the reporter gene is flanked by site-specific recombinase recognition sites; (b) determining if the test drug or agent the sensitivity of transgenic cells to treatment with radiation or chemotherapy; and (c) classifying the test drug or agent that modulates the sensitivity of transgenic cells to treatment with radiation or chemotherapy if the test drug or agent suppresses or enhances sensitivity to radiation- or chemotherapy-induced programmed cell death.

In another aspect of the invention, methods of identifying mutations that modulate oncogene-mediated neoplastic or hyperplasic transformation or sensitivity to radiation- or chemotherapy-induced programmed cell death are provided. In one embodiment, a method includes (a) mutagenizing a transgenic fish whose genome has stably-integrated therein an oncogene operably linked to a promoter; (b) mating the transgenic fish with a non-mutagenized fish to produce $F_1$ offspring; (c) obtaining eggs from the $F_1$ offspring; (d) fertilizing the eggs with inactivated sperm to produce $F_2$ offspring; (e) determining the presence and extent of neoplasia or hyperplasia or sensitivity to radiation- or chemotherapy-induced programmed cell death in the $F_2$ offspring; and (f) identifying the modulator (e.g., enhancer or suppressor) mutation in the $F_1$ offspring.

In another embodiment, a method includes (a) mutagenizing a transgenic fish whose genome has stably integrated therein a ubiquitous gene promoter, a reporter gene comprising a strong transcription stop-site, and an oncogene, and wherein the reporter gene is flanked by site-specific recombinase recognition sites; (b) mating the transgenic fish with a non-mutagenized fish to produce $F_1$ offspring; (c) obtaining eggs from the $F_1$ offspring; (d) fertilizing the eggs with inactivated sperm to produce $F_2$ offspring; (e) determining the presence and extent of neoplasia or hyperplasia or sensitivity to radiation- or chemotherapy-induced programmed cell death in the $F_2$ offspring; and (f) identifying the mutation that modulates oncogene-mediated neoplastic or hyperplastic transformation or that modulates sensitivity to radiation- or chemotherapy-induced programmed cell death.

In other embodiments, a method includes (a) mutagenizing a transgenic first fish, wherein said transgenic first fish is homozygous for a transgene; (b) mating said transgenic first fish with a non-mutagenized second fish, to produce $F_1$ fish, wherein said non-mutagenized second, fish is homozygous for the transgene; (c) obtaining eggs from female $F_1$ fish; (d) fertilizing said eggs with inactivated sperm; (e) subjecting said fertilized eggs to early pressure to produce gynogenetic diploid $F_2$ fish; (f) examining the rate of onset and/or extent of organ or tissue-specific neoplasia or hyperplasia to identify $F_1$ fish that are heterozygous for inactivation of a tumor suppressor gene; and (g) optionally out-crossing the $F_1$ female fish to identify the mutation.

In yet another aspect of the invention, methods of co-expressing more than one mammalian oncogene in a transgenic fish are provided. In one embodiment, a method includes: (a) producing a first transgenic fish whose genome has stably-integrated therein a first mammalian oncogene operably linked to a first promoter; (b) producing a second transgenic fish whose genome has stably-integrated therein a second mammalian oncogene operably linked to a second promoter, wherein said first mammalian oncogene and said second mammalian oncogene are different; and (c) mating said first transgenic fish with said second transgenic fish to produce offspring, which co-express said different mammalian oncogenes.

In another embodiment, a method includes (a) producing a transgenic fish whose genome has stably integrated therein a ubiquitous gene promoter, a reporter gene comprising a strong transcription stop-site, and a first mammalian oncogene, wherein the reporter gene is flanked by site-specific recombinase recognition sites; (b) producing a second transgenic fish whose genome has stably-integrated therein a second mammalian oncogene operably linked to a second promoter; wherein said first mammalian oncogene and said second mammalian oncogene are different; and (c) mating said first transgenic fish with said second transgenic fish to produce offspring, which coexpress said different mammalian oncogenes.

In another aspect of the invention, methods of making a stable transgenic fish model of human cancers are provided, wherein an oncogene can be regulated in any tissue by using regulatable site-specific recombinases. In one form, a method includes (a) producing a first transgenic fish whose genome has stably integrated therein a cassette comprising a ubiquitous gene promoter, a reporter gene comprising a strong transcription stop-site and flanked by site-specific recombinase recognition sites, and an oncogene; (b) producing a second transgenic fish whose genome has stably integrated therein a site-specific recombinases operably linked to a heat shock promoter; (c) mating said first transgenic fish with said second transgenic fish to produce $F_1$ progeny fish; (d) laser-activating cells of said $F_1$ progeny fish, whereby said laser activation causes recombination and excision of said reporter gene and juxtaposition of said ubiquitous gene promoter adjacent to said oncogene in the cells of said $F_1$ progeny fish.

It is an object of the invention to provide transgenic fish that may be used in, for example, an animal model of disease, preferably cancer. Preferably the cancer is a human cancer.

It is another object of the invention to provide transgenic fish that may be used as an animal model to discover drugs or genetic modifiers that sensitize tumor cells over-expressing BCL2 or cMYC to the apoptosis-inducing effects of treatment with radiation or chemotherapeutic drugs.

It is another object of the invention to provide methods of making the above-referenced transgenic fish.

It is yet another object of the invention to provide methods of using the above-referenced transgenic fish, including using the fish in methods of screening for drugs or agents that modulate disease, particularly oncogene-mediated transformation, and for the discovery of drugs, agents and/or genes involved in the neoplastic or hyperplastic process, including tumor suppressor genes and potential drug targets.

It is a further object of the invention to provide methods of co-expressing more than one mammalian oncogene in a transgenic fish, including, for example, to determine accelerated onset of disease.

These and other objects and advantages of the present invention will be apparent from the descriptions herein.

BRIEF DESCRIPTION OF THE FIGURES

FIG. 1. FIGS. 1A, 1C, and 1E, are side views of the fish and FIGS. 1B, 1D, and 1F are the top views of the same fish shown in FIGS. 1A, 1C, and 1E, respectively. FIG. 1G is a side view of a RAG2-GFP fish while 1H is a side view of RAG2-mcMYC $F_0$ fish injected on the RAG2-GFP background and obtained by GFP fluorescence. Tumors are denoted by arrows and labeled nose (N), eye (E), fin (F), probable thymic tumors (T).

FIGS. 1K-1L, kidney; FIGS. 1M-1N, musculature; FIGS. 1O-1P, nasal region. Tumors are denoted by arrows and labeled fin (F), kidney (K); muscle (M); skin (S) and gut (G). FIGS. 1I, 1K, 1M, and 1O depict wild-type fish, and FIGS. 1J, 1L, 1N, and 1P represent transgenic fish with tumors. Scale bars in FIGS. 1I-J represent 1 mm, in FIGS. 1K-N represent 100 microns, and in FIGS. 1O-P represent 500 microns.

FIG. 2. FIG. 2 depicts views of transverse paraffin sections of transgenic fish produced by introduction of nucleic acid comprising RAG2-cMYC and analyzed for RNA expression of T-cell genes, as more fully described in Example 1C, in order to identify tumor cell lineage. FIGS. 2A-2B, RNA in situ analysis with a mouse cMYC RNA probe; FIGS. 2C-2D, zebrafish RAG2.

FIG. 3.

FIG. 4.

FIG. 4B depicts a touch prep of $F_0$ mosaic RAG2-mcMYC tumor-bearing fish; FIG. 4C depicts transplanted tumor cell fish from FIG. 4A; and FIG. 4D depicts wild-type fish. Scale bars in FIGS. 4B-4D represent 10 microns.

FIGS. 4F-H are irradiated controls and FIGS. 4G-I are transplants. Scale bars in FIGS. 4F-I represent 50 microns.

FIG. 5 depicts an example of a plasmid vector that may be used to incorporate an oncogene sequence to produce an oncogene protein fused to a green fluorescent protein (GFP). GM2 denotes the green fluorescent open reading frame and pA denotes the synthetic polyadenylation sequence used in the construct. T7 and T3 denote promoters used for in vitro transcription and vector sequence is noted as single lines on the circle. Restrictions sites are noted. For oncogene constructs, the GM2 open reading frame has been excised and replaced with sequences for mouse cMYC, EGFP-mcMYC, EGFP-BCL2, TAN1, and HOX11.

FIG. 6 depicts one example of a potential ethylnitrosurea (ENU)-induced genetic modifier screen in the zebrafish. Zebrafish lines are indicated as X plus superscript of either wik or AB. Point mutations induced by ENU are noted as asterisks and are linked to the wik alleles. Transgenic lines are noted (RAG2-GFP as EGFP and RAG2-mcMYC as cMYC) and plus signs designate no transgene being passed on (i.e., the fish are heterozygotes if they are cMYC/+ for example, but homozygous for the transgene if they are cMYC/cMYC). Breeding is designated by converging arrows. Mutations will be identified in the generation noted by "Modifier Mutation" while the line is maintained without disease in the generation noted by "Line Maintained."

FIG. 7 depicts the RAG2-Lox-dsRED2-EGFP-mMYC construct. A) A diagram of the construct. B) Transient injection of this construct drives expression of dsRED in developing mosaic fish while the EGFP-mMYC transgene is not expressed, as determined by GFP fluorescent microscopy (C). Poly-adenylation and transcription stop sites note (pA).

FIG. 8 depicts CRE-mediated excision of dsRED2 allele in fish transiently injected with both the CMV-Lox-dsRED2-EGFP and PCS2+CRE plasmids. A) A diagram of the construct. B) Transient injection of the CMV-Lox-dsRED2-EGFP construct in the absence of PCS2+CRE plasmid drives expression of dsRED in developing mosaic fish (B) but not GFP (C). Meanwhile, fish injected with both the CMV-Lox-dsRED2-EGFP and PCS2+CRE plasmids are both sdRED2 (D) and GFP labeled (E). Poly-adenylation and transcription stop sites note (pA).

FIG. 9 depicts CRE-mediated excision of dsRED2 allele in fish transiently injected with both the CMV-Lox-dsRED2-EGFP and CRE RNA. Bright field images of injected fish (A,D). Transient injection of the CMV-Lox-dsRED2-EGFP construct in the absence of CRE RNA drives expression of dsRED in developing mosaic fish (B) but not GFP (C). Meanwhile, fish injected with both the CMV-Lox-dsRED2-EGFP and CRE RNA fail to express sdRED2 (E) but strongly express GFP (F). This excision event is 100% efficient.

FIG. 10 depicts RT-PCR expression of T-ALL oncogenes in zebrafish MYC-induced leukemias. Tumor samples are noted by numbers. T-ALL oncogenes include SCL, LMO2, LMO1, HOX-11, TLX-3a, and TLX-3b. Beta-actin and EF1-alpha are housekeeping genes and verify that equal amounts of cDNA were used in each sample.

FIG. 11 depicts RNA in situ hybridization of paraffin embedded sections with Scl and Lmo2. Anti-sense probes (a-) and control sense probes (s-). MYC-G and MCMYC are tumors from mosaic injected RAG2-mMYC fish.

FIG. 12 depicts the amino acid alignment and phylogenetic analysis of vertebrate BCL2 proteins. (A) Alignment of BCL2 and BCL-xL proteins. Alignments shown are from zebrafish (z) BCL2 (SEQ ID NO:1) and BCL-xL (SEQ ID NO:5), Xenopus (x) BCL2 (SEQ ID NO:2) and BCL-xL (SEQ ID NO:6), chicken (c) BCL2 (SEQ ID NO:3) and BCL-xL (SEQ ID NO:7), and human (h) BCL2 (SEQ ID NO:4) and BCL-xL (SEQ ID NQ:8). Amino acid residues conserved among both BCL2 and BCL-xL family members are indicated (#) while amino acid residues conserved among only BCL2 proteins are noted (*). Conserved BH1, BH2, BH3, and BH4 domains are denoted by a single line above the alignment. Dashes denote gaps introduced to maximize alignment. Sequence alignments were made using Megalign. (B) Diagram showing conserved domain homologies when zebrafish bcl-2 is compared to the human BCL2 protein. (C) Phylogenetic analysis of vertebrate BCL2 and BCL-xL proteins.

DETAILED DESCRIPTION OF THE INVENTION

Figure 1A:
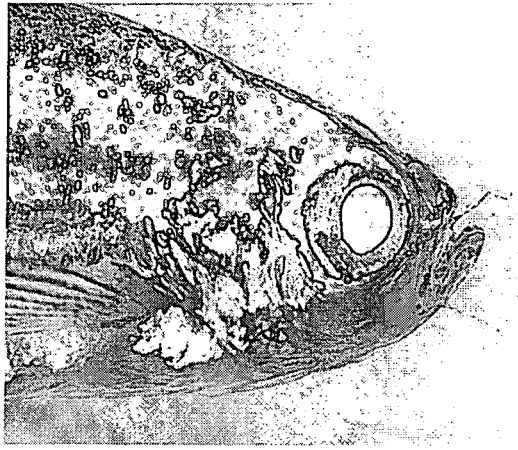
FIGS. 1A-1H depict views of transgenic fish produced by introduction of nucleic acid comprising the RAG2 promoter-mouse cMYC (mcMYC) transgene (also referred to herein as RAG2-mcMYC) and shows the external morphology of tumorigenic RAG2-mcMYC fish, as more fully described in Examples 1B and 1C. Wild type fish are seen in FIGS. 1A, 1B, 1G, 1I, 1K, 1M and 1O; RAG2-mcMYC $F_0$ mosaic fish are seen in FIGS. 1C-1F, 1H, 1J, 1L, 1N and 1P.
Figure 1B:
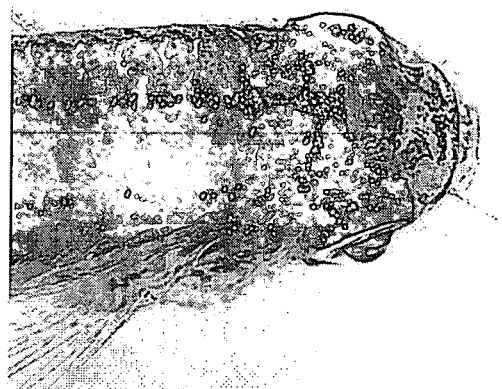

For the purposes of promoting an understanding of the principles of the invention, reference will now be made to preferred embodiments, and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to transgenic fish and methods for their production and use. In one aspect of the invention, transgenic fish are provided whose genome has stably-incorporated therein nucleic acid comprising an oncogene operably linked to a promoter. In yet other aspects of the invention, methods of making and methods of using the transgenic fish are provided. In certain forms of the invention, a method of screening for, or otherwise identifying, drugs or agents that modulate oncogene-mediated neoplastic or hyperplastic transformation or increase the sensitivity of transgenic cells to the toxic effects of radiation or chemotherapy are provided. Additionally, the transgenic fish described herein may be used as a model to study conserved pathways that lead to oncogene-mediated cancer progression in vertebrates, including, for example, non-Hodgkin's lymphoma, high-grade astrocytoma, rhabdomyosarcoma, neuroblastoma, neuorendocrine carcinoma, pancreatic carcinoma, ovarian carcinoma, testicular carcinoma, stomach cancer, colon cancer, renal cancer melanoma and acute or chronic myeloid leukemia, and cMYC-induced T-cell acute lymphoblastic leukemia.

In one aspect of the invention, stably transformed transgenic fish are provided. In one embodiment, a transgenic fish has a genome which has stably-integrated, or otherwise incorporated, therein an introduced oncogene operably linked to a promoter. The promoter is preferably an organ- or tissue-specific (including cell-specific) promoter or a promoter that can be regulated in a specific tissue. Most preferably, the promoter is a lymphoid-specific promoter, including T-cell or B-cell-specific promoters, such as a RAG1 or RAG2 promoter. The oncogene is typically from an animal other than a fish or from the fish itself and may advantageously be part of a recombinant vector as further described herein. Preferably the oncogene is a mammalian oncogene. Such fish may form a stable fish line in that they have the capacity to reproduce and pass their genetic information relating to the oncogene to their progeny.

A wide variety of fish may be utilized in the invention. Exemplary fish include teleost fish, such as zebrafish (*Danio rerio*), medaka (*Oryzias latipes*), mummichog (*Fundulus heteroclitus*), killifish (Genus *Fundulus*), catfish (Genus *Ictalurus*), such as channel catfish; carp (Genus *Cyprinus*), such as common carp; and trout or salmon (e.g., Genus *Salvelinus, Salmo,* and *Oncorhynchus*).

Zebrafish, in particular, may be advantageously utilized as compared to other animal models. For example, zebrafish are amenable to genetic screens, modifier screens, and chemical screens; develop rapidly ex-utero; are transparent for much of their life cycle and produce large clutches of offspring weekly. Zebrafish can be raised in relatively small facilities (housing up to about 54 adult fish in a single 9 liter tank), and can reliably produce offspring in large quantities, with each mature female typically laying between 100 to 300 eggs per week. These eggs are fertilized externally, and the embryos are transparent allowing the early development of hematopoietic tissues and other organ and tissue systems to be directly observed using only a dissecting microscope. Embryonic development is extremely rapid with most organ systems including blood cell formation being fully developed by 5 days post fertilization. Full reproductive maturation is reached by about 3 months.

The vector includes an oncogene operably linked to a promoter. Preferably the promoter is an organ- or tissue-specific promoter. As known in the art, an oncogene is a gene whose expression can lead to alteration of the control of cellular proliferation or to the prevention of programmed cell death. A wide variety of oncogenes may be utilized in the nucleic acid constructs described herein. The oncogenes may be of viral or cellular origin. Oncogenes of cellular origin include endogenous oncogenes. Such oncogenes, when expressed, lead to neoplastic or hyperplastic transformation of a cell. Exemplary oncogenes include MYC, SRC, FOS, JUN, MYB, RAS, ABL, BCL2, HOX11, HOX11L2, TAL1/SCL, LMO1, LMO2, EGFR, MYCN, MDM2, CDK4, GLI1, IGF2, activated RAS, activated EGFR, mutated genes, such as FLT3-ITD, mutated and activated versions of TP53, PAX3, PAX7, BCR/ABL, HER2/NEU, FLT3R, FLT3-ITD,SRC, RAS, ABL, TAN1, PTC, B-RAF, PML-RARα, E2A-PBX1, and NPM-ALK, as well as fusion of members of the PAX and FKHR gene families.

Other exemplary oncogenes are well known in the art and several such examples are described in, for example, *The Genetic Basis of Human Cancer* (Vogelstein, B. and Kinzler, K. W. eds. McGraw-Hill, New York, N.Y., 1998), such as in Tables 5.1-5.3 of Look, A. T., *Genes altered by chromosomal translocations in leukemias and lymphoma*, pages 109-141, which is incorporated herein by reference in its entirety. Mammalian homologues of such genes are preferred because they can be distinguished from endogenous fish genes. Further preferred are human homologues of such genes. The corresponding sequences of such oncogenes, including the human homologues of the oncogenes, are known and may be found, for example, in the NCBI database.

The oncogene is selected based on the form of cancer it is desired that the transgenic fish will develop. For example, mutated or activated genes of the RAS family may be used for induction of a wide variety of types of cancers, such as renal, pancreatic or colon cancers, and HOX11 and TAL1 may be used for T-cell cancer induction, etc. Preferably the oncogenes are T-cell or B-cell oncogenes. Most preferably, the T-cell oncogenes are members of the MYC, TAL1/SCL, TAL2, LYL1, LMO1, LMO2, HOX11, TAN1, and LYL1 gene families, and the B-cell oncogenes are members of the MYC, E2A-PBX1, E2A-HLF, TEL-AML1, BCL6, BCL3, LYT10, MLL, HOX or PAX5 gene families. In one form, the oncogene is MYC, such as c-MYC (GenBank Accession No. XM_122917.1). Expression of such a nucleotide sequence in T-cell progenitors of the fish leads to development of acute T-cell lymphoblastic leukemia or lymphoma. The invention is not limited to such an oncogene sequence. For example, altered forms of the oncogene nucleotide sequence, such as cMYC or the other oncogene nucleotide sequences described herein, that increase or decrease the transformation potential of the oncogene are also envisioned.

In one form of the invention, the oncogene utilized in the invention may have a cMYC nucleotide sequence (GenBank Accession No. XM_122917.1) that has at least about 60%, preferably at least about 70%, more preferably at least about 80%, and most preferably at least about 90% identity to the nucleotide sequence or the other oncogene nucleotide sequences discussed herein.

Percent identity may be determined, for example, by comparing sequence information using the advanced BLAST computer program, version 2.0.8, available from the National Institutes of Health. The BLAST program is based on the alignment method of Karlin and Altschul, (1990) *Proc. Natl. Acad. Sci. USA* 87:2264-2268 and as discussed in Altschul, et al., (1990) *J. Mol. Biol.* 215:403-410; Karlin and Altschul, *Proc. Natl. Acad. Sci. USA* (1993) 90:5873-5877; and Altschul et al. (1997) *Nucleic Acids Res.* 25:3389-3402.

Additionally, the oncogene may include nucleotide sequences having substantial similarity to the cMYC nucleotide sequence (GenBank Accession No. XM_122917.1) or the other oncogene nucleotide sequences discussed herein. By "substantial similarity", it is meant herein that the nucleotide sequence is sufficiently similar to a reference nucleotide sequence that it will hybridize therewith under moderately stringent conditions. This method of determining similarity is well known in the art to which the invention pertains. Briefly, moderately stringent conditions are defined in Sambrook et al., *Molecular Cloning: A Laboratory Manual*, 2$^{nd}$ ed. Vol. 1, pp. 101-104, Cold Spring Harbor Laboratory Press (1989) as including the use of a prewashing solution of 5×SSC (a sodium chloride/sodium citrate solution), 0.5% sodium dodecyl sulfate (SDS), 1.0 mM ethylene diaminetetracetic acid (EDTA) (pH 8.0) and hybridization and washing conditions of 55° C., 5×SSC. A further requirement of the nucleotide sequence of the oncogene is that it encode a protein having cell neoplastic transformation ability. That is, the proteins have the ability to convert normal (i.e., non-cancerous cells) into cancerous cells (i.e., tumors).

The oncogene, also considered herein as the transgene, the gene which is introduced into the genome described herein, may be either synthesized in vitro or isolated from a biological source. Such methods of synthesis and isolation are well known to the skilled artisan.

The oncogene is operably linked to a promoter. Preferably the promoter is a organ- or tissue- (including cell-) specific promoter. Most preferably, the promoter is a lymphoid-specific promoter. For example, by "lymphoid-specific," it is meant herein that the promoter drives expression of the oncogene only in tissue of lymphoid origin, such as in B- and T-cell progenitor cells known to the art. The lymphoid-specific promoters may be derived from any lymphoid-specific genes. Exemplary lymphoid-specific promoters that may advantageously be used in the invention include promoters of the recombination activating genes (RAG), including RAG1 and RAG2; LCK, which encodes a T-cell-specific, non-receptor tyrosine kinase; IgM enhancer elements, and CD2. Several promoters that direct tissue-restricted expression have been identified, for example, zebrafish RAG1 (Jessen et al., *Nat. Genet.*, 23: 16-17 (1999)) and zebrafish RAG2 (Jessen et al., *Genesis*, 29: 156-162, (2001)) for lymphoid tissues, Keratin-8 for epithelial cells (Gong et al., 2002), Islet-1 for neural-specific expression (Motoike et al., *Genesis*, 28:75-81 (2000)), PDX-1 and Insulin for pancreas (Huang et al., *Genesis*, 30:134-6 (2001)), GFAP for glial cells, and MYO-D and alpha-actin for muscle (Higashima, 1997). Promoters having at least about 70% identity, at least about 80% identity, and further at least about 90% identity to the nucleotide sequences of the tissue-specific promoters described herein are also envisioned, provided that they promote transcription of the oncogene to which they are operably linked. Since most mammalian promoters are found not to work well in fish, then the genomic regulatory sequences of the zebrafish, fugu or other fish species often must be specifically cloned upstream, within, and downstream of the coding sequence of interest, which may be accomplished by procedures routine to those skilled in the art. In certain embodiments, the promoter is T-cell progenitor-specific in that it will drive expression of the oncogene only in T-cell progenitors. Such a construct may be made by using the RAG2 or LCK genomic sequences upstream of the coding region of the gene. The genomic sequences are first cloned upstream of GFP to see if they can drive expression of this fluorescent marker in a tissue-specific fashion during development, and if so, then the same sequences are used to drive the expression of cMYC and other oncogenes. Similar procedures may be utilized for construction of other, e.g., zebrafish, organ- and tissue-specific promoters, which are well known to those of skill in the art, such as those cloned from the genes encoding tyrosine hydroxylase for the dopaminanergic nervous system, MYO-D for the muscle system, and MPO or PU.1 for the myeloid system.

As defined herein, a nucleotide sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary join two protein coding regions, contiguous and in reading frame. Since enhancers may function when separated from the promoter by several kilobases and intron sequences may be of variable lengths, some nucleotide sequences may be operably linked but not contiguous.

The transgene may be included in a vector for delivery. A vector, as used herein and as known in the art, refers to a nucleic acid construct that includes genetic material designed to direct transformation (i.e., the process whereby genetic material of an individual cell is altered by incorporation of exogenous DNA into its genome) of a targeted cell. A vector may contain multiple genetic elements positionally and sequentially oriented, i.e., operably linked with other necessary or desired elements such that the nucleic acid in a cassette can be transcribed and, if desired, translated in the microinjected, single-cell fertilized embryo.

Recombinant expression vectors may be constructed by incorporating the above-recited nucleotide sequences within a vector according to methods well known to the skilled artisan and as described, for example, in Sambrook et al., *Molecular Cloning: A Laboratory Manual*, Cold Springs Harbor Laboratory, 2$^{nd}$ ed., Cold Springs Harbor, N.Y. (1989). Other references describing molecular biology and recombinant DNA techniques include, for example, *DNA Cloning 1: Core Techniques*, (D. N. Glover, et al., eds., IRL Press, 1995); *DNA Cloning 2: Expression Systems*, (B. D. Hames, et al., eds., IRL Press, 1995); *DNA Cloning 3: A Practical Approach*, (D. N. Glover, et al., eds., IRL Press, 1995); *DNA Cloning 4: Mammalian Systems*, (D. N. Glover, et al., eds., IRL Press, 1995); *Oligonucleotide Synthesis* (M. J. Gait, ed., IRL Press, 1992); *Nucleic Acid Hybridization: A Practical Approach*, (S. J. Higgins and B. D. Hames, eds., IRL Press, 1991); *Transcription and Translation: A Practical Approach*, (S. J. Higgins & B. D. Hames, eds., IRL Press, 1996); R. I. Freshney, *Culture of Animal Cells: A Manual of Basic Technique*, 4$^{th}$ Edition (Wiley-Liss, 1986); and B. Perbal, *A Practical Guide To Molecular Cloning*, 2$^{nd}$ *Edition*, (John Wiley & Sons, 1988); and *Current Protocols in Molecular Biology* (Ausubel et al., eds., John Wiley & Sons), which is regularly and periodically updated.

A wide variety of vectors are known that have use in the invention. Suitable vectors include plasmid vectors, viral vectors, including retrovirus vectors (e.g., see Miller et al., *Methods of Enzymology*, 217:581-599 (1993)), adenovirus vectors (e.g., see Erzurum, et al. *Nucleic Acids Res.*, 21:1607-1612 (1993); Zabner, et al., *Nature Genetics*, 6:75-83 (1994); and Davidson, et al., *Nature Genetics*, 3:219-223 (1993)) adeno-associated virus vectors (e.g., see Flotte, et al., *PNAS* 90:10613-10617 (1993)), herpesvirus vectors (e.g., see Anderson, et al., *Cell Mol. Neurobiol.*, 13:503-515 (1993)), and lentivirus vectors (e.g., see Lever, *Curr. Opin. Mol. Ther.*, 2:488-496 (2000)). The vectors may include other known genetic elements necessary or desirable for efficient expression of the nucleic acid in a specified host cell, such as the transgenic fish host cells described herein, including regulatory elements. For example, the vectors may include a promoter, including one that is specific to organ- or tissue-specific (e.g., specific to lymphoid tissue) as described herein and any necessary enhancer sequences that cooperate with the promoter to achieve transcription of the gene. By "enhancer" is meant nucleotide sequence elements which can stimulate promoter activity in a cell, such as a transgenic fish host cell described herein. The vectors may be in, for example, a linearized form.

The oncogene nucleotide sequence may also be fused to a nucleotide sequence encoding a reporter gene product so that a fusion protein will be formed, and whose presence and or location may be visualized or otherwise identified. The terms "encoding" and "coding" refer to the process by which a nucleotide sequence, through the mechanisms of transcription and translation, provides the information to a cell from which a series of amino acids can be assembled into a specific amino acid sequence to produce a polypeptide. As one example of such a nucleotide sequence, a nucleotide sequence encoding GFP may be advantageously utilized in the invention so that areas of the developing embryo and/or hatched or otherwise mature fish will fluoresce upon expression of the fusion protein. Alternatively, other reporter gene products may be utilized, including luciferase, β-galactosidase, chloramphenicol acytransferase, β-glucuronidase and alkaline phosphatase. Assays for determining the presence, and including determining the activity or amount, of the reporter gene products described herein are known to the art and are discussed in, for example, *Current Protocols in Molecular Biology* (Ausubel et al., eds., John Wiley & Sons), which is regularly and periodically updated. Further descriptions of assays for the reporter gene products discussed herein may be found, for example, in the following publications: for luciferase, see Nguyen, V. T. et al., *Anal. Biochem.* 171:404-408 (1988); for β-galactosidase, see, e.g., Martin, C. S., et al., in *Bioluminescence and Chemiluminescence: Molecular Reporting with Photons* pp. 525-528 (J. W. Hastings, et al., eds., John Wiley & Sons, 1997); Jain, V. K. and Magrath, I. T., *Anal. Biochem.* 199:119-124 (1991); for β-galactosidase, β-glucuronidase and alkaline phosphatase see, for example, Bronstein, I. et al., in *Biolumunescence and Chemiluminescence: Fundamentals and Applied Aspects*, pp. 20-23, (A. K. Campbell, et al., eds., John Wiley & Sons, 1994); for chloramphenical acetyltransferase, see Cullen, B., *Methods. Enzymol.* 152:684 (1987); Gorman, C. et al. *Mol. Cell. Biol* 2:1044 (1982); Miner, J. N. et al., *J. Virol.* 62:297-304 (1988); Sleigh, M. J., *Anal. Biochem* 156:251-256 (1986); Hruby, D. E. and Wilson, E. M., Methods Enzymol. 216:369-376 (1992).

Figure 5:
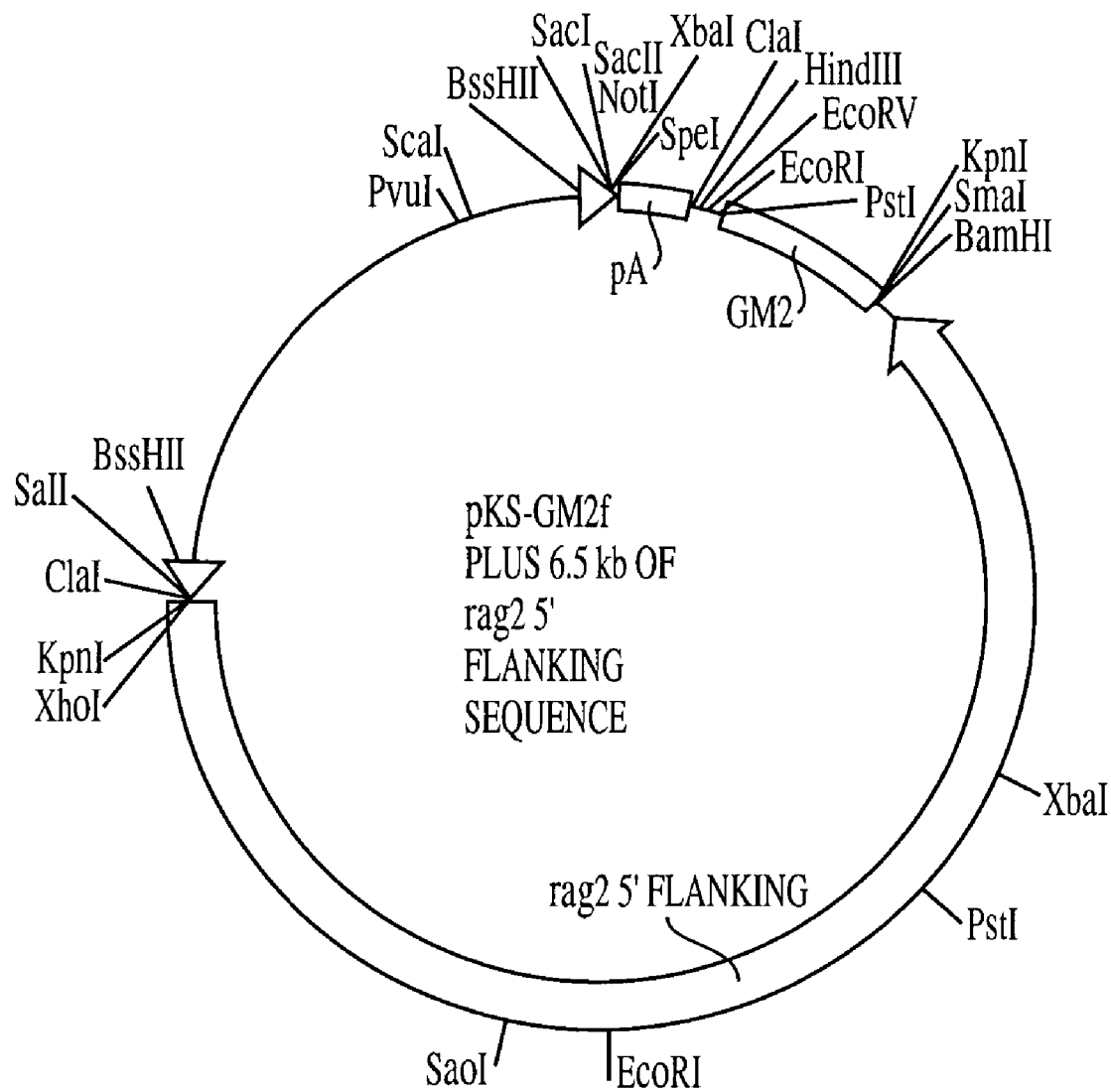
FIG. 5.

An example of a suitable plasmid vector including a murine cMYC-encoding nucleotide sequence and a GFP-encoding nucleotide sequence (Yi et al., 2001) regulated by the zebrafish RAG2 promoter that may be used in the invention to produce an oncogene-green fluorescent fusion protein is shown in FIG. 5. This fusion construct induced lymphoma in zebrafish in a similar manner as cMYC alone. Other oncogenes that may be directed to specific organs or tissues, such as lymphoid tissues, by specific promoters and fused to GFP include members of the activated-RAS, BCL2, HOX11, HOX11L2, LMO1, LMO2, and TAL1/SCL gene families. As described herein, other reporter genes well known to those of skill in the art may also be used for oncogene fusions.

In yet another aspect of the invention, the oncogene is preceded by a reporter gene, such as a fluorescent protein gene (e.g., GFP, RFP, BFP, YFP, or dsRED2) or a luciferase protein gene, comprising a strong transcriptional stop-site, which is flanked by site specific recombinase recognition sites (e.g., Flox, Lox, or FRT-sites). A ubiquitous gene promoter (e.g., EF1-alpha or beta-actin) may drive expression of the "Loxed," "Floxed" or "FRPed" reporter gene. A second gene product (e.g., an oncogene) is adjacent to the reporter gene but is not expressed in the absence of recombinase protein expression because of the strong transcription stop-site within reporter gene. However, when the recombinase protein expression is activated in the cells, the Loxed, Floxed, or FRPed reporter gene product is excised, and the second gene is juxtaposed to the ubiquitous gene promoter. Additionally, tissue-specific recombination may be facilitated by laser-activation of a heat-shock inducible site-specific recombinase transgene through use of a laser. Laser activation may be targeted to individual cells during embryologic development. This transgenic strategy not only prevents toxicity to the parental cells harboring the oncogene, but also allows the use of two transgenic fish lines to create a wide variety of cancer models, which express the same oncogene. For example, the MYC oncogene is misregulated in T-cell leukemia/lymphoma, Burkitt's and other non-Hodgkin's lymphoma, pancreatic beta cell tumors, invasive islet adenocarcinoma, renal cell carcinoma, ovarian cancer, Acute Myeloid Leukemia, colon carcinoma, glioblastomas, and melanoma. Thus, all of these diseases may be modeled using the strategy described herein.

In yet another aspect of the invention, methods of making a transgenic fish are provided herein. In one embodiment, a method includes introducing into a fertilized fish egg (i.e., including a fish embryo) or an unfertilized fish egg nucleic acid including a mammalian oncogene operably linked to a promoter. The nucleic acid may be part of a vector described herein. When a fertilized fish egg is used, the method includes developing the fish embryo into a transgenic fish. When the oncogene is introduced into a non-fertilized egg, the method includes fertilizing the egg and developing the fish embryo into a transgenic fish. The nucleic acid construct may be introduced into the egg by a variety of methods known to the art, including mechanical methods, chemical methods, lipophilic methods, retroviral infection methods, and electroporation. Exemplary mechanical methods include, for example, microinjection. Exemplary chemical methods include, for example, use of calcium phosphate or DEAE-Dextran. Exemplary lipophilic methods include use of liposomes and other cationic agents for lipid-mediated transfection. Such methods are generally well known to the art and many of such methods are described in, for example, *Gene Transfer Methods: Introducing DNA into Living Cells and Organisms*, (P. A. Norton and L. F. Steel, eds., Biotechniques Press, 2000); and *Current Protocols in Molecular Biology* (Ausubel et al., eds., John Wiley & Sons), which is regularly and periodically updated. Microinjection techniques involving fish are further more fully described in, for example, Chen, T. T. and Powers, D. A., *Trends. Biotechnol.* 8:209-215 (1990) and Fletcher, G. L., and Davis, P. L., *Transgenic fish for aquaculture*, in *Genetic Engineering* (Setlow, J. K., ed., Plenum Press, 1991). Electroporation techniques involving fish are further more fully described in, for example, Powers, D. A., et al., *Molec. Mar. Biol. Biotechnol.* 1:301-308 (1992) and Lu, J. K., et al., *Molec. Mar. Biol. Biotechnol.* 1:366-375 (1992). Techniques for introducing DNA into fish eggs or embryos by infection with retroviral vectors, such as pantropic retroviral vectors, are further described in, for example, Burns, J. C., et al., *Proc. Natl. Acad. Sci. USA* 90:8033-8037 (1993).

The vector or other nucleic acid comprising the transgene may be introduced into an unfertilized egg or a fertilized egg at a desired stage of development. Multiple vectors, each encoding different transgenes as described herein may be used. When using a fertilized egg, or embryo, it is preferred to introduce the nucleic acid into the embryo (i.e., at the one-cell stage of development). However, the nucleic acid may also be administered at later stages of development, including the two-cell stage, four-cell stage, etc. Therefore, the nucleic acid may be introduced into the morula, blastula, etc. At least one isolated nucleic acid molecule incorporating the above-described transgenic construct is introduced into the zygote. Additionally, when the nucleic acid is introduced into an egg at later stages of development, at least one isolated nucleic acid molecule incorporating the above-described transgenic construct is introduced into at least one cell of the, for example, morula, blastula, etc.

Fish eggs may be obtained from the appropriate fish by standard methods. Many of the fish may be purchased commercially from, for example, pet stores. Fertilized eggs may be obtained by methods known to the art. For example, a desired number of appropriately aged fish, such as about three to about twelve month old fish, with a desired ratio of females to males (such as about 2:1) may be placed in an appropriately sized container, such as a tank. Eggs may be collected by, for example, placing the fish in a nuptial chamber in the tank for an appropriate time after mating, such as about 10 to 60 minutes. Such methods are described in, for example, Culp, P. et al., *Proc. Natl. Acad. Sci.* 88:7953-7957 (1991). Alternatively, fish eggs may be artificially fertilized by methods known to the skilled artisan. One skilled in the art is familiar with other methods of obtaining such fertilized fish eggs.

After introducing the nucleic acid construct into the fish egg or embryo, the fish egg or embryo is provided with an environment conducive to development into an adult fish. Such an environment may include, for example, growth at 28.5° C. in E3 egg water for 15 days followed by introduction into circulating system water by day 16 (*The Zebrafish Book: A Guide For the Laboratory Use of Xebrafish (Danio rerio)*, 4$^{th}$ Ed. (M. Westerfield ed., University of Oregon Press, Eugene, Oreg. (2000)).

Transgenic fish produced as described herein may be identified by common procedures known to the art, including dot blot and Southern blot hybridization of genomic DNA. Briefly, such methods involve isolation of genomic DNA from tissues of the fish, digestion of DNA with restriction enzymes and Southern blot hybridization of the digested DNA products as described in, for example, Chen, T. T. et al., *Biotech. Ann. Rev.* 2:205-236 (1996). A preliminary screen may be accomplished by isolating genomic DNA from a piece of fin tissue, amplifying the transgenic sequence by the polymerase chain reaction and Southern blot analysis of the amplified products as described in Lu, J. K. et al., *Molec. Mar. Biol. Biotechnol* 1:366-375 (1992) and Chen, T. T. et al., *Molec. Mar. Biol. Biotechnol.* 2:88-95 (1993). Additionally, if an oncogene-fluorescent fusion protein, including an oncogene-GFP fusion protein, is encoded by the introduced nucleic acid, a visual preliminary screen for fluorescence may be used.

The transgenic fish produced preferably has the transgene stably integrated into its genome. This means that the transgene is integrated into the genome of the fish as opposed to being extrachromosomal. It is additionally preferred that the transgene is found in germ cells and in B- and/or T-cell progenitors or other organ- or tissue-specific cells of the fish. The presence of the transgene in the germ cells allows for transmission of the transgene to subsequent generations. In certain embodiments, it is preferred that the transgene is expressed in the B- or T-cell progenitors so the fish will develop a lymphoma or leukemia. In one embodiment, the transgene is expressed in T-cell progenitors so that fish develop a T-cell lymphoblastic leukemia, such as T-cell acute lymphoblastic leukemia. In other embodiments, the fish develop B-cell lymphoma and leukemias, myeloid leukemias, nervous system tumors (e.g., brain tumors), melanoma, bowel tumors, pancreatic tumors, skin tumors, muscle sarcomas, germ cell tumors, ovarian carcinomas, or other tumors or cancers well known by those of skill in the art. Such an animal may thus advantageously be used as a model for cancer, including, for example, as a model for T-cell acute lymphoblastic leukemia. Accordingly, methods of screening for drugs or agents for modulating oncogene-mediated neoplastic or hyperplastic transformation, as well as the sensitivity of transgenic cells to treatments with radiation or chemotherapy, are provided.

In another aspect of the invention, methods of making a stable transgenic fish model of human cancers are provided, wherein an oncogene can be regulated in any tissue by using regulatable site-specific recombinases. In one embodiment, a method includes: (a) producing a first transgenic fish whose genome has stably-integrated therein a first transgene cassette comprising a Floxed, Loxed, or FRPed reporter gene (e.g., a fluorescent protein gene or luciferase), comprising a strong transcription stop-site, wherein said reporter gene is regulated by a ubiquitous gene promoter (e.g., beta-actin or EF1-alpha), and an oncogene placed immediately after the reporter gene; (b) producing a second transgenic fish whose genome has stably-integrated therein a second transgene cassette comprising a flip or cre-recombinase (CRE) gene operably linked to a heat shock inducible promoter (e.g., HSP-70); (c) mating said first transgenic fish with said second transgenic fish to produce offspring, which co-express said reporter gene and said flip or CRE gene; (d) laser-activating the heat-shock inducible CRE transgene in single cells of the body causing recombination of the first transgenic cassette, wherein the reporter gene is excised and the ubiquitous gene promoter is juxtaposed adjacent to the oncogene.

In another aspect, a method of screening for drugs or agents that modulate oncogene-mediated, or otherwise induced, neoplastic or hyperplastic transformation, or that modulate the sensitivity of transgenic cells to treatments with radiation or chemotherapy, is provided. A method comprises (a) contacting or otherwise exposing a transgenic fish (e.g., an adult transgenic fish or a transgenic fish embryo) described herein with a test drug or agent, wherein the genome of the transgenic fish has stably integrated therein nucleic acid comprising an oncogene operably linked to a promoter; (b) determining if the test drug or agent suppresses or enhances oncogene-mediated neoplastic or hyperplastic transformation, or modulates the sensitivity of transgenic cells to treatments with radiation or chemotherapy; and (c) classifying the test drug or agent as a drug or agent that modulates oncogene-mediated neoplastic or hyperplastic transformation, or that modulates the sensitivity of transgenic cells to treatments with radiation or chemotherapy, if the test drug or agent suppresses or enhances oncogene-mediated neoplastic or hyperplastic transformation or modulates the sensitivity of transgenic cells to treatments with radiation or chemotherapy. As mentioned herein, the modulation may include suppressing, or otherwise decreasing, or enhancing, or otherwise stimulating, oncogene-mediated neoplastic or hyperplastic transformation, including the rate of oncogene-mediated neoplastic or hyperplastic transformation, or sensitivity of transgenic cells to treatments with radiation or chemotherapy.

The test drug or agent is typically identified from a large-scale, robotically-driven screen of thousands of compounds to identify a drug or agent thought to have the ability to modulate oncogene-mediated neoplastic or hyperplastic transformation, or modulate the sensitivity of transgenic cells to treatments with radiation or chemotherapy. Such screens are routine, and these, and other screening methods, are well known by those of skill in the art. The test drug or agent may suppress, or otherwise alter, or enhance expression of oncogene RNA and/or the oncogenic protein product, or RNA or protein expression of other genes involved in the oncogenic transformation process. Additionally, the test drug or agent may inhibit or stimulate the activity of other molecules involved, directly or indirectly, in the neoplastic/hyperplastic transformation process, or in the sensitivity of transgenic cells to treatments with radiation or chemotherapy. A wide variety of drugs or agents may be tested in the screening methods of the present invention. For example, small molecule compounds similar to those identified in Peterson, R. T., et al., *Proc. Natl. Acad. Sci. U.S.A*, 97: 12965-12969, (2000) and Peterson, R. T., et al. *Curr. Biol.*, 11: 1481-1491, (2001) or a panel of FDA approved chemicals may be assayed. Small molecule compounds are identified by screening large chemical libraries for the effects of compound addition to the water of developing fish. Additionally, proteins such as oligo- and polypeptides, may also act as test drugs or agents.

Further examples of such test drugs or agents include oligonucleotides or polynucleotides, such as, for example, antisense deoxyribonucleic acid (DNA), antisense ribonucleic acid (RNA), and small interfering RNAs. The antisense nucleotide sequences typically include a nucleotide sequence that is complementary to, or is otherwise able to hybridize with, a portion of the target nucleotide sequence, such as the target nucleotide sequences described herein and including the cMYC target nucleotide sequences (GenBank Accession No. XM_122917.1) and others described herein. The antisense nucleotide sequence may have a length of at least about 10 nucleotides, but may range in length from about 10 to about 1000 nucleotides, or may be the entire length of the gene target. The skilled artisan can select an appropriate target and an appropriate length of antisense nucleic acid in order to have the desired therapeutic effect by standard procedures known to the art, and as described, for example, in *Methods in Enzymology, Antisense Technology*, Parts A and B (Volumes 313 and 314) (M. Phillips, ed., Academic Press, 1999).

RNA interference relates to sequence-specific, post-transcriptional gene silencing brought about by double-stranded RNA that is homologous to the silenced gene target (Lee et al., *Nature Biotech.* 19:500-505 (2002)). Such a method may be used to prevent production of an oncogenic protein. Methods for inhibiting production of a protein utilizing small interfering RNAs are well known to the art, and disclosed in, for example, PCT International Application Numbers WO 01/75164; WO 00/63364; WO 01/92513; WO 00/44895; and WO 99/32619.

The test drugs or agents are typically administered in an amount and for a time necessary to suppress, or otherwise alter, or enhance oncogene-mediated neoplastic or hyperplastic transformation. Such amounts and times may be determined by the skilled artisan by known standard procedures.

Transgenic fish are typically contacted with the test drug or agent at a desired time after hatching. In other forms of the invention, the fish embryo contained with the fish egg may be contacted with the test drug or agent.

In one embodiment of the invention, determining if the test drug or agent suppresses, or otherwise alters, or enhances oncogene-mediated neoplastic or hyperplastic transformation may be performed by measuring the amount and/or size of tumors formed in the fish and/or measuring the rate of onset of tumor formation. Other indicators of oncogene-mediated, or otherwise induced, neoplastic or hyperplastic transformation, or modulation of the sensitivity of transgenic cells to treatments with radiation or chemotherapy, may also be measured. For example, when reporter gene-oncogene fusion constructs are used, reporter gene expression may be determined using methods well known by those of skill in the art and as described herein. For instance, utilizing a tissue-specific promoter operably linked to a GFP-oncogene fusion construct will permit GFP fluorescence emitted from the protein specifically expressed in a particular tissue to be determined. Additional visual or other screens for metastatic tumors may also be used.

In some embodiments of the invention, the oncogene is a member of the MYC or BCL2 gene families, and the promoter is a RAG2 promoter. In other embodiments, the oncogene is substantially similar to, or a mammalian homologue of, MYC or BCL2.

In yet another form of the invention, methods of identifying mutations that modulate (i.e., enhance, suppress, or otherwise alter) oncogene-mediated, or otherwise induced, neoplastic or hyperplastic transformation, such as the rate of onset of neoplastic or hyperplastic growth, including malignant tumors, are provided. In one form, a method involves use of genetic modifier screens. Such screens take advantage of the forward genetic capabilities of the transgenic fish described herein. Mutations that enhance the rate of onset of malignant tumors may be found, for example, in tumor suppressor genes, oncogenes or other genes involved in the neoplastic or hyperplastic process. Other mutations that alter genomic stability may also enhance the rate of onset of malignant tumors.

Mutations that suppress the rate of onset of neoplastic or hyperplastic growth include, for example, proteins required for the malignant phenotype, including proteins that have not yet been identified.

In one embodiment, a method of identifying a mutation that modulates oncogene-mediated neoplastic or hyperplastic transformation includes identifying a mutation in a gene involved in the neoplastic or hyperplastic transformation process, such as a tumor suppressor gene or oncogene. Such genes may be known or unknown, and thus such methods can lead to the discovery of new tumor suppressor genes, oncogenes or other genes involved in the neoplastic or hyperplastic transformation process. In one embodiment, a mutagenized fish is crossed, or otherwise mated, with a non-mutagenized transgenic fish prone to developing cancer as described herein, to produce $F_1$ offspring. The method includes obtaining eggs from $F_1$ females, fertilizing the eggs with inactivated sperm to produce $F_2$ progeny and examining the rate of onset and extent of hyperplasia, such as thymic hyperplasia, to identify $F_1$ fish that exhibit inactivation of a tumor suppressor gene. The method then includes identifying the mutation by methods known to the art.

In specific embodiments, transgenic fish, preferably male, homozygous for the transgene, are mutagenized and mated with a non-mutagenized, female fish homozygous for the transgene. Eggs from $F_1$ females are fertilized with inactivated sperm and subjected to early pressure, such as with a spindle, to produce gynogenetic diploid $F_2$ progeny. The rate of onset and extent of organ or tissue-specific neoplasia or hyperplasia is examined to identify $F_1$ fish that are heterozygous for inactivation of a tumor suppressor gene that accelerates the onset. The $F_1$ female can then be out-crossed to identify the mutation. The mutant allele may then be mapped and the putative tumor suppressor gene identified and cloned by standard methods known to the art.

Figure 6:
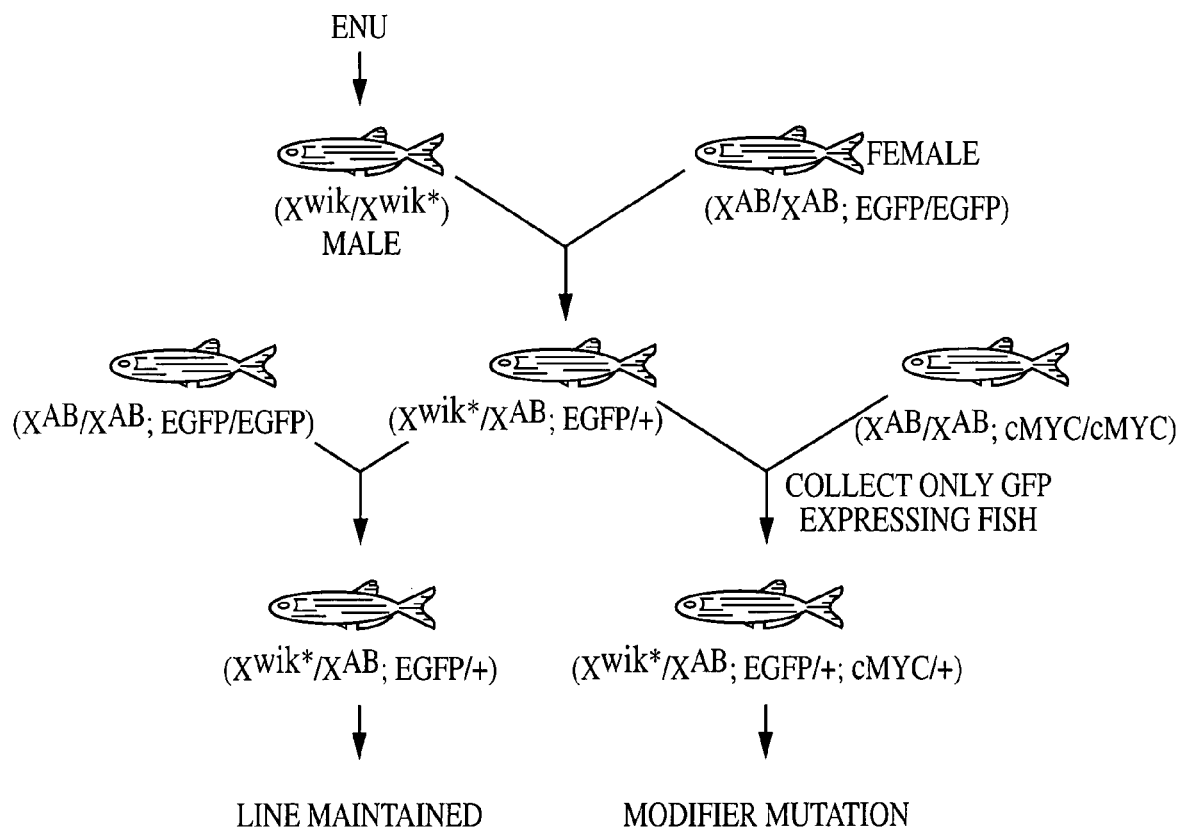
FIG. 6.

In another embodiment, a dominant modifier screen is completed to identify genes involved in increasing, suppressing, or otherwise altering the rate of cancer induced by oncogenes in the transgenic fish described herein. The transgenic fish, as described herein, may comprise any oncogene operably linked to an organ- or tissue-specific promoter, and may or may not further comprise a reporter gene. For example, cMYC function in RAG2-GFP transgenic fish may be analyzed for either accelerated or delayed onset of cancer utilizing this type of screen (FIG. 6). $F_0$ males may be mutagenized with, for example, ENU to create point mutations within the genome of the fish. These fish may then be crossed to homozygous RAG2-GFP female fish to create $F_1$ fish that are heterozygous for both the point mutations and the RAG2-GFP transgene. These fish may then be crossed to homozygous RAG2-cMYC transgenic fish and the resulting $F_2$ progeny can then be analyzed using methods well known by those of skill in the art. For example, GFP-positive fish may be scored for the onset of disease based on visualization of tumor formation by fluorescence microscopy manifested by enlargement of the thymus or metastatic tumor formation in the gills, head region, and/or body musculature. While GFP expression in the T-cells is not required, it would aid in identifying early onset of disease, thereby decreasing the time needed to screen $F_2$ fish.

In another aspect, a method of identifying mutations that modulate sensitivity to radiation- or chemotherapy-induced programmed cell death is provided. In specific embodiments, a method comprises mutagenizing a transgenic zebrafish whose genome has stably-integrated therein a mouse cMYC oncogene operably linked to a zebrafish RAG2 promoter. The transgenic zebrafish is mated with a non-mutagenized zebrafish to produce $F_1$ offspring. Eggs from the $F_1$ offspring are fertilized with inactivated sperm to produce $F_2$ offspring, and the presence and extent of sensitivity to radiation- or chemotherapy-induced programmed cell death in the $F_2$ offspring is determined. The mutation that modulates sensitivity to radiation- or chemotherapy-induced programmed cell death is then identified.

In another specific embodiment, a method comprises mutagenizing male fish comprising the Wik allele to induce a point mutation in the sperm. An AB strain RAG2-EGFP-zBCL2 transgenic female fish is also produced, and the transgenic female fish are mated with the Wik male fish, thereby producing $F_1$ progeny fish heterozygous for the RAG2-EGFP-zBCL2 transgene and having the mutation linked to the Wik allele. Eggs from female $F_1$ progeny fish are fertilized with inactivated wild-type sperm, and early pressure is applied to the fertilized eggs, thereby producing $F_2$ offspring, which express the RAG2-EGFP-zBCL2 transgene and are homozygous for the mutation. The presence and extent of sensitivity to radiation- or chemotherapy-induced programmed cell death is determined in the $F_2$ offspring. $F_2$ heterozygous mutant fish are then incrossed, thereby producing $F_3$ homozygous mutant fish, which comprise the RAG2-EGFP-zBCL2 transgene and are homozygous for the mutation. The mutation in the $F_3$ homozygous mutant fish is then identified that modulates sensitivity to radiation- or chemotherapy-induced programmed cell death.

In yet another specific embodiment, a method comprises mutagenizing male fish comprising the Wik allele to induce a point mutation in the sperm. An AB strain RAG2-EGFP-zBCL2 transgenic female fish is also produced, and the transgenic female fish are mated with the Wik male fish, thereby producing $F_1$ progeny fish heterozygous for the RAG2-EGFP-zBCL2 transgene and having the mutation linked to the Wik allele. The $F_1$ progeny fish are then mated with the AB strain RAG2-EGFP-zBCL2 transgenic fish, and the presence and extent of sensitivity to radiation- or chemotherapy-induced programmed cell death in the $F_2$ offspring is determined. The mutation in the $F_2$ offspring that modulates sensitivity to radiation- or chemotherapy-induced programmed cell death is then identified.

Mutations in the transgenic fish may be induced by a variety of methods, including use of various chemicals, radiation, and/or viral transduction. Such chemicals include, for example, ethylnitrosourea and DMBA. Golling et al. have completed viral mutagenesis screens through use of microinjection and retroviral insertion (*Nat Genet.* 31:135-40 (2002)), and this method may be used in conjunction with the various screens in the transgenic fish described herein. The sperm may be obtained by squeezing males, stimulating release of sperm, or by micro-dissection of testes. The sperm may be inactivated by UV radiation exposure.

Co-expression of two or more oncogenes may lead to accelerated onset of the disease. In the mouse model, for example, misexpression of only TAL1/SCL results in late-onset T-cell acute lymphoblastic leukemia (Kelliher et al., *EMBO J.* 15:5160-5166 (1996); Condorelli et al., *Cancer Res.* 56:5113-5119 (1996)), but when combined with the misexpression of LMO1 or LMO2 will lead to T-cell malignancy with a shorter latency (Larson et al., *EMBO J.* 15:1021-1027; Aplan et al., *EMBO J.* 16:2406-2419 (1997); (Chervinsky et al., *Mol. Cell. Biol.* 19:5025-5035 (1999)). Additionally, mice transgenic for both the Eμ-MYC and Eμ-BCL2 transgenes develop tumors arrested at earlier stages of B-cell development, and develop disease with shortened latency, than those in either Eμ-MYC or Eμ-BCL2 transgenic lines alone (Strasser et al., *Nature*, 348:331-333 (1990)).

Cooperating mutations in the development of malignancy are common in most tumors and are typically required for cancer development.

Thus, in one embodiment, effects of oncogene co-expression are tested directly by crossing transgenic fish (e.g., zebrafish) lines, as described herein, that express different oncogenes in a specific organ or tissue. Each different oncogene may be operably linked to a reporter gene, as described herein. For example, homozygous RAG2-MYC or RAG2-cMYC fish may be crossed with homozygous RAG2-EGFP-BCL2 lines. The progeny may be analyzed for early onset of disease based on, e.g., aberrant growth of GFP positive T-cells in the thymus. Other examples may include mating RAG2-MYC fish with transgenic fish comprising an oncogene of the RAS, HOX11, Hox11L2, LMO1, LMO2 or SCL gene families. The outcome of such co-expression will be evident in the resultant offspring, which may be analyzed, depending on the target tissue or organ, using methods described herein and well known by those skilled in the art. For example, if transgenic fish expressing T-cell specific oncogenes are crossed, the offspring may be analyzed, for, e.g., expanding populations of GFP-positive cells, T-cell histopathology, misexpression of T-cell oncogenes (e.g., by in situ hybridization), and the presence of thymus-specific molecular markers. The rapidity of onset may be determined in cohorts of at least about 50 singly or doubly transgenic animals, as evidence for genetic cooperatively in T-cell acute lymphoblastic leukemia pathogenesis. The animals may be examined daily for the time of onset of thymic enlargement and morbidity/mortality. The survival data may then be analyzed using well-known statistical methods to assess whether the onset of disease and mortality is significantly shortened in doubly transgenic fish lines.

Reference will now be made to specific examples illustrating the transgenic fish and methods described above. It is to be understood that the examples are provided to illustrate preferred embodiments and that no limitation to the scope of the invention is intended thereby.

EXAMPLE 1

RAG2-MYC Transgenic Models of T-c II Leukemia

Translocation of cMYC gene into the T-cell receptor locus or immunoglobulin enhancer region causes dysregulation of the cMYC gene and results in malignant transformation of T- and B- cells in T-cell acute lymphoblastic leukemia and B-cell non-Hodgkin's lymphoma. Given that zebrafish are amenable to genetic screens, develop rapidly ex-utero, are transparent for much of their life cycle, and produce large clutches of offspring each week, zebrafish serve as an ideal model to study conserved pathways that lead to MYC-induced cancer progression in vertebrates. This example describes production of a zebrafish model of T-cell acute lymphoblastic leukemia, wherein mouse-cMYC was targeted to the T-cell progenitors in mosaic (or chimeric) $F_0$ fish, and in a stable line of zebrafish in which the progeny express and transmit to their offspring a EGFP-mMYC transgene.

Mouse cMYC and EGFP-mMYC fusion proteins were targeted to the T-cell progenitors in the developing zebrafish (Yin et al., *Oncogene*, 20: 4650-4664 (2001)) through use of the zebrafish RAG2 promoter. The MYC family of proteins is highly evolutionarily and functionally conserved across species (Schreiber-Agus et al., *Mol. Cell Biol.*, 13: 2765-2775 (1993); Schreiber-Agus et al., Proc. Natl. Acad. Sci. U.S.A, 94: 1235-1240 (1997); Yuan et al., *Oncogene,* 17: 1109-1118 (1998)). For example, zebrafish cMYC-I (Schreiber-Agus et al., *Mol. Cell Biol.*, 13: 2765-2775 (1993) and *Drosophila* MYC (Schreiber-Agus et al., Proc. Natl. Acad. Sci. U.S.A, 94: 1235-1240 (1997)) are capable of cooperating with activated H-RAS to effect the malignant transformation of mammalian cells, indicating that these proteins are functionally similar across phyla and that cMYC proteins from different species have similar transformation properties when placed into human cell lines.

A. Materials and Methods

1. DNA Constructs

The RAG2-GM2 plasmid was digested at 37° C. with BamH1 and HindIII overnight to release the GM2 cassette. The enzyme digest mix containing the linearized plasmid vector was heat-inactivated at 80° C., cooled to 4° C., and phosphorylated overnight with alkaline phosphatase at 37° C. The following day, the reaction was heat-inactivated and stored at 4° C. until use.

mcMYC and EGFP-mcMYC were ligated into the linearized RAG2-vector. Specifically, PCR was used to amplify the mouse cMYC open reading frame. The forward PCR primers contained a 6 bp leader sequence (AATTCC) followed by a BamH1 and Sma1 cloning site, 6 bp 5' the ATG start site (presumably specifying the Kozak sequence) and 17 bp of coding sequence, including the ATG start site. The reverse primers contained 6 bp of leader sequence, a HindIII cloning site, and 24 bp of coding sequence, including the termination codon sequence. PCR-amplified fragments were digested overnight with BamH1 and HindIII at 37° C. and resolved on an ethidium bromide-containing agarose gel (1% in 1×TBE). Gel bands were excised and DNA extracted by QIAGEN QIAquick® gel extraction kit (QIAGEN, Valencia, Calif.). The DNA was ligated into the linearized RAG2 vector overnight at 4° C. and used for transformation into competent JM109 bacteria cells (Promega, Madison, Wis.). Cells were grown on ampicillin-containing agarose plates, and positive clones were identified by colony PCR using cMYC-specific primers. Positive clones were grown in LB+ampicillin overnight, and the plasmid prepped (Wizard® SV Minipreps, Promega, Madison, Wis.).

RAG2-EGFP-MYC constructs were made using linker-mediated ligation. Specifically, the EGFP-MYC vector was digested with Nhe1 and EcoR1 to release the portion of the vector containing the EGFP-MYC coding sequence. This fragment was ligated into the linearized, alkaline phosphatase-treated PCS2 vector, (digested with BamH1 and EcoR1) in the presence of a phosphorlyated double strand linker. The linker adapted the BamH1 overhangs from the PCS2 vector into Nhe1 compatible ends. These PCS2-EGFP-MYC vectors were digested with BamH1 and HindIIII, to release the coding sequence and ligated into the linear RAG2-construct as above. Both of these methods for cloning into the RAG2 vector are methods well known by those of skill in the art.

Additionally, a RAG2-human MYC-ER construct was created using a PCR based cloning strategy (as above). The MYC-ER transgene is a fusion between the human cMYC gene and a portion of the estrogen receptor (ER) responsible for binding estrogen. This fusion transgene has been reported to be conditionally activated in mice. In the absence of tamoxifen (an estrogen analog), MYC-ER is retained in the cytoplasm and is not functional. In the presence of tamoxifen, MYC-ER translocates to the nucleus where it is able to activate genes involved in MYC-induced transformation. Tamoxifen may be administered to mice in their drinking water and results in the activation of the MYC-ER allele. A similar transgenic system may also be use in fish, wherein the addition of tamoxifen to the water will activate the MYC-ER alleles in transgenic fish.

Figure 7A:
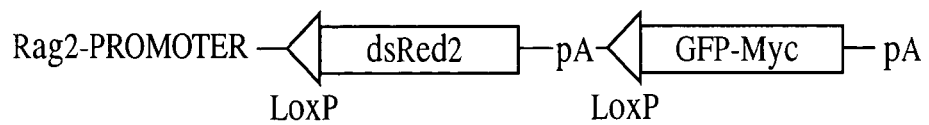
FIG. 7.
Figure 7B:
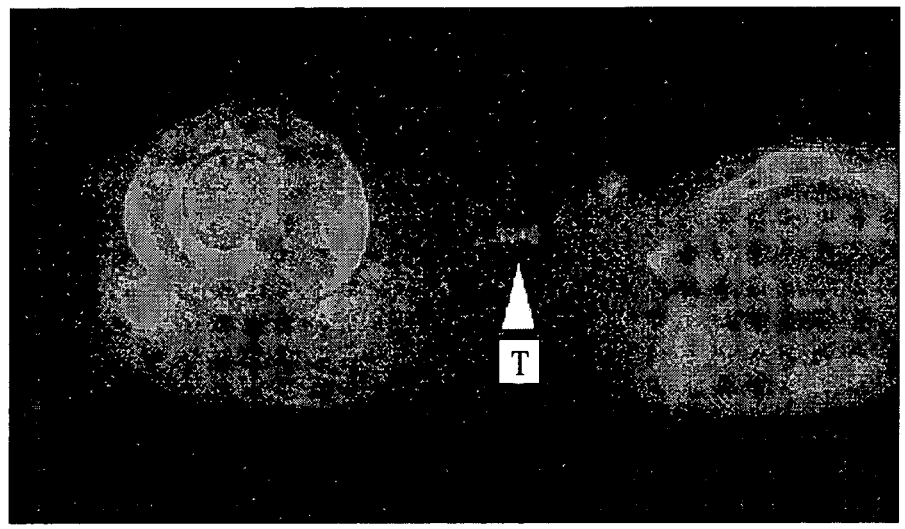
Figure 7C:
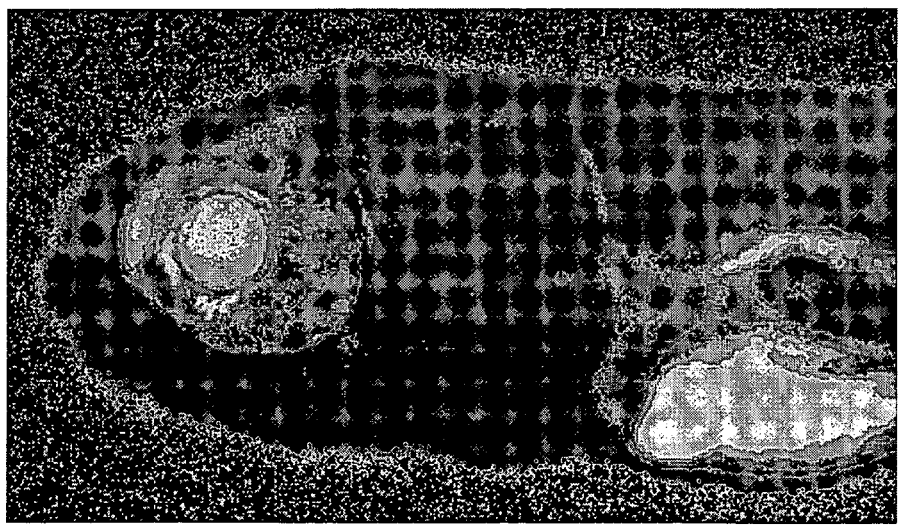
Figure 8A:
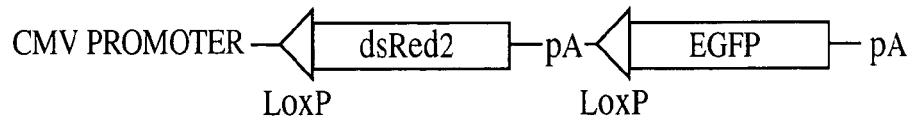
FIG. 8.
Figure 8B:
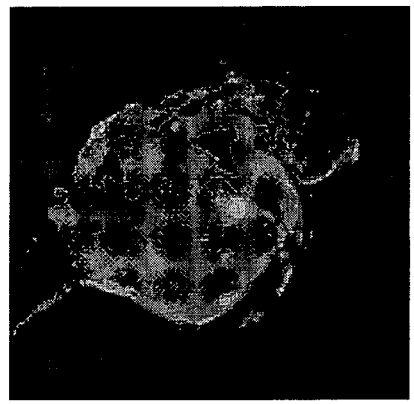
Figure 8C:
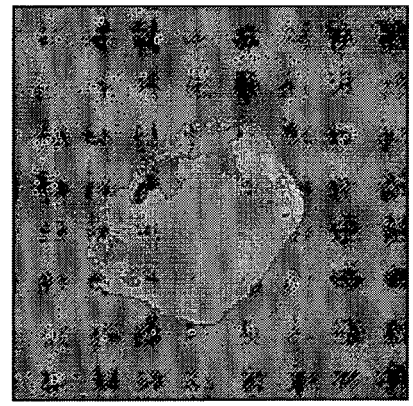
Figure 8D:
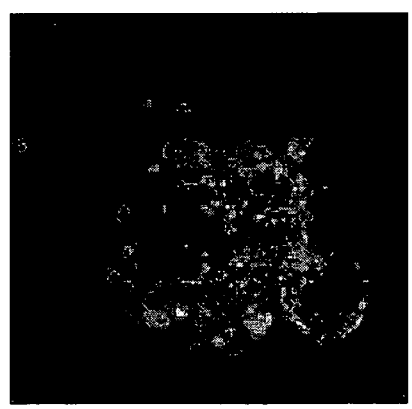
Figure 8E:
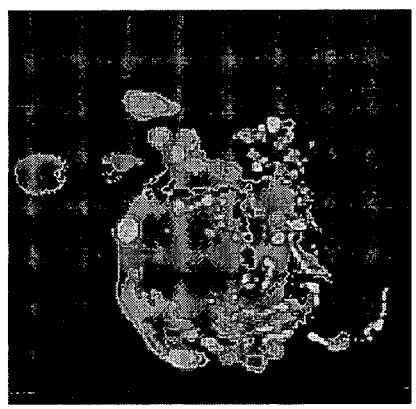

Finally, a loxed dsRED2 allele was cloned into the RAG2-EGFP-mMYC plasmid at the BamH1 site, upstream of the EGFP-mMYC transgene. The resulting RAG2-Lox-dsRED2-EGFP-mMYC plasmid contains lox sites which flank the dsRED2 transgene (FIG. 7A). In the absence of CRE recombinase, the dsRED2 transgene is expressed, while the EGFP-mMYC transgene is not active (FIG. 7.B-7.C). In the presence of CRE-recombinase activity, the dsRED2 allele will be excised placing the RAG2-promoter adjacent to the EGFP-mMYC transgene. This will result in expression of EGFP-mMYC in thymic progenitors, leading to the development of T-cell Leukemia/lymphoma in transgenic fish.

To verify that this CRE/Lox-mediated strategy worked in fish, we created an expression vector which expresses the dsRED2 loxed allele under control of the ubiquitous expressing CMV promoter containing the EGFP transgene (FIG. 8.A). The resulting plasmid contains lox sites that flank the dsRED2 transgene (as outlined above), which lies upstream of a EGFP transgene. As in the RAG2-Lox-dsRED2-EGFP-mMYC, dsRED2 is expressed in the absence of CRE induction, while EGFP expression is silenced. Upon CRE-induction, the dsRED2 allele is excised, juxtaposing the CMV promoter next to the EGFP transgene. This results in expression of GFP following CRE-mediated recombination. A vector containing CMV promoter driving expression of CRE was also established to deliver CRE recombinase activity to embryos during early development (PCS2+CRE).

2. Embryo Injections: Transient Analysis of CRE Recombination in Fish.

To verify that the CRE-recombinase strategy works in the zebrafish, we co-injected the CMV-lox-dsRED2-EGFP plasmid with either the PCS2+CRE plasmid DNA or with the CRE mRNA made from this plasmid. Specifically, the PCS2+CRE vector was linearized by Not1 digestion overnight, and the resulting cleaved DNA was phenol:chloroform/ethanol precipitated. Because the PCS2+ vector contains an Sp6 promoter site 5' of the CRE transcription start site, we were able to make CRE RNA using an SP6 RNA polymerase. RNA was purified using a lithium chloride extraction and resuspended to a final concentration of 200 ng/microliter.

For DNA:DNA injections, a solution containing 50 ng/microliter of CMV-lox-dsRED2-EGFP plasmid and 50 ng/microliter of PCS2+CRE plasmid was injected into embryos at the one-cell stage of development. For DNA:RNA injections, a solution containing 25 ng/microliter of CMV-lox-dsRED2-EGFP plasmid was injected with 50 ng of CRE RNA. Embryos were analyzed at 24 and 48 hours for expression of GFP and dsRED2 as determined by fluorescent microscopy.

3. Embryo Injections: Creation of Mosaic Founder Fish and Stable Transgenic Lines.

RAG2-cMYC, RAG2-EGFP-MYC, RAG2-hMYC-ER, and RAG2-lox-dsRED2-EGFP-mMYC vectors were linearized by digestion with Xho1 or Not1 at 37° C. overnight, and DNA was purified by phenol:chloroform extraction followed by ethanol precipitation. DNA concentration was assessed by both UV spectrophotometry and gel quantification. Linearized DNA was diluted to 100-200 ng/microliter in 0.5×TE/100 mM KCl and injected into wild-type AB embryos at the one-cell stage of development using a glass micropipette. The volume of DNA injected was tittered to a point at which 20-50% of the embryos exhibited morphological features associated with over-injection of DNA. This is commonly seen in microinjection into zebrafish and ensures that surviving embryos have high levels of DNA integration into cells. The 20-50% of embryos exhibiting "monster" morphology were discarded. Embryos were grown in E3 egg water at 28.5° C. until 15 days of development, at which time they were placed into our re-circulating system. These $F_0$ mosaic fish were analyzed daily for onset of tumors based on external morphologic features, which are characteristic of lymphoma, including thymic enlargement (protrusion of the thymus from the opercul), and tumor formation in the eyes or head.

Microinjection of RAG2-cMYC was also completed in AB embryos heterozygous for the RAG2-GFP to visualize tumor formation by fluorescence microscopy. RAG2-GFP stable transgenic lines had been established previously. Tumor onset was assessed by aberrant expression of GFP within mosaic RAG2-mcMYC fish by fluorescence microscopy once each week.

4. Histological Methods.

Tumorigenic fish and AB control fish were analyzed histologically. Fish were fixed in 4% paraformaldehyde at 4° C. overnight and processed for embedding in paraffin. Methods for dehydration of tissue samples is well known to those skilled in the art. Fish were cut transversely into 5-10 mm sections and embedded in paraffin. Blocks were sectioned at 5-10 microns through the length of the fish and every tenth slide was stained with hematoxylin/eosin. Slides were analyzed by light microscopy for tumor formation as compared to wild-type AB slides.

5. In situ Hybridization.

Methods for RNA in situ hybridization on paraffin embedded slides is well known to those skilled in the art (e.g., Wilcox et al., In situ cDNA:mRNA hybridization: Development of a technique to measure mRNA levels in individual cells. IN: Methods in Enzymology, Vol. 124, Neuroendocrine Peptides (P. M. Conn. Ed.) Academic Press, pp. 510-533 (1986); Rosenthal et al., *EMBO J.* 6:3641-3646 (1987); Wilcox et al., *J. Neurosci.* 8:1901-4. 1988; Wilcox et al., *Mol Cell Biol.* 8:3415-22. (1988), Melton et al., *Nucleic Acids Res.* 12:7035-56 (1984); Maniatis et al., *Molecular Cloning: A Laboratory Manual*, $2^{nd}$ ed., Cold Spring Harbor Laboratory Press, Cold Spring Harbor, N.Y. (1982); and Yang et al., *J Histochem Cytochem.* 47:431-46 (1999)), and was completed with only minor variations. Briefly, cDNA probes were made by PCR of plasmid DNA containing coding sequences for genes of interest, including cMYC, SCL, LMO1, LMO2, RAG1, RAG2, TCRα, LCK, IgLC, and IgM. PCR primers included T7 and Sp6 promoter sequences and were incorporated into the amplified fragments. PCR products were 400-600 bp in length and were purified using the QIAquick® PCR purification kit (QIAGEN, Valencia, Calif.). RNA probes were made using T7 and Sp6 RNA polymerase. Hybridization was carried out, and RNA staining was visualized using peroxidase staining techniques.

6. Southern Analysis.

Southern analysis was completed as described by Haire et al. *Immunogenetics* 51: 915-923 (2000) with some variations. Specifically, genomic DNA was isolated from the posterior portion of the fish. Fish were anesthetized and cut in half transversely at the anus. Genomic DNA from the tail portion of the fish was extracted (PUREGENE™ DNA Isolation Kit, Gentra Systems, Minneapolis, Minn.), quantified by spectrophotometric analysis, and 8 mg of DNA was digested overnight at 37° C. with the BgIII restriction enzyme. DNA fragments were electrophoresed on a 0.8% agarose gel (1×TBE) containing ethidium bromide for 4 hours. DNA was transferred to nylon membranes and the blots were probed with radiolabelled TCRα or IgM probes. These probes were specific to the constant regions of these genes and were made by random-primed labeling (Rediprime™ II, Amersham Biosciences, Piscataway, N.J.). Washing of membranes was completed under high stringency conditions and membranes were exposed to x-Ray film for 1-3 days, after which time they were developed.

7. FACS Analysis.

Kidney cells and spleen cells were isolated from wild-type AB fish or from mosaic RAG2-MYC/EGFP-MYC fish following dissection. Harvested cells were resuspended in 0.9× PBS and 5% FBS, separated by a 40 micron filter, washed, and stained with propidium iodine. FACS was completed based on forward and side-scatter, and in some instances based on GFP fluorescence.

8. Blast Morphology.

Cytospins were completed on whole kidney marrow and whole spleen as well as on FACS sorted cell populations. Cells were stained with May-Grunwald, cover slipped, and viewed under high power.

9. Touch Preps.

Fish were anesthetized and cut in half transversely at the anus. The cut portions of the fish were placed onto glass slides repeatedly (i.e. a 'touch prep'). Slides were dried from several minutes and stained with May-Grunwald as described above.

10. PCR Verification of Transgene Incorporation into Genomic DNA.

Fish were anesthetized and cut in half transversely at the anus. The tail portion was extracted for genomic DNA by either PUREGENE™ protocols (Gentra Systems, Minneapolis, Minn.) or Proteinase-K digestion as outlined in *The Zebrafish Book: A Guide For the Laboratory Use of Xebrafish (Danio rerio)*, $4^{th}$ Ed. (M. Westerfield ed., University of Oregon Press, Eugene, Oreg. (2000)). PCR was completed using primers spanning both the RAG2-promoter and the MYC coding sequence. The forward primer was within the RAG2-promoter sequence while the reverse primer was within the MYC coding sequence. Control primers amplified across the RAG2 promoter and RAG2 open reading frame.

11. DNA Flow Cytometry.

Body musculature obtained from the posterior portion of tumorigenic fish was diced over ice-cold 0.9×PBS and 5% FBS, separated by a 40 micron filter, washed, and stained with propidium iodine. Kidney cells from wild-type fish were harvested by dissection and resuspended in 0.9×PBS and 5% FBS, separated by a 40 micron filter, washed, and stained with propidium iodine. Twenty five hundred cells were analyzed by DNA flow cytometry. Combinations of tumor and wild-type cells verified that peaks identified in tumor samples were 2N or heterodiploid.

12. Semi-Quantitative RT-PCR.

RNA was isolated from RAG2-EGFP-mMYC stable transgenic offspring using a Trizol extraction protocol. RNA was quantified and made into cDNA using a reverse transcriptase reaction and diluted 1:1, 1:10, 1:100, and 1:1000 with water. Dilutions of cDNA were subject to PCR amplification in the presence of primers specific to zebrafish LMO1, LMO2, HOX11, TLX-3a, TLX-3b, SCL, LCK, and mouse cMYC.

B. The RAG2-cMYC, RAG2-EGFP-cMYC, and RAG2-human MYC-ER Constructs Drive Tumor Formation in $F_0$ Chimeric Fish.

Of 215 $F_0$ RAG2-mcMYC $F_0$ founders, 11 fish exhibited external phenotypes associated with extensive tumor formation, while 7 of 122 RAG2-EGFP-mcMYC fish exhibited signs of disease. The mean latency of tumor onset was 45 days and 52 days for RAG2-mcMYC and RAG2-EGFP-mcMYC fish, respectively. The mean survival, the time at which fish were determined to be terminally ill and were sacrificed, was 64 days for both constructs. Tumor onset ranged from 30 to 131 days. The longest surviving tumor-bearing fish lived 178 days, at which time it was sacrificed.

Some of the RAG2-MYC-ER chimeric fish developed tumors in the absence of tamoxifen-induction (4 of 178 by day 114, 2.2%), indicating that the fusion transgene is active, but somewhat "leaky." Of the RAG2-MYC fish, 5.3% (18 of 337) developed leukemia, with a mean latency of 51 days (range 30-131 d). Only 2.2% of the RAG2-MYC-ER™ chimeric fish had tumors by 114 days. Thus, the use of the ER-conditional system is promising. Similar results were seen in CD2-ER-MYC™ mouse models, where up to 23% of offspring develop tumors in the absence of tamoxifen, while 62% develop tumors by 300 days of development in the presence of tamoxifen (Blyth et al., 2000).

Figure 1C:
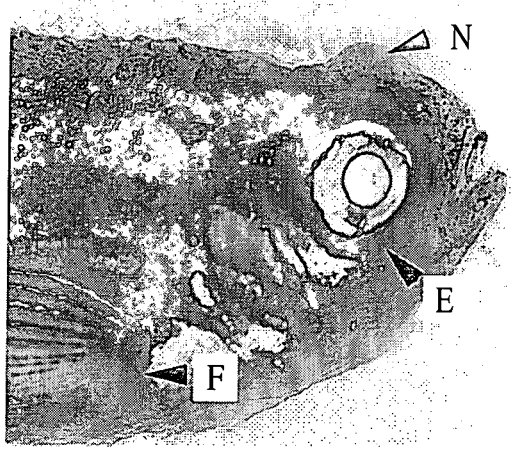
Figure 1D:
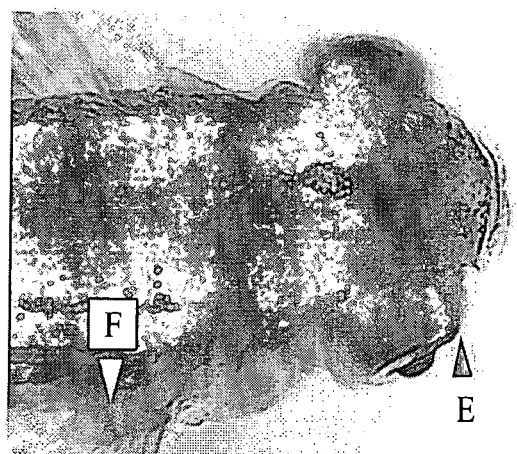
Figure 1E:
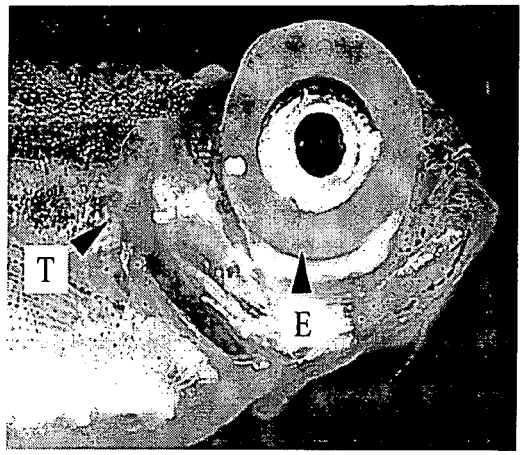
Figure 1F:
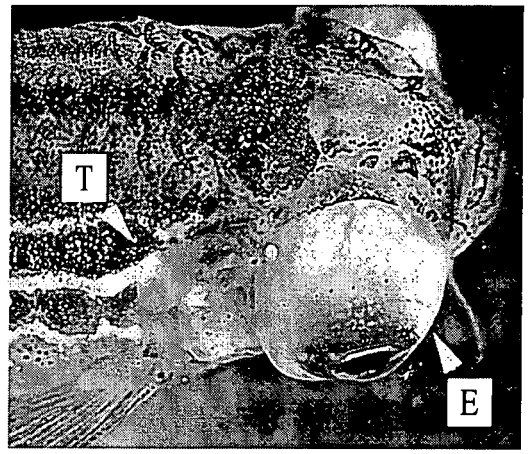
Figure 1G:
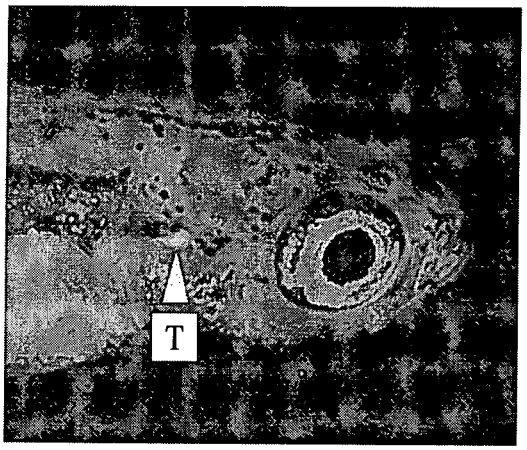
Figure 1H:
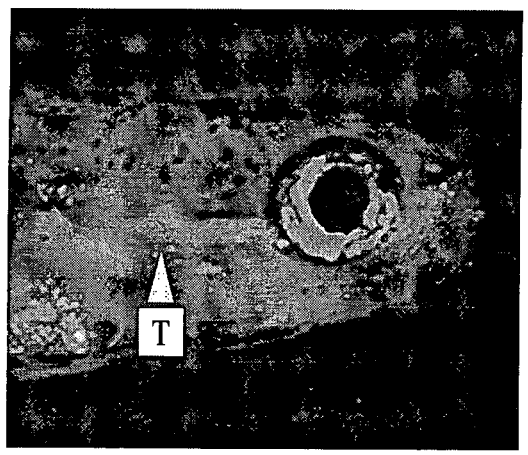
Figure 1I:
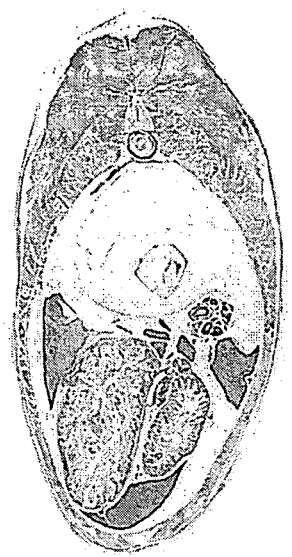
FIGS. 1I-1P depict views of hematoxylin/eosin-stained transverse sections of transgenic fish produced by introduction of nucleic acid comprising RAG2-cMYC, as more fully described in Examples 1B and 1C. Massive infiltration of lymphoblasts in fish with tumors (FIG. 1J) is seen when compared with sections from wild type-fish (FIG. 1I).
Figure 1J:
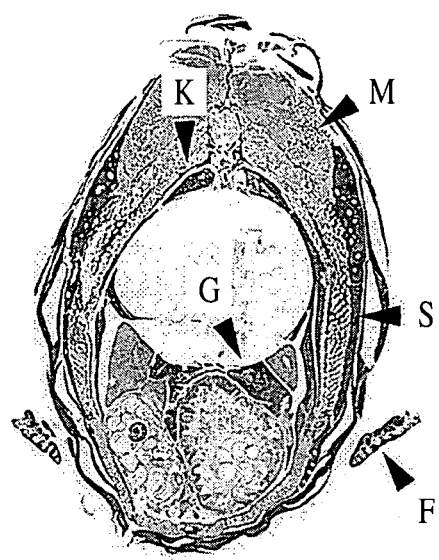
Figure 1K:
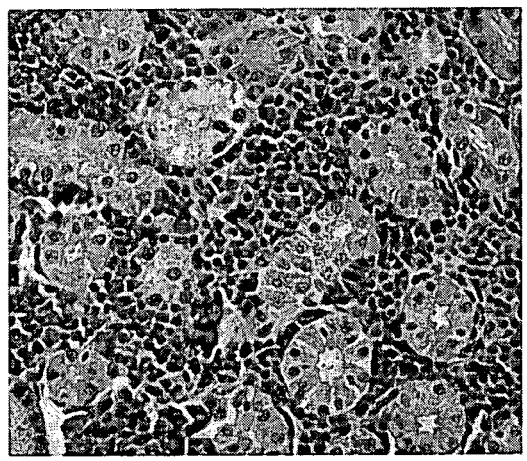

Leukemic fish that were mosaic for RAG2-mMYC, RAG2-EGFP-mMYC, and RAG2-MYC-ER expression had severely distended abdominal cavities, splayed eyes, and variable tumor formations found between and around the eyes (FIGS. 1A-1F). Some fish had growths protruding from the operculum in a position likely corresponding to the thymus (FIGS. 1E-1F) and tumors were commonly found at the base of the pectoral fin (FIGS. 1C-1D). Many of the fish had tumors just beneath the skin, resulting in fish becoming less pigmented over time. In contrast, no RAG2-Lox-dsRED2-EGFP-mMYC chimeric fish developed leukemia/lymphoma.

C. Analysis of Tumor Formation in Transgenic Fish.

Figure 1L:
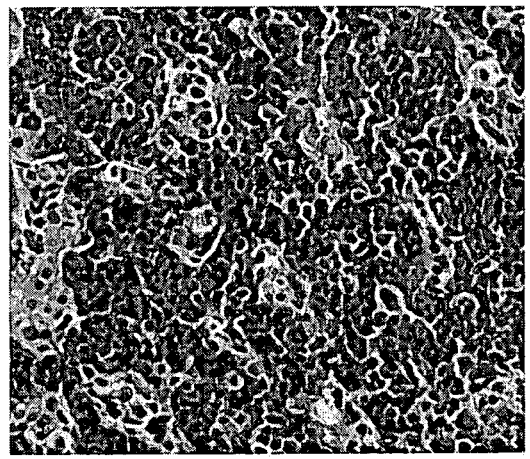
Figure 1M:
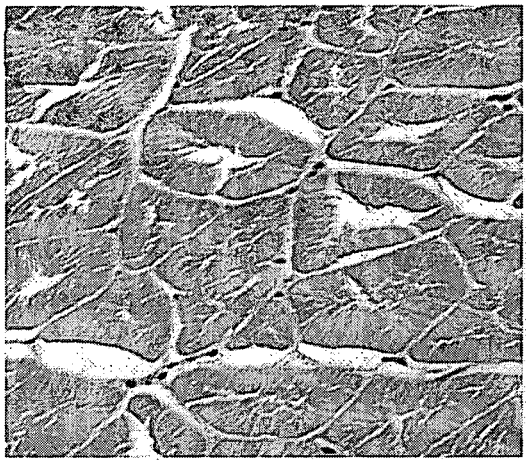
Figure 1N:
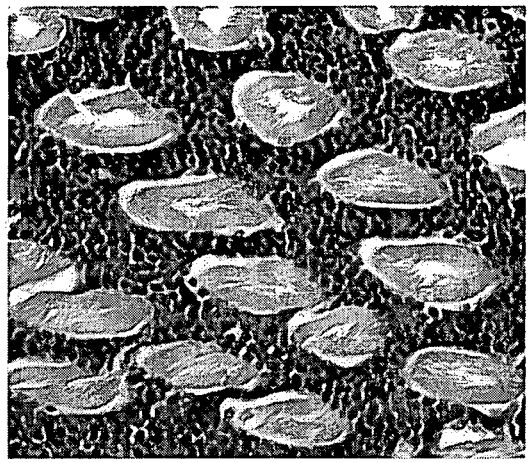
Figure 1O:
Figure 1P:

Three RAG2-mcMYC $F_0$ fish and four RAG2-EGFP-mcMYC fish were sectioned and analyzed for tumor formation based on hematoxylin/eosin staining. All fish analyzed had massive tumor burden with extensive tumor formation occurring throughout the body (FIGS. 1I-1P). Massive infiltration of lymphocytes into the liver, spleen, and kidney (the equivalent of the mammalian blood marrow) was observed (FIG. 1L). Tumor cells were found in between muscle fibers in the dorsal musculature (FIG. 1N), gut, gills, fins, areas surrounding the eye, and just bellow the skin. Prominent tumors were noted in the nasal region (FIG. 1P) that did not appear to arise from RAG2-expressing epithelial cells of the olfactory bulb. Instead, tumors in the nasal region were LCK-positive by in situ analysis and failed to stain with keratin antibody (data not shown), indicating that these nasal tumors were the same T-cell tumors noted throughout the fish. The RAG2-EGFP-mcMYC $F_0$ fish (n=4) had tumors similar to those described for RAG2-mcMYC, although GFP could not be detected by fluorescence microscopy or FACS analysis. Given that the half-life of cMYC is about 30 minutes in normal cells and that the maturation time for the GFP protein is approximately 4 hours, it is not surprising that GFP was not detected, as most of the fusion protein would be targeted for destruction before GFP maturation and fluorescence could occur.

Figure 2E:
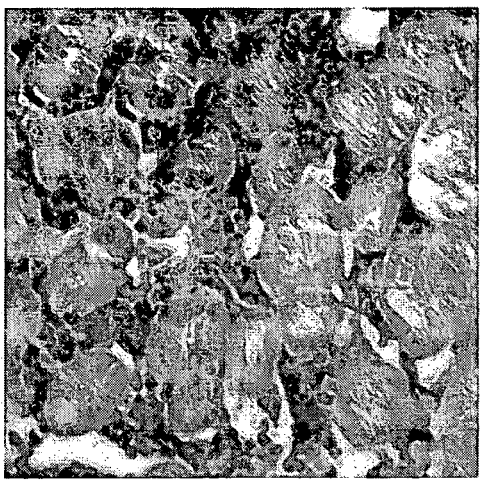
FIGS. 2E-2F, zebrafish LCK. Antisense probes are used in FIGS. 2A, 2C and 2E and sense control probes are used in FIGS. 2B, 2D and 2F. All sections shown in FIGS. 2A-2F are of infiltrating T-cells in the body musculature.
Figure 2F:
Figure 2G:
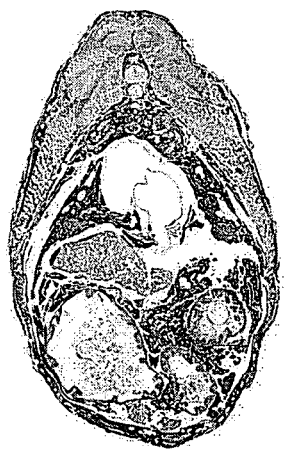
FIGS. 2G-2H depict whole body transverse serial sections stained with hematoxylin/eosin (FIG. 2G) or with anti-GFP antibody on RAG2-EGFP-mcMYC expressing $F_0$ mosaic fish (FIG. 2H).
Figure 2H:
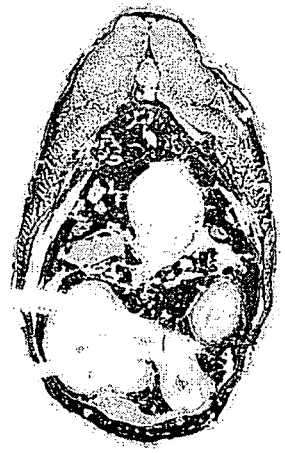
Figure 2I:
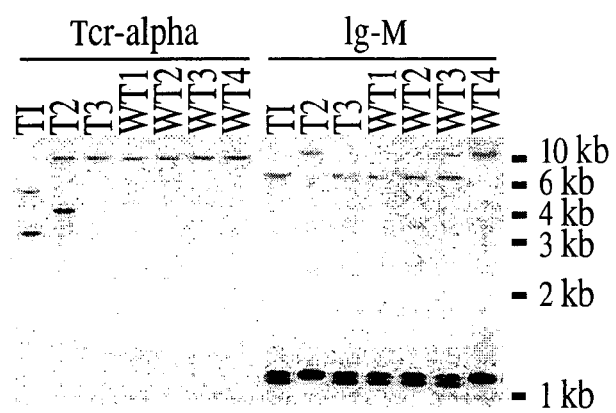
FIG. 2I is a Southern analysis of tumor fish (T1-T3) and wild-type fish (WT1-WT4), as more fully described in Example 1D. Tumor DNA extracted from the tail was digested with Bgl-II and probed with the TCRα- and IgM constant region-specific probes. Bgl-II cuts within the constant region of IgM, resulting in two bands being detected (T2 and WT4). Four bands were detected in the remaining DNA samples and results from polymorphisms found within the IgM gene locus (T1, T3, and WT1-WT3).
Figure 3A:
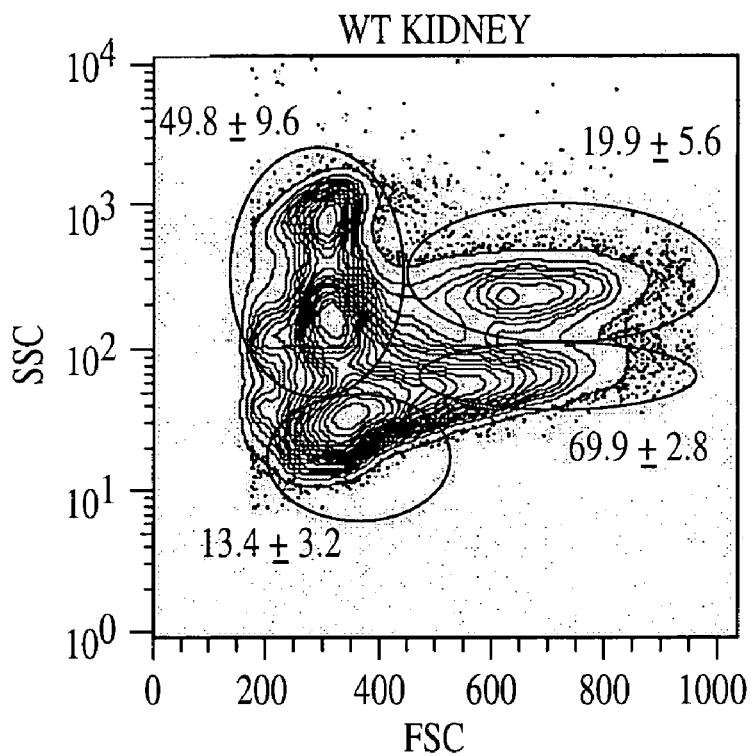
FIGS. 3A-3F depict a fluorescence activated cell sorting (FACS) analysis and blast morphology of tumors formed in transgenic fish having nucleic acid comprising RAG2-cMYC as more fully described in Example 1C. Gated populations include red blood cells (red), lymphoid cells (blue), myeloid cells (green), and progenitors (pink). Sorted kidney blasts were reanalyzed by FACS (FIG. 3C) and analyzed morphologically by May-Grunwald staining of cytospin cell preparations as shown in FIG. 3F, which depicts a representative field of sorted blasts. Populations of cells within each gate are noted as percent of total cells. Forward scatter (FSC-H) and side scatter (SSC-H). Images in 3F were taken at 1000× magnification.
Figure 3B:
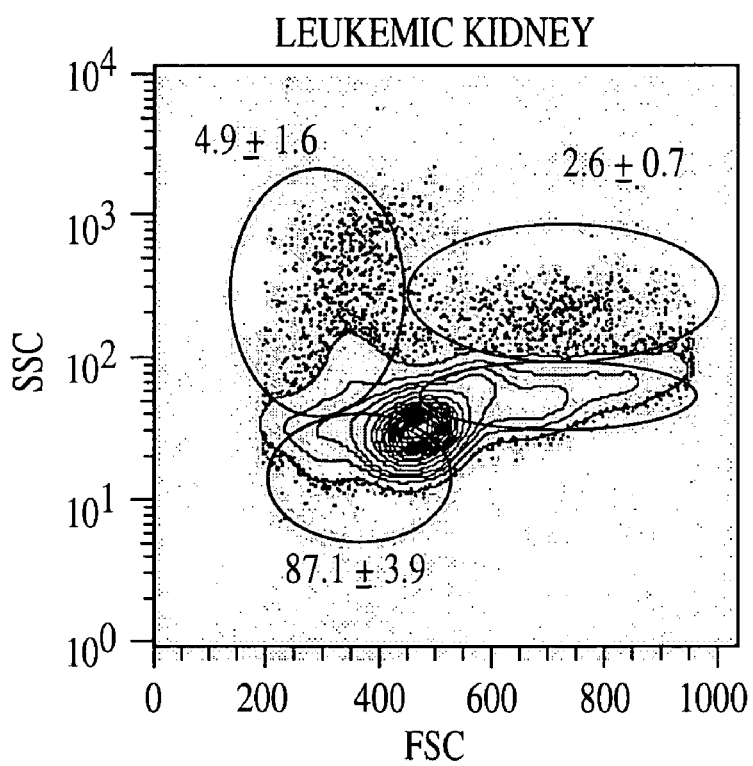
Figure 3C:
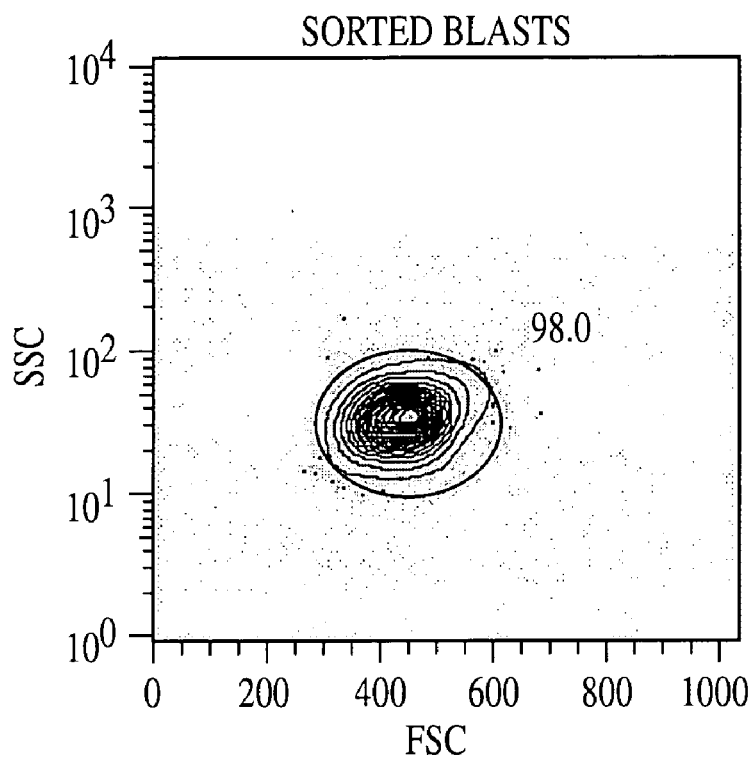
Figure 3D:
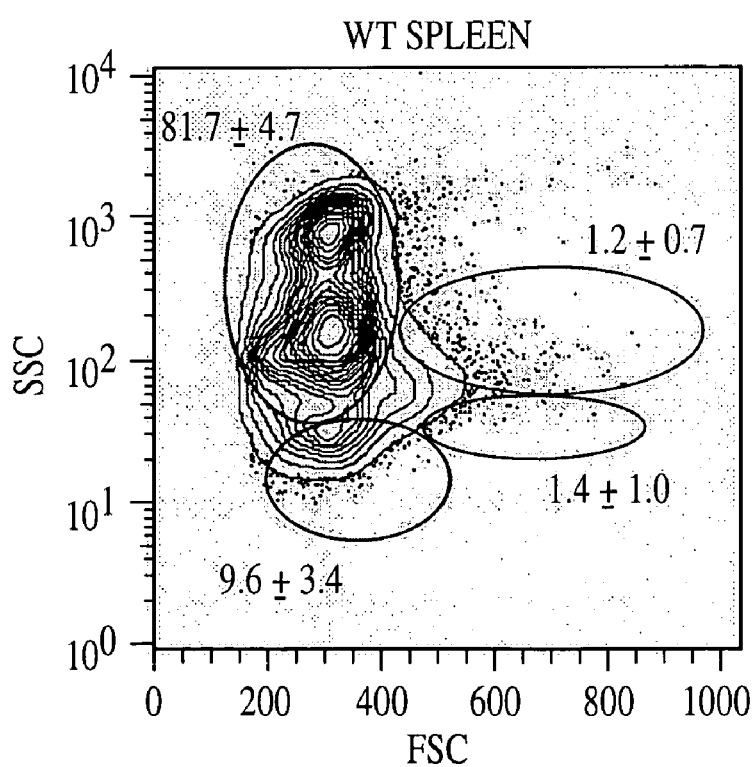
Figure 3E:
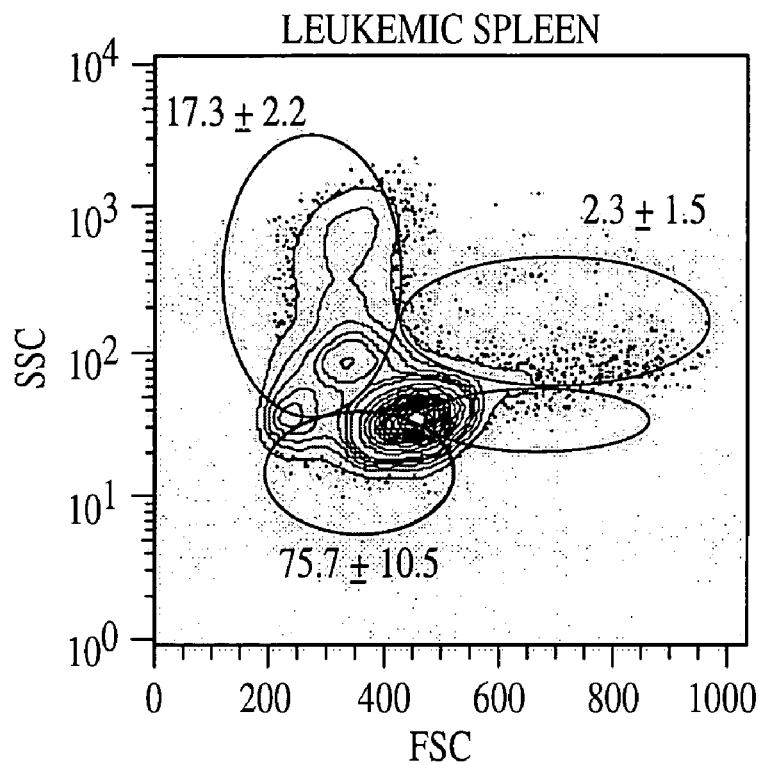
Figure 3F:
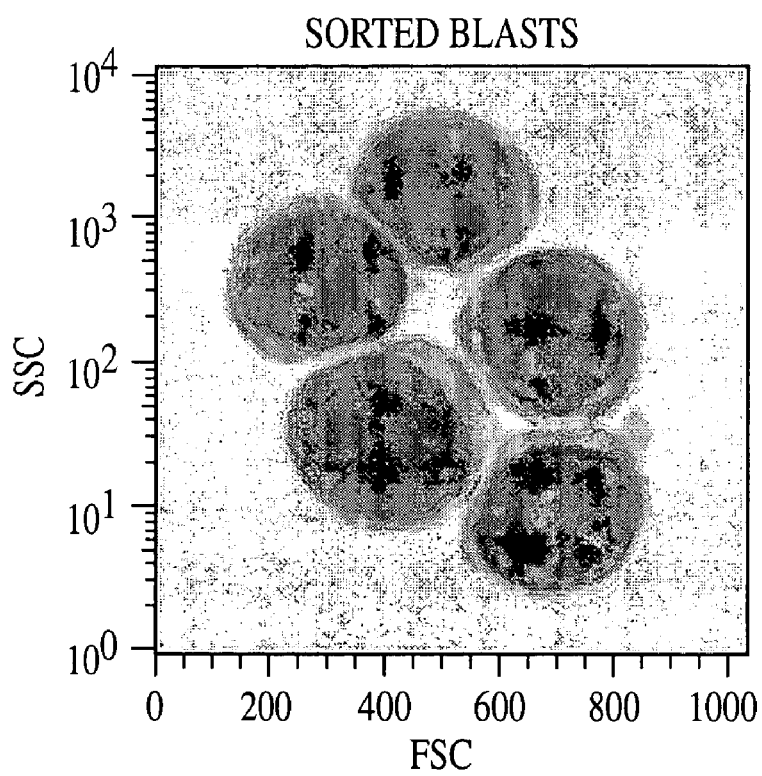

Of the seven tumor-bearing fish analyzed histologically, all had T-cell acute lymphoblastic leukemia. Paraffin sections were analyzed for RNA expression of the T-cell genes TCRα and LCK and the B-cell genes IgM and IgLC. The lymphoid markers RAG1 and RAG2, and mcMYC expression was analyzed by in situ hybridization. All tumors were positive for mcMYC (FIGS. 2A-2B), RAG1, RAG2 (FIGS. 2C-2D), and LCK (FIGS. 2E-2F). RNA expression of the other genes could not be detected. RAG2-EGFP-mcMYC fish were analyzed for expression of the GFP-fusion protein by immunocytochemistry using the anti-GFP antibody (Clontech, JL-8) and showed strong nuclear protein expression in tumor cells (FIGS. 2G-2J). These results indicate that the RAG2-promoter drives both mcMYC RNA and protein expression, and is responsible for oncogenic transformation of T-cells in the mosaic $F_0$ fish.

Two RAG2-mMYC and two RAG2-EGFP-mMYC $F_0$ mosaic fish were analyzed by FACS analysis and total cell counts were made for the kidney and spleen. In wild-type AB fish, the kidney typically has $8.4+/-3.7\times10^5$ (N=7) blood cells, while the spleen has $8.2+/-6.3\times10^4$ (N=6) (Traver et al., in preparation). In the tumor bearing fish, $4.95+/-3.3\times10^6$ (N=5) cells were found in the kidney and $4.64+/-1.5\times10^5$ (N=4) cells were found in spleen. Although the leukemic kidneys and spleens contained more cells in total than wild-type controls, total red blood cell and myeloid population numbers were not drastically altered, indicating that lymphocytes accounted for the increased number of cells found in the spleen and kidney (FIG. 3). The percentage of blasts in the kidney was $87.1+/-3.9\%$ (N=4, range 83.1 to 92.2%), while in the percentage of blasts in the spleen was $75.7+/-10.5\%$ (N=4, range 60.8 to 85.3%). Tumor cells had a granularity similar to that of normal lymphocytes based on side scatter (SSC on Y-axis of FIGS. 3A-E), but were slightly larger based on forward scatter (FSC on X-axis). Because the kidney marrow is analogous to the bone marrow in mammals, and because leukemia is generally defined as >30% blasts in the bone marrow, the mosaic fish had disseminated T-cell acute lymphoblastic leukemia with blasts accounting for $87.1+/-3.9\%$ of the cells in the kidney.

D. Verification of Clonality and Lineage of Other Tumors.

To determine clonality as well as lineage of the tumor cells, Southern blot analysis was performed on restriction enzyme-digested tumor DNAs using radiolabeled probes that corresponded to the zebrafish TCRα (Haire et al., *Immunogenetics*, 51: 915-923 (2000)) and IgM constant regions. Of the three tumors analyzed, one had monoclonal TCRα gene rearrangements and one had oligoclonal TCRα gene rearrangements (FIG. 21). The third tumor showed germ line configuration of TCRα but had very strong LCK RNA expression, which confirmed T-cell origin. Tumor cells from the third tumor were typically arrested in thymic differentiation prior to TCRα gene rearrangement. None of the tumors had rearrangement of the IgM gene, which, when combined with the presence of TCRα gene rearrangements and LCK gene expression, indicated that all the tumors identified were of thymocyte origin.

Mice that expressed cMYC under the control of CD2 or Thy1 promoters also developed T-cell lymphoma, which arose from monoclonal or oligoclonal populations of T-cells. Thus, the fish and mouse tumors were similar with respect to stage of differentiation arrest and clonality.

E. Transplantation of Tumor to Recipient Fish.

Figure 4A:
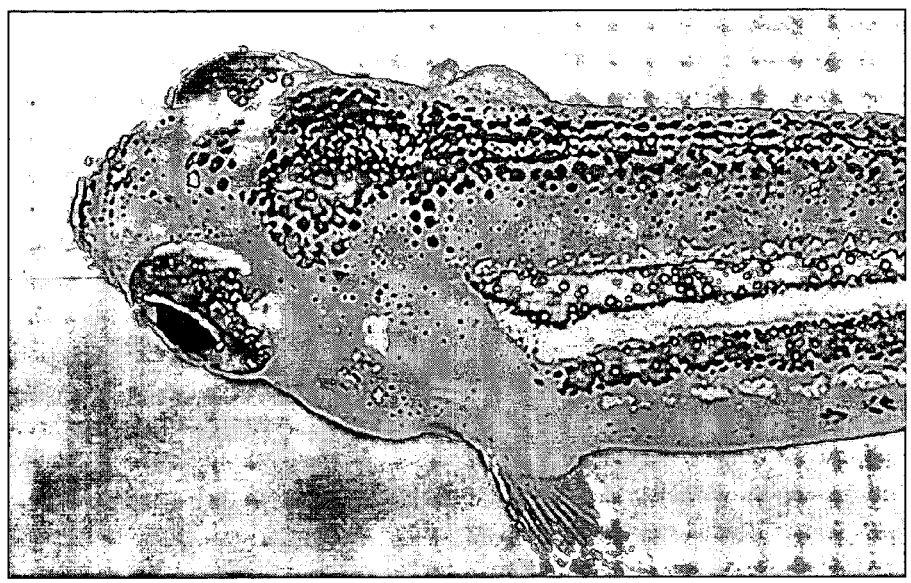
FIG. 4A depicts a top view of a wild-type AB fish that received transplanted tumor cells as a 2 day-old embryo at 44 days, as more fully described in Example 1E.
Figure 4B:
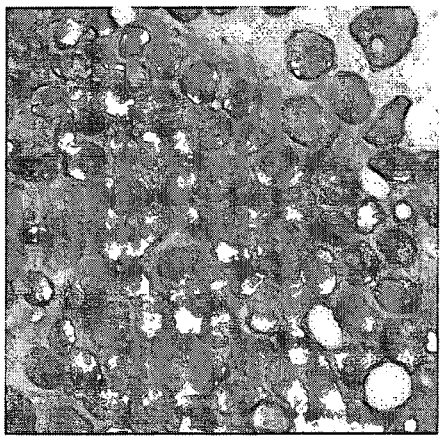
FIGS. 4B-4D depict touch preps of body musculature of transgenic fish.
Figure 4C:
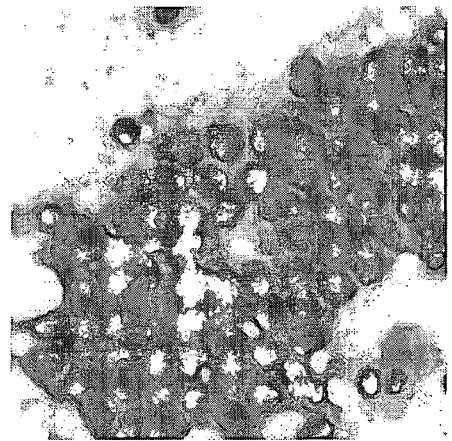
Figure 4D:
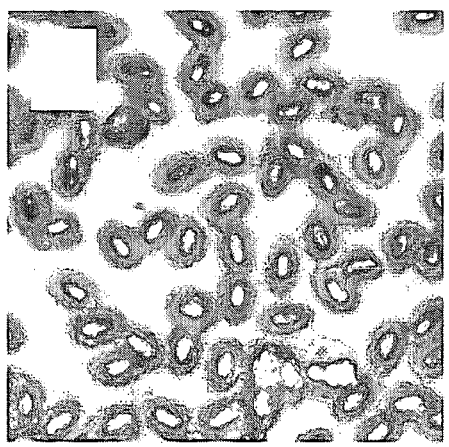
Figure 4E:
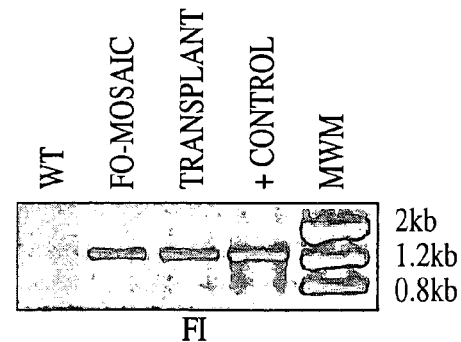
FIG. 4E depicts an agarose gel stained with ethidium bromide showing polymerase chain reaction (PCR) analysis of genomic DNA isolated from the tail musculature of wild-type AB fish (WT), $F_0$ mosaic fish ($F_0$-mosaic), and embryo with tumor cell transplant from FIG. 4A (Transplant). PCR was completed on the plasmid used for injection as a positive control (+ control). The molecular weight marker (MWM) and band sizes are noted.

To analyze whether tumors could be transplanted, tumor cells were harvested from the kidneys of $F_0$ mosaic fish and injected intraperitoneally into 2-day old AB wild-type embryos. Of 25 fish injected, one fish developed leukemia by day 44 (FIG. 4A). This fish had a similar phenotype as that observed in $F_0$ mosaic fish, having a distended abdomen, splayed eyes, and tumors extending from the operculum to the pectoral fin joint. Touch preps confirmed that this transplanted fish had tumors similar to $F_0$ mosaic fish (FIGS. 4B-D), as did histological analysis (data not shown). PCR was completed on tumor DNA, which was extracted from the invading cells in the tail region, and confirmed that the fish carried the cMYC transgenic construct (FIG. 4E).

Figure 4F:
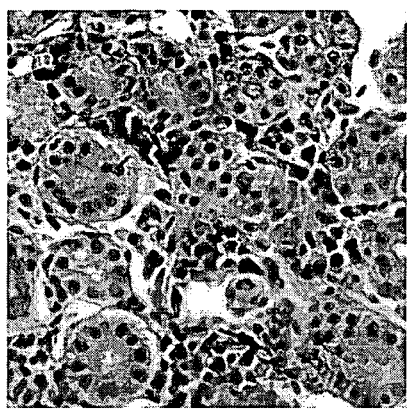
FIGS. 4F-4I depict hematoxylin/eosin stained sections of the kidney (FIGS. 4F-G) and musculature (FIGS. 4H-I). Adult wild-type fish were sublethally irradiated with 2500 Rads and injected with whole kidney marrow.
Figure 4G:
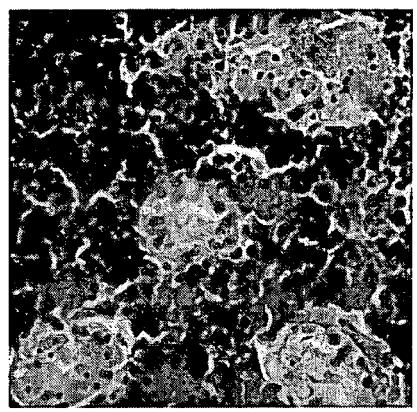
Figure 4H:
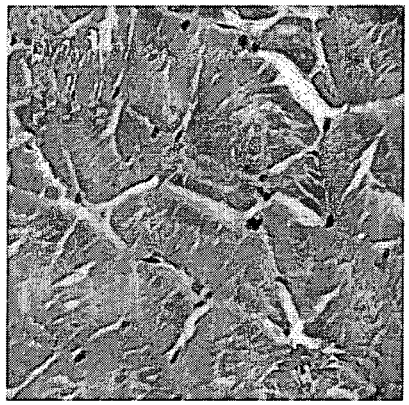
Figure 4I:
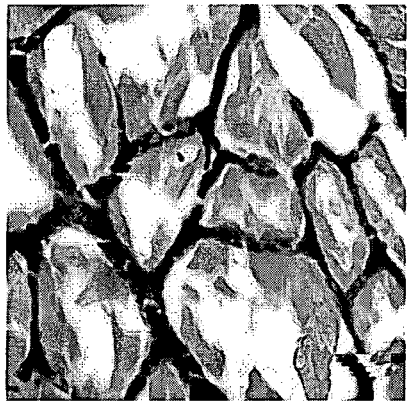
Figure 4J:
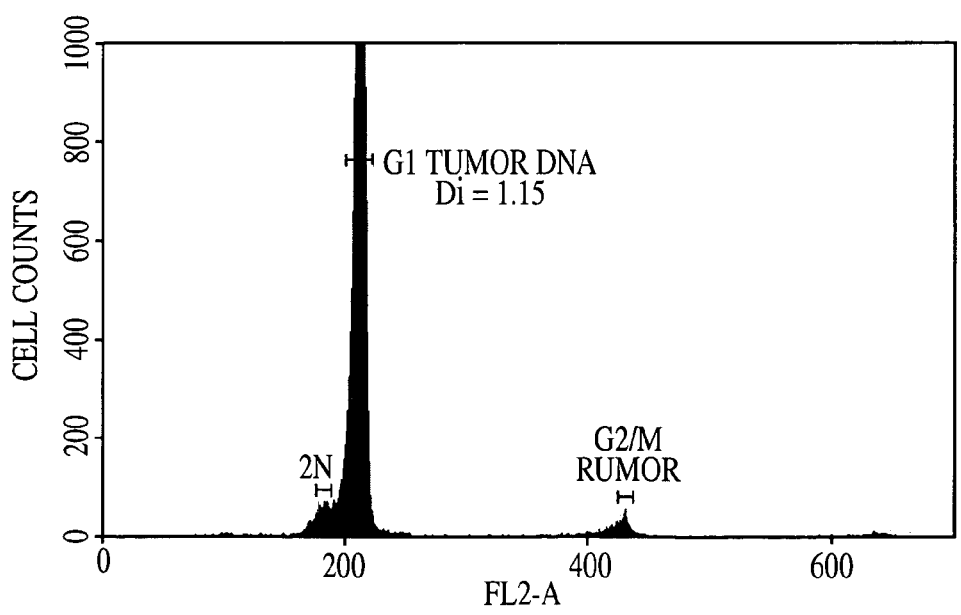
FIG. 4J depicts a flow cytometric analysis of a tumor from RAG2-mcMYC $F_0$ mosaic fish to determine DNA content as more fully described in Example 1.

Tumors were also transplantable into irradiated adult fish. Fish were anesthetized with tricaine and sublethally irradiated with 2500 Rads from a $^{35}Cs$ source two days prior to injection with tumor cells. Five fish were injected intraperitoneally with either $3.6\times10^5$ total kidney cells or $1\times10^5$ sorted blasts. Of the five fish injected with whole kidney marrow, one died as a result of the injection procedure, and two died before the analysis could be completed. The remaining two fish were sacrificed 25 days after injection and analyzed histologically for tumor formation. Both fish had massive infiltration of tumor cells into the kidney (FIG. 4G) and body musculature (FIG. 4I) when compared to uninjected, irradiated control fish (FIGS. 4F and 4H). Of the five fish injected with sorted blasts, three survived until 25 days post-injection, at which time they were sacrificed. All three fish had tumor formation similar to both the $F_0$ mosaic fish and the fish injected with whole kidney marrow. However, two of the fish had less severe tumor invasion when compared to other transplanted fish, possibly as a result of less cells being injected into fish receiving sorted blast cells. RNA in situ hybridization confirmed that transplanted tumors expressed mMYC, RAG1, and RAG2 and were morphologically indistinguishable from tumors arising in $F_0$ mosaic zRAG2-mMYC fish (data not shown), All three control irradiated fish analyzed had normal histological morphology when compared to non-irradiated control fish.

F. Determination of Ploidy of RAG2-mcMYC Tumors.

MYC expression in tumors often results in genomic instability and accumulation of extrachromosomal fragments. To determine if RAG2-mcMYC tumors were heterodiploid, FACS analysis was completed on one tumor-bearing fish to determine the DNA content in the tumor cells (FIG. 4B). The analyzed tumor had a DNA index of 1.15. Upon mixing tumor and wild-type sample, the tumor peak decreased while the 2N peak increased (data not shown), verifying that the 2N and tumor peaks were distinct in tumor samples.

G. Developing Stable Lines of Transgenic Zebrafish that Express the RAG2-EGFP-mMYC Transgene.

Although 5% of the $F_0$ mosaic fish develop lymphoma, other injected $F_0$ fish may have transgene integration into germ cells without integration into the lymphoid cells. These fish should be healthy and should give rise to transgenic $F_1$ progeny. Offspring from ~350 $F_0$ founders were screened by genomic PCR, and 7 individuals were identified that were able to pass on the transgene to the $F_1$ progeny. Of those, only one expressed the EGFP-MYC transgene. RAG2-EGFP-MYC $F_1$ fish progeny of this founder fish developed GFP-positive thymic tumors by 22 days of development (Langenau et al., 2003).

Figure 10:
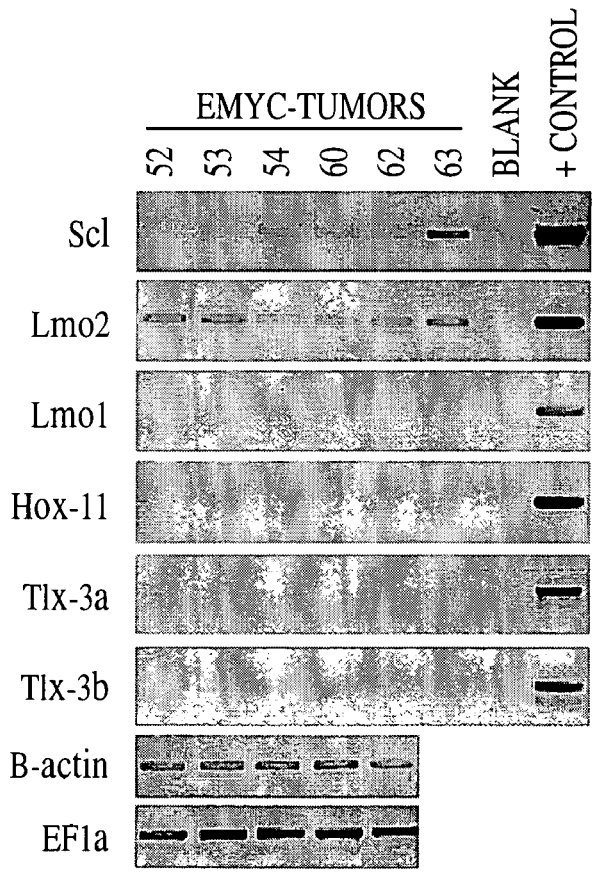
FIG. 10.
Figure 11:
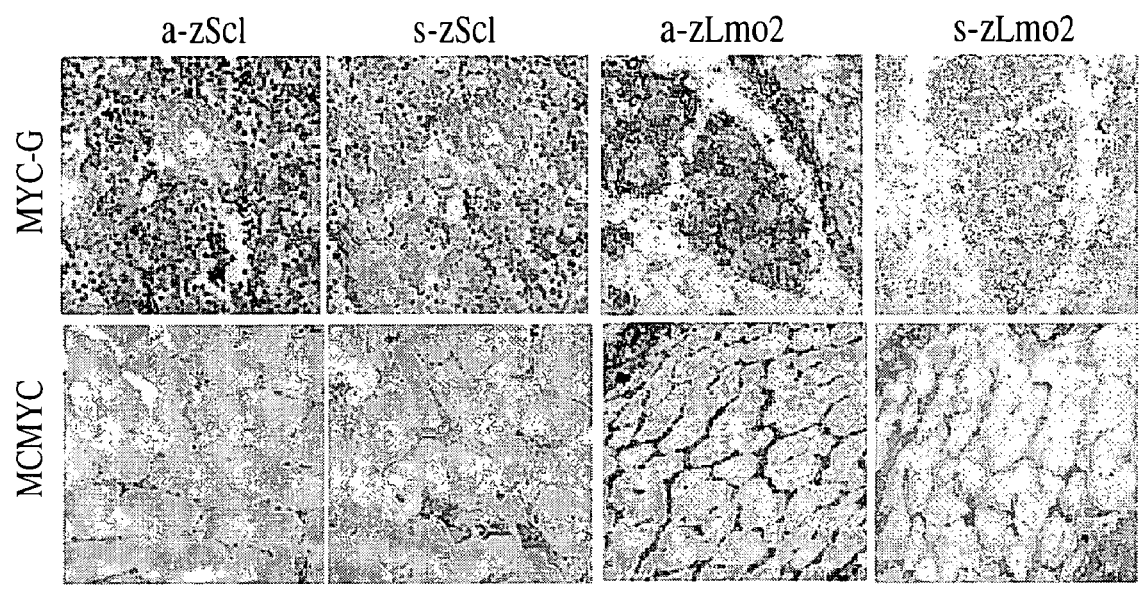
FIG. 11.

These tumors expressed the zebrafish RAG 1, RAG2, and Lck genes, which indicated that the tumors that developed in the RAG2-EGFP-mMYC stable line were similar to those that developed in mosaic fish. Additionally, tumors had clonal rearrangement of the TCRα genomic locus, and some tumors were clonally aneuploid as determined by DNA content. Five of 34 (15%) tumors analyzed had DNA indices ranging from 1.02-1.10. Finally, LMO2 and SCL were expressed in our EGFP-mMYC-induced leukemias, as confirmed by both RT-PCR (FIG. 10) and in situ analysis (FIG. 11). The most common subclass of childhood T-ALL expresses both SCL and LMO1/2, and this subclass of patients has the worst prognostic outcome of all patient groups. Thus, this zebrafish model may be used for the most common and most deadly form of human childhood T-ALL.

Given the early onset of tumor formation in $F_1$ RAG2-transgenic fish that harbor EGFP-MYC transgene, and that the mean survival of transgenic fish is 81 days (range 50 to 111 days, n=53), it has not been possible to mate $F_1$ fish. However, because the testes are developed by 8-12 weeks of age, the testes from leukemic male fish have been extracted for use in in vitro fertilization to maintain the lines. The line has been carried and $F_3$ fish were produced and are currently growing in our system. Because the IVF procedure is cumbersome, and may not be amenable for use in large scale genetic screens, conditional transgenic zebrafish lines using a tamoxifen-sensitive MYC-ER™ transgene (Blyth et al., 2000) will be generated, and a CRE-mediated strategy will be pursued to induce expression of the EGFP-mMYC transgene, as outlined above (Example 1.A.1).

H. Developing Conditional Stable Lines of Transgenic Zebrafish that Express an Inducible MYC Transgene.

At least two different strategies may be used to generate conditional transgenic zebrafish lines that express inducible MYC alleles under control of the RAG2 promoter.

The first strategy utilizes the tamoxifen-inducible human MYC-ER fusion transgene. Approximately 400 fish were injected with the RAG2-MYC-ER™ transgene and are currently growing up in our system. Some of these fish developed tumors (4 of 178 by day 114, 2.2%), which indicated that the transgene is active, but somewhat "leaky." Of the RAG2-MYC fish, 5.3% (18 of 337) developed leukemia, with a mean latency of 51 days (range 30-131d). Only 2.2% of the RAG2-MYC-ER™ chimeric fish developed tumors by 114 days. Thus, the use of the ER-conditional system is promising. Similar results were seen in CD2-MYC-ER™ mouse models, where up to 23% of offspring developed tumors in the absence of tamoxifen, while 62% develop tumors by 300 days of development in the presence of tamoxifen (Blyth et al., 2000).

$F_0$ fish that yield PCR-positive offspring will be mated weekly, and their clutches will be raised. Some clutches will be used to verify that the transgene is expressed in the offspring by either whole mount in situ hybridization or by immunocytochemistry using antibodies specific for human cMYC or the estrogen receptor. The remaining clutches will be raised to adulthood, and DNA will be isolated from fin clips for PCR screening to identify $F_1$ founders.

To test the response of MYC-ER™ to tamoxifen in the fish, the RAG2-MYC-ER™ transgene will be injected into embryos from the RAG2-GFP line, raised for 6 days in the absence of tamoxifen, and scored for GFP-positivity. Embryos with GFP-positive T-cells by 6 days of development will be raised in the presence of tamoxifen (0, 0.1, 1.0, and 10 µM) from day 6 to day 35, and scored for tumor development at 35 days. Water changes will be completed every 3 days over this period with tamoxifen being replaced each time. These experiments will define what dose of tamoxifen is necessary to induce the MYC-ER™. Because 5% of injected fish integrate the transgene into their T-cells (Langenau et al., 2003), at least 100 primary injected fish will be assessed per group. To verify that the response is due to tamoxifen and not the "leakiness" of the MYC-ER™ transgene, leukemic fish will be removed from tamoxifen and scored for tumor regression.

Figure 9:
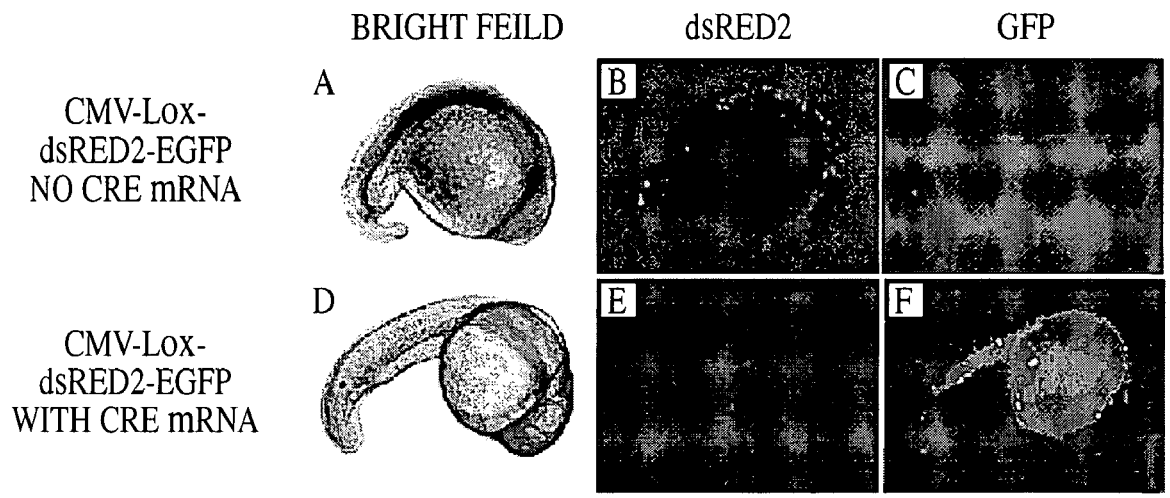
FIG. 9.

The second strategy to produce conditional transgenic zebrafish lines uses a CRE/Lox-mediated excision event to drive expression of the EGFP-mMYC transgene. We co-injected the CMV-Lox-dsRED2-EGFP plasmid in combination with CRE plasmid or CRE RNA. In embryos injected with CMV-Lox-dsRED2-EGFP plasmid alone, fish were red fluorescently labeled, but not green. In contrast, embryos co-injected with plasmid, the fish were both red and green under fluorescence, which indicated that CRE-recombination occurred in the zebrafish embryos and that the plasmids were co-expressed in some but not all cells (FIGS. 8.B-8.E). To test efficiency of CRE excision of the dsRED2 loxed allele, we co-injected CMV-Lox-dsRED2-EGFP with or without CRE RNA. In the absence of CRE RNA, fish were red, but not green (FIGS. 9.A-9.C). When 50 ng/µl of CRE was co-injected with the CMV-Lox-dsRED2-EGFP plasmid, there was 100% excision of the dsRED2 allele; the fish were green, but never red (FIGS. 9.D-9.F). These results indicated that the CRE/lox strategy worked transiently in the fish, and highlighted the fact that CRE RNA was not toxic to fish and may be injected in vivo.

A RAG2-loxed-dsRed2-EGFP-MYC was made and injected into over 300 surviving fish. The transgene was detected by dsRed2 fluorescence at 6 days post-fertilization (FIGS. 7.B and 7.C). Mosaic fish were identified, which have strong expression of the red fluorophore in T-cells at three months of age, However, none of these fish developed tumors, which indicated that the ds-Red protein was being expressed, while the EGFP-MYC protein was not. The $F_0$ founder fish will be screened for the ability to pass on the transgene, as detected by dsRed2 fluorescence.

I. Discussion.

Understanding the genetic events that lead to tumor formation in cMYC-expressing cells is important to developing treatments for diseases such as Burkitt's Lymphoma, follicular B-cell lymphoma, and T-cell acute lymphoblastic leukemia. By identifying the genetic events that stop transformation in fish prone to developing cMYC-induced tumors, it may be possible to identify conserved mechanisms involved in human disease. The genes identified by genetic suppressor screen are potential targets for drug development and may lead to new therapies in diverse cancers in which cMYC is amplified or overexpressed. Additionally, small molecule inhibitors or other drugs or agents identified in chemical screens that suppress MYC-induced leukemia in the transgenic fish described herein fish may be candidates for clinical trials in human patients and may lead to the discovery of new therapeutic agents in the future. Finally, developing a model of cancer in the fish provides a precedent for developing other models of malignant transformation in the fish that utilize other promoters and other oncogenes, some additional examples follow.

EXAMPLE 2

Use of RAG2-EGFP-Zebrafish BCL2 Transgenic Models to Identify Chemical and Genetic Suppressors of BCL2 Function in T-Cells A. Materials and Methods.

Diseases such as follicular B-cell lymphoma have activation of BCL2, an anti-apoptotic gene, which renders these tumors resistant to apoptosis and allows them to become less sensitive to chemotherapy and radiation therapy than B-cells transformed by other mechanisms. Additionally, a large proportion of tumors misexpress the MYC oncogene, a transformation event that necessarily requires inactivation of the apoptotic machinery. Creating drugs that inhibit BCL2 or MYC function in transformed cells would be advantageous for treating human tumors and may be used in combination with chemotherapy and radiation therapy to selectively kill cells that have overexpression of this oncogene. Similar experiments to those described herein for BCL2 may also be performed with, e.g., cMYC.

1. DNA Constructs.

Degenerate PCR was used to amplify a zebrafish BCL2-related cDNA fragment from 1-5 day embryos, and the resulting DNA fragment was cloned into a pGEMT-EASY vector (Promega). Clones were sequenced and used as probes to obtain a full-length clone by screening a whole embryo cDNA library (RZPD). Specifically, the plasmid DNA was digested to release the BCL2-related cDNA fragment, resolved on an ethidium bromide-containing agarose gel, and DNA was extracted from the gel band. The gel purified DNA was radiolabeled using the REDI-PRIME II random labeling system (Amersham) and used to probe a full-length cDNA library. One full-length clone was obtained and sequenced.

Figures 12A, 12B, 12C:
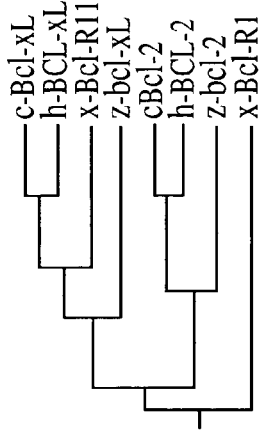
FIG. 12.
Figure 13A:
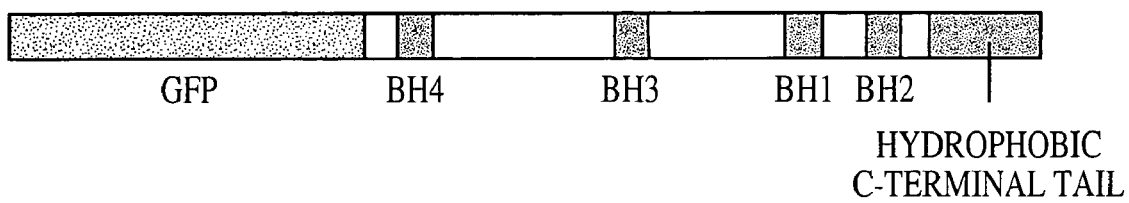
FIG. 13. Expression of the EGFP-zBCL2 fusion protein during embryogenesis rescues developmentally regulated apoptosis. (A) Diagram of the EGFP-zBCL2 fusion transgene. TUNEL stained 16 hpf embryo injected with GFP control RNA (B) or EGFP-zBCL2 RNA (C). (D) Graph showing that number of apoptotic cells in the embryo is significantly decreased in embryos injected with EGFP-zBCL2 RNA when compared to uninjected control or GFP injected control fish.
Figure 13B:
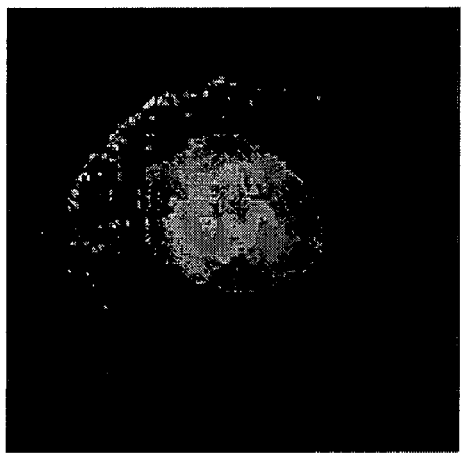
Figure 13C:
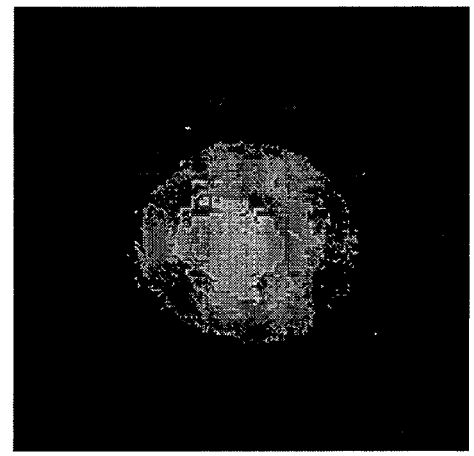
Figure 13D:
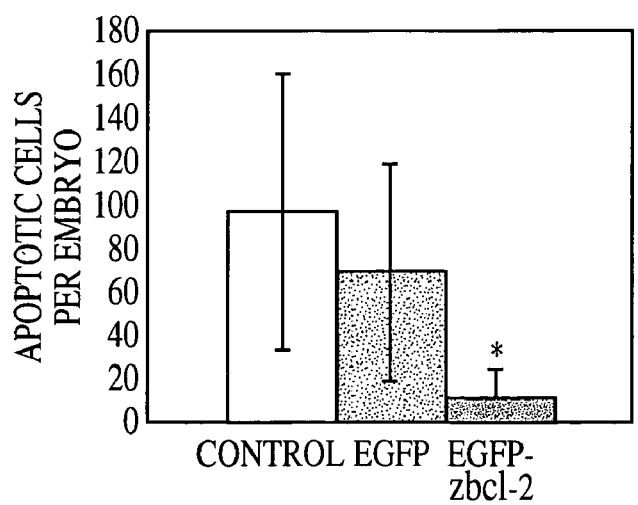

Deduced amino acid similarity of zebrafish BCL2 (zBCL2) placed our gene with other BCL2 family members (FIG. 12). Phylogenetic analysis suggested that our zebrafish BCL2-like gene was likely the true BCL2 homolog in fish, as it clustered with other vertebrate BCL2 proteins and failed to cluster with BCL-xL proteins.

We created the EGFP-zBCL2 gene-fusion by fusing EGFP to the amino terminus of zBCL2 (FIG. 13.A). Specifically, the zBCL2 cDNA was amplified using PCR in the presence of a forward primer that altered the methionine start site. Additionally, the forward primer contained a Sal1 site, while the reverse primer contained a HindIII site to facilitate cloning into the EGFP-C1 vector (Clonetech). The resulting PCR fragment was PCR purified using the QIAQUICK PCR purification system (Qiagen) and digested overnight with Sal1 and HindIII. The digested PCR product was resolved on an ethidium bromide-containing agarose gel. The resulting DNA band was excised, and the DNA was extracted. This DNA was cloned into the EGFP-C1 vector, which had been digested with Xho1 and HindIII. The resulting plasmid created an EGFP-zBCL2 gene fusion.

Next, the RAG2-EGFP-zBCL2 transgene was made by digesting the above vector (EGFP-C1-zBCL2) with BamH1 and HindIII, and the resulting fragment was cloned into the RAG2-promoter-containing vector, essentially as outlined in Example 1.A.1. This RAG2-EGFP-zBCL2 vector was then digested with Cla1 and BamH1, and cloned into the pCS2+ vector.

2. Embryo Injections: Transient Analysis of the EGFP-zBCL2 Transgene in Fish.

To verify that our fusion protein was functional, EGFP-zBCL2 RNA and GFP control RNA was injected into embryos at the one-cell stage. Embryos were then analyzed for inhibition of developmentally regulated apoptosis at 16, 20, and 24 hours. Additionally, GFP-positive EGFP-zBCL2 RNA and GFP control RNA-injected embryos were irradiated with 16 Gy of irradiation at 14 hpf and fixed in paraformaldahyde at 20 hpf. RNA was created and injected as outlined essentially as described for PCS2+CRE RNA in Example 1.A.2. GFP-positive fish were sacrificed and analyzed for the presence of apoptotic cells by TUNNEL assay.

3. Whole Mount Tunnel Analysis.

Whole mount TUNEL analysis was completed using TMR-Red In Situ Cell Death Kit (Roche).

4. Embryo Injections: Creation of Mosaic Founder Fish and Stable Transgenic Lines.

The RAG2-EGFP-zBCL2 vector was linearized by digestion with Xho1 or Not1 at 37° C. overnight, and DNA was purified by phenol:chloroform extraction followed by ethanol precipitation. DNA concentration was assessed by both UV spectrophotometry and gel quantification. Linearized DNA was diluted to 100-200 ng/microliter in 0.5×TE/100 mM KCl and injected into wild-type AB embryos at the one-cell stage of development using a glass micropipette. The volume of DNA injected was titered to a point at which 20-50% of the embryos exhibited morphological features associated with over-injection of DNA. This is commonly seen in microinjection into zebrafish and ensures that surviving embryos have high levels of DNA integration into cells. The 20-50% of embryos exhibiting "monster" morphology were discarded.

Embryos were grown in E3 egg water at 28.5° C. until 15 days of development, at which time they were placed into a re-circulating system.

5. Histological Methods.

RAG2-EGFP-zBCL2 transgenic and AB control fish were analyzed histologically. Fish were fixed in 4% paraformaldehyde at 4° C. overnight and processed for embedding in paraffin. Methods for dehydration of tissue samples are well known in the art. Fish were cut transversely into 5-10 mm sections and embedded into paraffin. Blocks were sectioned at 5-10 microns through the length of the fish and every tenth slide was stained with hematoxylin/eosin. Slides were analyzed by light microscopy and compared to wild-type AB fish sections.

6. Irradiation Sensitivity.

RAG2-GFP and RAG2-EGFP-zBCL2 transgenic fish were treated with a whole-body dose of 15, 20, and 25 Gy of ionizing irradiation. Fish were analyzed for irradiation responses at 6 dpf, 21 dpf, and 3 months of age as determined by loss of GFP labeled T-cells in the thymus.

B. The EGFP-zBCL2 Transgene is Functional.

Figure 14A:
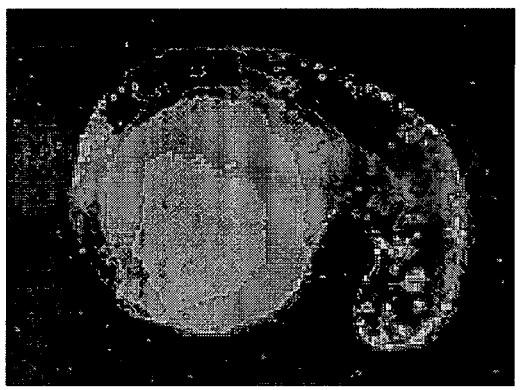
FIG. 14. Expression of the EGFP-zBCL2 fusion protein during embryogenesis rescues radiation-induced apoptosis. Tunel stained 20 hpf embryo injected with GFP control RNA (A) or EGFP-zBCL2 RNA (B) following irradiation at 14 hpf.
Figure 14B:
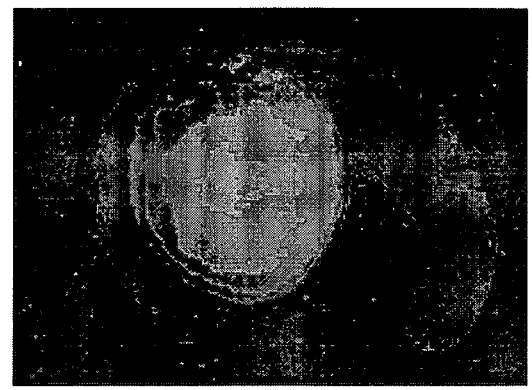

To verify that our fusion protein was functional, EGFP-zBCL2 RNA was injected into embryos at the one-cell stage. Embryos were analyzed for inhibition of developmentally regulated apoptosis at 16 hours post-fertilization. GFP-positive fish were sacrificed and analyzed for the presence of apoptotic cells by TUNEL assay. The EGFP-zBCL2 RNA rescued apoptosis that normally occurred in the developing embryo (FIGS. 13.B-G.D). Additionally, EGFP-zBCL2 RNA rescued irradiation-induced apoptosis in the developing embryos (FIG. 14). Both of these experiments showed that the EGFP-zBCL2 transgene was a potent inhibitor of apoptosis in vivo, and the transgene may be easily visualized in living fish.

C. T-cells which Express the RAG2-EGFP-zBCL2 Transgene are Protected from Irradiation-Induced Apoptosis.

Figure 15:
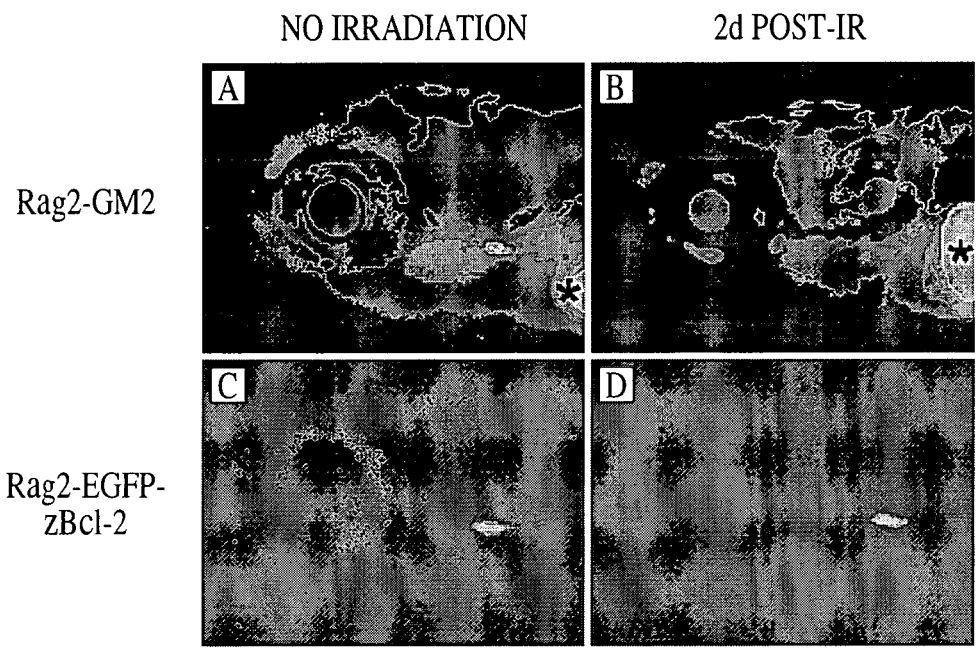
FIG. 15. T-cells from 6-day-old RAG2-EGFP-zBCL2 transgenic fish are resistant to irradiation-induced apoptosis. Eight-day-old RAG2-GFP (GM2) without irradiation (A) or two days post-irradiation treatment (B). Eight-day-old RAG2-EGFP-zBCL2 transgenic fish without irradiation (C) or two days post-irradiation treatment (D). Asterisk denotes auto-fluorescence of the swim bladder. Fish oriented with anterior to the left and dorsal to the top.
Figure 16:
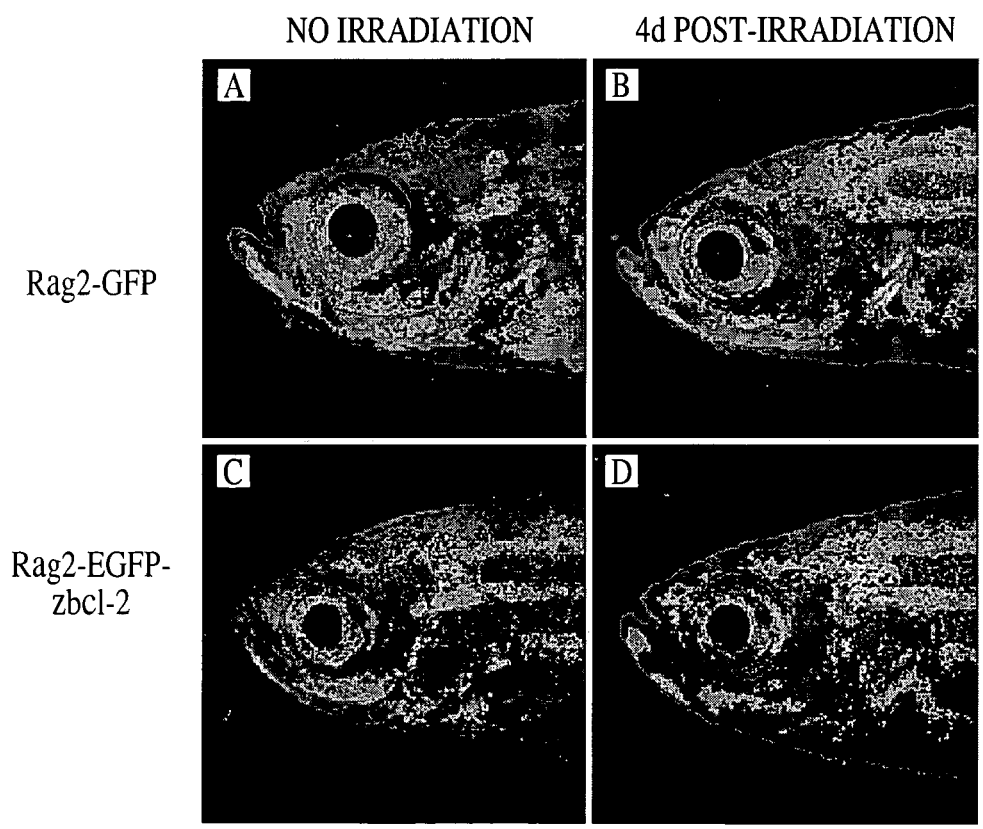
FIG. 16. T-cells from 3-month-old RAG2-EGFP-zBCL2 transgenic fish are resistant to irradiation-induced apoptosis. RAG2-GFP without irradiation (A) or four days post-irradiation treatment (B). RAG2-EGFP-zBCL2 transgenic fish without irradiation (C) or four days post-irradiation treatment (D). Fish oriented with anterior to the left and dorsal to the top.

T-cells from RAG2-EGFP-zBCL2 transgenic fish did not undergo apoptosis following treatment with ionizing radiation (15, 20, and 25 Gy), as determined by continued GFP expression in the thymus. In contrast, RAG2-GFP transgenic fish lost GFP-labeled T-cells 2 to 3 days post-irradiation treatment in both 8 day-old fish (FIG. 15) and 3 month-old fish (FIG. 16). The response to radiation was an "all or nothing" response. Thus, scoring the phenotypic changes marked by GFP-expression in the thymus an easy assay for apoptosis in the T-cells at 8 and 23 days of age, and in the T-cells at 3 months of age.

D. Developing a High-Throughput 96-Well Assay.

Next it was determined if 5- to 8-day old zebrafish embryos are able to survive in 96 well plates, and what concentration of water was necessary to attain high levels of survival. Six-day old zebrafish embryos were allocated to wells in a 96 well plate. Three to four embryos were grown in 250, 150, and 100 μl of egg water with and without 1% DMSO and analyzed daily for mortality.

E. A 96-Well Assay for Drug Treatment.

5- to 8-day old zebrafish embryos were able to survive in as little as 100 μl of egg water for up to 2 days post-treatment. However, significant mortality was seen in wells containing 100 μl of water at 3 days post-treatment. Fish were able to survive in 150 and 250 μl of water with a high rate of survival by 2 days of treatment. However, some death was seen wells containing 150 μl at 2 and 3 days. In contrast, fish survived in wells containing 250 μl at 3 days post-treatment. DMSO had no significant effect on embryo survival.

Thus, for treatment regimes requiring 2 days of analysis, 150 μl of egg water is sufficient for an assay volume. In contrast, for treatments regimes requiring 3 days of analysis, 250 μl of egg water is required.

F. RAG2-GFP Thymocyte Response to Dexamethasone.

In order to determine if 5 to 8 day old fish are able to absorb chemicals from the water, and if normal GFP-labeled T-cells are responsive to chemical ablation, we treated 5 day-old RAG2-GFP fish with varying doses of dexamethasone (DEX). Specifically, 6 GFP-positive RAG2-GFP embryos were arrayed into 6 well plates containing 5 ml of egg water. Wells contained either 0.1% ethanol (control), 250 μg/mL DEX (1% ethanol), 25 μg/mL DEX (0.1% ethanol), 12.5 μg/mL DEX (0.05% ethanol), 5 μg/mL DEX (0.02% ethanol), or 1 μg/mL DEX (0.004% ethanol). Fish were assessed for GFP expression in the thymus at 6, 7, and 8 dpf G. RAG2-GFP Thymocytes are Responsive to Chemical Ablation.

Figure 17:
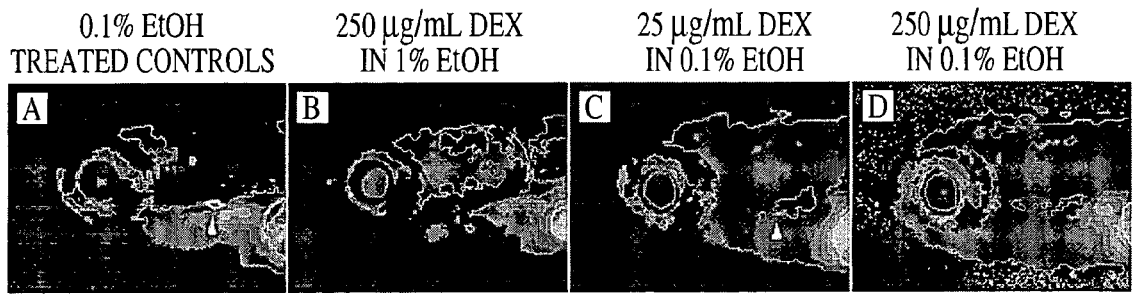
FIG. 17. T-cells from 5 day old RAG2-GFP fish are ablated by dexamethasone treatment by 8 dpf. RAG2-GFP control fish treated with 0.1% ethanol (A). RAG2-GFP fish treated with 250 milligrams/microliter (B) or 25 milligrams/microliter of dexamethasone (C,D). All 6 fish treated with 250 milligrams/microliter of dexamethasone lacked GFP-labeled T-cells by 8 dpf (3 days of treatment) while 2 of 6 fish treated with 25 milligrams/microliter of dexamethasone lacked GFP-labeled cells (D). Some fish in the 25 milligrams/microliter treatment group had significantly less T-cells than when compared to controls (C).

RAG2-GFP fish responded to DEX treatment (FIG. 17). Specifically, GFP-positive T-cells were not detected in RAG2-GFP embryos treated with 250 μg/mL of DEX at 3 days post-treatment (8 dpf). In contrast, GFP-labeled T-cells were present in fish treated with 0.1% ethanol. Partial responses were seen in DEX-treated fish receiving a 25 μg/mL dose, with 2 of 6 fish showing complete absence of T-cells and several having decreased T-cells in the thymus by 3 days post-treatment.

These results indicated that 5 to 8 day-old zebrafish embryos were able to absorb chemicals from the water, and the normal GFP-labeled T-cells were responsive to chemical ablation by DEX. Finally, these experiments highlight the use of transgenic fish for the development of drug based screens for immunosuppressive agents, and illustrate the ease of screening for chemical suppressors in the fish.

H. A Chemical Screen to Identify Drugs that Inhibit BCL2 Function.

Five-day-old RAG2-EGFP-zBCL2 transgenic zebrafish embryos will be irradiated and three fish arrayed per well into a 96 well plate. Each well will contain 150-250 microliters of egg water containing 8-10 chemical compounds. Fish will be analyzed for expression of GFP in the thymus at 2, and 3 days post-treatment as an indication of T-cell ablation due to apoptosis. Because T-cells in the RAG2-EGFP-zBCL2 transgenic line are insensitive to irradiation and because most drugs will have no affect on BCL2 function, thymocytes from transgenic fish will remain GFP labeled 2 days post-IR treatment. However, if a chemical is able to inhibit BCL2 function, T-cells will die and by 2 to 3 days post-treatment, thymocytes will be absent (as detected by GFP fluorescence). Drugs combinations that suppress BCL2 function will be tested individually on both RAG2-EGFP-zBCL2 and RAG2-GFP transgenic fish to (1) identify single compounds that inhibit BCL2 function, and (2) control for drugs that ablate T-cell function (i.e., compounds that kill T-cells independent of the transgenic line used).

I. A Dominant Genetic Screen to Identify Suppressors of BCL2 Function.

Our transgenic RAG2-EGFP-zBCL2 fish will also aid in the understanding of genetic programs that regulate apoptosis in T-cells in vivo. Specifically, a genetic modifier screen will be used to assess T-cell regression following irradiation treatment of 5 day-old embryos. Because GFP-positive T-cells in RAG2-EGFP-zBCL2 fish are resistant to irradiation-induced apoptosis, most fish screened will have GFP-positive T-cells following irradiation at 8 dpf. However, if a genetic modifier of BCL2 function is present in mutant fish, then GFP-positive T-cells will undergo apoptosis following irradiation and T-cells from these fish will be GFP-negative.

Figure 18:
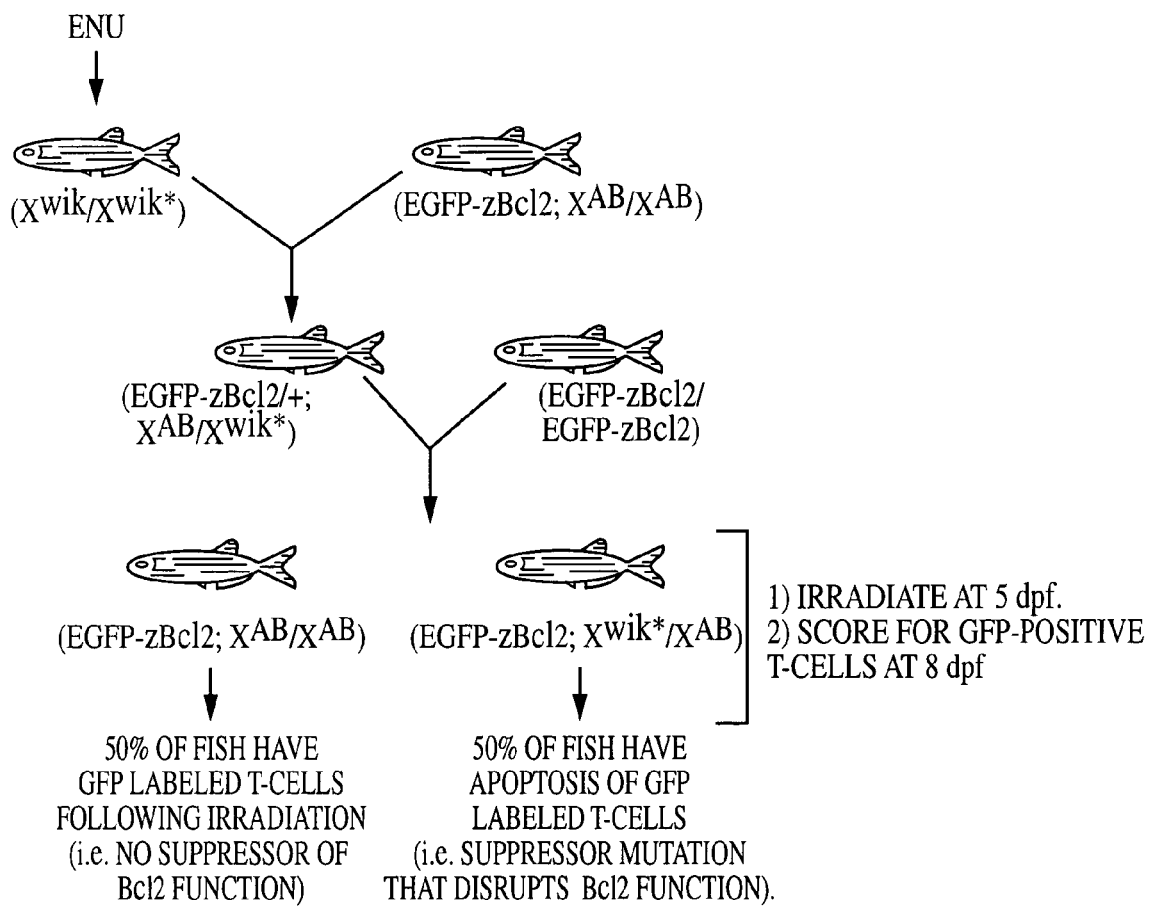
FIG. 18. Dominant genetic screen to identify suppressors of BCL2 function in RAG2-EGFP-zBCL2 fish. ENU induced point mutations in X gene are noted by asterisk and are linked to the Wik allele ($X^{Wik*}$) or wild-type X alleles in the AB strain are noted ($X^{AB}$). Five-day-old fish will be irradiated (15 Gy) and analyzed for loss of GFP-positive T-cells by 8 dpf.

For example, the following dominant modifier screen may be used to identify mutations that inhibit BCL2 function (FIG. 18). Wik male fish will be treated with Ethyl-nitrosourea (ENU) to induce point mutations in their sperm. On average, these ENU-treated males contain 100 point mutations per sperm. These males will be bred to AB strain RAG2-EGFP-zBCL2 fish. The resulting $F_1$ progeny will be heterozygous for both the RAG2-EGFP-zBCL2 transgene, and the mutation will be linked to the Wik allele. These $F_1$ fish will be bred to AB strain RAG2-EGFP-zBCL2 fish and the resulting $F_2$ progeny will be scored for sensitivity to irradiation. 5-day-old $F_2$ fish will be irradiated and assessed for T-cell regression on day 8, as determined by GFP expression in the thymus. Once $F_2$ mutant fish are identified, which lack GFP-positive T-cells in the thymus following irradiation, the $F_1$-founder fish will be bred to AB strain RAG2-EGFP-BCL2 fish, and the resulting progeny will be raised to adulthood. Because these fish carry a dominant mutant allele that is only activated by irradiation and acts by affecting BCL2 expressing cells, the heterozygous mutant fish will be viable. These $F_2$ fish will be used for mapping the mutation, with the dominant allele segregating with the Wik alleles.

Assuming approximately 40,000 genes in the zebrafish genome, the analysis of 400 $F_1$ mutagenized zebrafish should constitute one haploid genome equivalent. It will be necessary to analyze 3,000 $F_1$ fish, which should yield seven-fold coverage of the zebrafish genome.

J. A Recessive Genetic Screen to Identify Suppressors of BCL2 Function.

Figure 19:
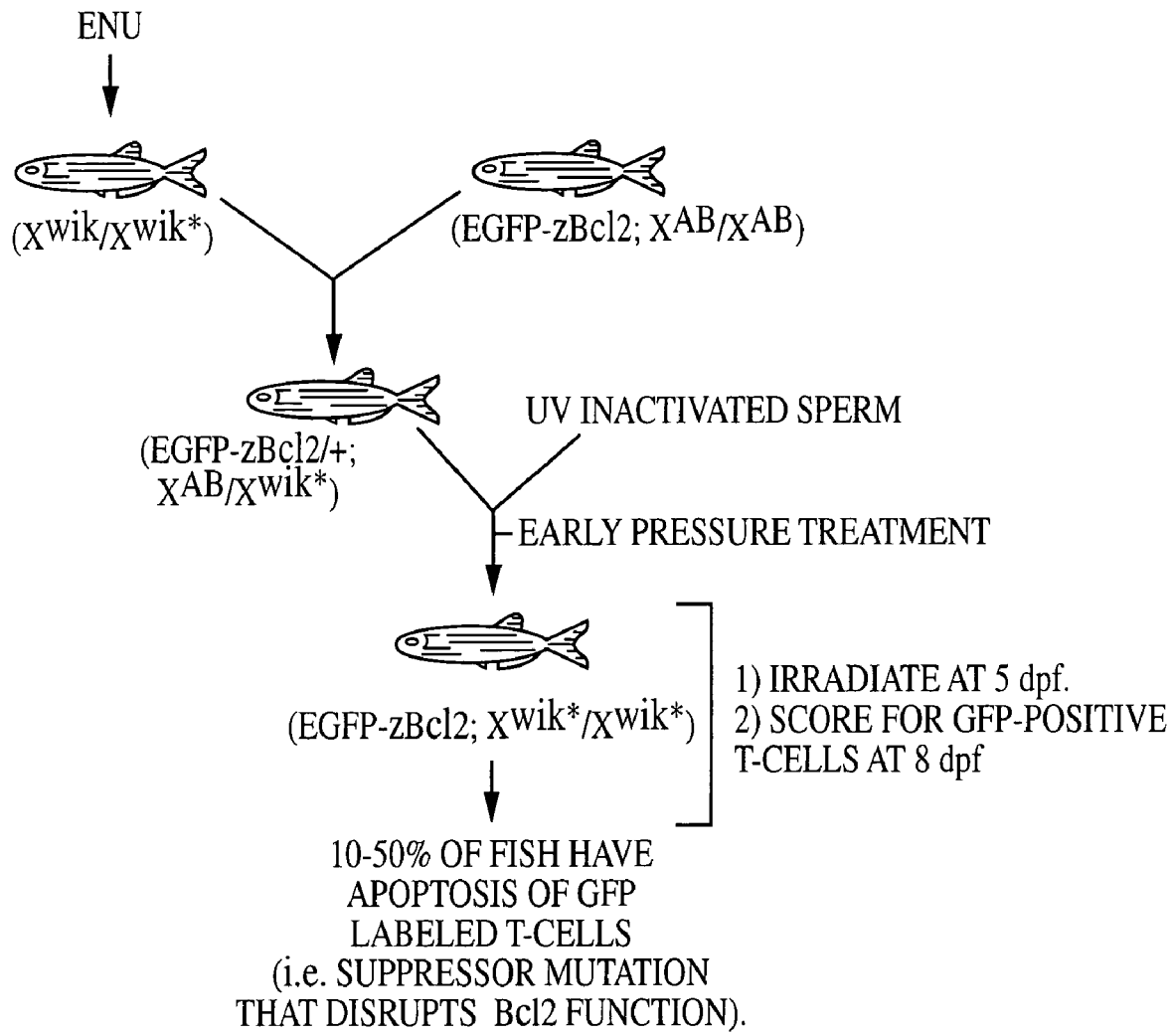
FIG. 19. Recessive genetic screen to identify suppressors of BCL2 function in RAG2-EGFP-zBCL2 fish. ENU induced point mutations in X gene are noted by asterisk and are linked to the Wik allele ($X^{Wik*}$) or wild-type X alleles in the AB strain are noted ($X^{AB}$). Five day old fish will be irradiated (15 Gy) and analyzed for loss of GFP-positive T-cells by 8 dpf.
Figure 20:
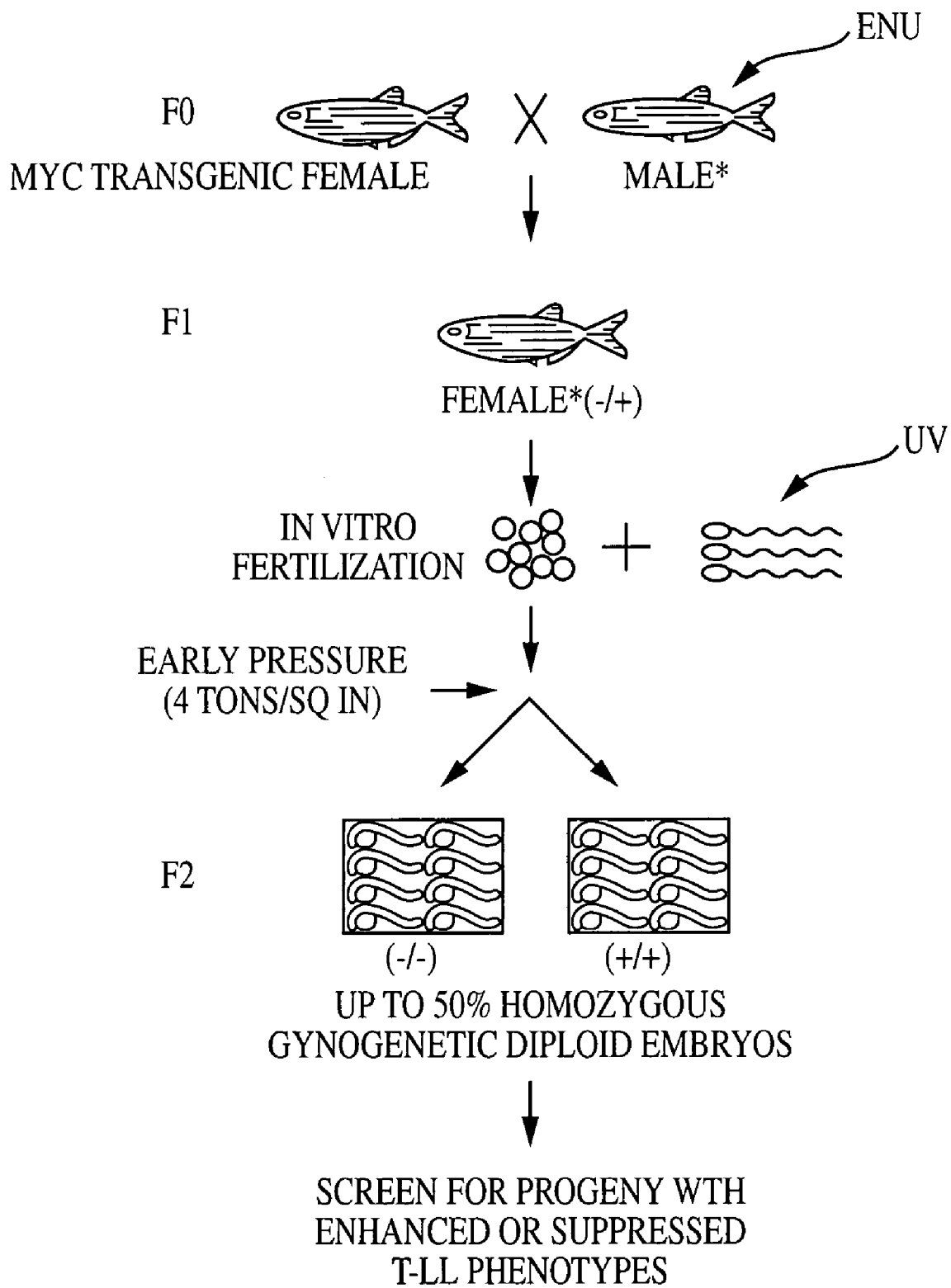
FIG. 20. Recessive genetic screen to identify suppressors or enhancers of MYC-induced leukemia. Adult zebrafish males are treated with ENU and mated to transgenic female fish which contain a conditional MYC allele targeted to T-cells by the RAG2 promoter. The eggs from the $F_1$ females obtained by squeezing and fertilized in vitro by UV-inactivated sperm and subject to early pressure. The resulting $F_2$ gynogenetic diploid embryos will the be induced to express the conditional EGFP-mMYC transgene, generating tumor prone fish. The larvae will be analyzed for variation in the onset of T-ALL.

Our model may also be used to identify recessive mutations that disrupt BCL2 function in T-cells following irradiation. For example, the following recessive modifier screen may be used to identify mutations that inhibit BCL2 function (FIG. 19). Wik male fish will be treated with ENU to induce point-mutations in their sperm. These males will be bred to AB strain RAG2-EGFP-zBCL2 fish. The resulting $F_1$ progeny will be heterozygous for the RAG2-EGFP-zBCL2 transgene, and the mutation will be linked to the Wik allele. Eggs harvested from individual $F_1$ females will be fertilized with UV-inactivated wild-type sperm. The UV-treatment crosslinks the sperm DNA, so that it will not contribute the genome of the developing zygote. A French press will be used to apply "early pressure" to zygotes within 90 seconds following fertilization, which will disrupt spindle formation during meiosis II and impair the segregation of homologous chromosomes. This will lead to gynogenetic diploid progeny, with 10% to 50% of the offspring being homozygous for mutated alleles. The resulting $F_2$ embryos will express the RAG2-EGFP-zBCL2 transgene and be homozygous for mutations. Five day-old $F_2$ fish will be irradiated and assessed for T-cell regression on day 8, as determined by GFP expression in the thymus. Once $F_2$ mutant fish are identified that lack GFP-positive T-cells in the thymus following irradiation, the $F_0$ founder fish will be bred to AB strain RAG2-EGFP-BCL2 fish, and the resulting progeny will be raised to adulthood. Because these fish carry a recessive mutant allele that is only activated by irradiation, and acts by affecting BCL2 expressing cells, the heterozygous mutant fish will be viable. These $F_2$ fish will be in-crossed to produce $F_3$ homozygous mutant fish that contain the RAG2-EGFP-zBCL2 transgene. The $F_3$ fish will then be used to map the mutation, with the phenotype (i.e. loss of GFP-labeled T-cells following irradiation) segregating mutations linked to the Wik alleles.

K. Discussion.

The zebrafish is a useful system for discovering new small molecule inhibitors of BCL2 or related family members because T-cell regression in transgenic RAG2-fish can be scored as an "all or nothing" response (see above) and because T-cells can be easily visualized in vivo. This model offers several advantages for drug screening when compared to cell line based screens. First, drugs are tested in vivo. Thus, toxicity and uptake into affected tissues are determined at the time of screening. Second, small molecule inhibitors are added to the water that the fish swim in, which may be used to identify compounds that are water soluble and orally available. Finally, genetic screens using this zebrafish line, in combination with the RAG2-EGFP-mMYC transgenic fish, will provide new insight into the pathways that transform T-cells, as well as identification of genetic enhancers and suppressors of BCL2.

EXAMPLE 3

Transgenic Models of High-Grade Astrocytoma

High-grade astrocytomas are the most common and devastating adult brain tumors, spreading so rapidly that patients seldom survive more than 9-12 months. Despite progress in surgical, radiation and chemotherapy technologies, there has been little improvement in the outcome of patients with astrocytoma over the last twenty years. Clearly, novel approaches are needed to better understand the biological basis of this disease before effective therapies can be developed.

The brain consists of two main types of cells, neurons and glia, which multiply and migrate in precise patterns during early development, resulting in the complex structures of the brain. As the brain develops in the embryo, the proliferation and migration of glia is controlled by the coordinated activity of many genes. While some genes are needed to begin normal glial cell proliferation and migration, others are necessary for appropriately stopping these processes. Astrocytomas are cancers specific to glia and in human tumor samples, a number of genes that normally function during glial cell development are consistently mutated. These mutations result in the loss of control of normal cell proliferation and lead to tumor formation. Genes that control cell proliferation during development, and keep it in check throughout life, are called tumor suppressors. In astrocytoma, mutated tumor suppressor genes include p53 (seen in 60-70% of all cases), and two genes in a region of human chromosome 10q (75-90% of all cases): PTEN and MXI1. Other genes are not mutated, but are inappropriately turned on in these tumors, such as the EGFR gene (50% of all cases). A combination of these genetic events is necessary to produce a malignant high-grade astrocytoma, adding to the complexity of the disease and its treatment.

Zebrafish are advantageously used to study astrocytoma because zebrafish brains form much like humans. Not only do the same genes, including those listed above, function during its development, but they can also develop brain tumors. The zebrafish offers many other advantages including: fecundity, each female laying 2-300 eggs/week, and transparent embryos that develop outside of the mother. This allows the direct observation of the rapidly developing brain, which is well formed by 48 hours. Zebrafish may be created which specifically misexpresses genes, such as EGFR, in glial cells by directing gene expression using a glial-specific promoter, such as, GFAP (glial fibrillary acidic protein). As was done for in the experiments outlined in Example 1, engineered fish that express green fluorescent protein in their glia could allow for the direct observation of the transformed glial cells in the transparent, living animal expressing the GFAP-EGFR transgene. Other genes and promoters may be used to develop new models of high-grade astrocytomas.

Astrocytoma transgenic fish lines may be used in additional mutagenesis and chemical studies to identify genes and other test drugs and agents that may suppress or modify the disease in these animals (as described more fully in Example 1). This information may then be used in the development of effective treatments for this disease.

EXAMPLE 4

Transgenic Models of Rhabdomyosarcomas

Rhabdomyosarcomas are a heterogeneous group of malignant tumors and are the most common soft-tissue sarcoma in children of 15 years or younger. Rhabdomyosarcoma consists of two histologic subtypes, alveolar and embryonal, each characterized by the misexpression of different subsets of genes. Alveolar rhabdomyosarcoma expresses members of the myogenic regulatory (MRF) family of transcription factors, normally found in developing skeletal muscle, and PAX3 and PAX7 genes, members of the Paired Box transcription factor family. In nearly all alveolar rhabdomyosarcoma cases, these PAX genes are found fused to the forkhead family member gene (FKHR) due to specific translocations, notably t(2;13)(q35;q14) comprising 95% of cases, and a variant, t(1;13)(p36;q14) in 5% of cases. The resulting fusion proteins are thought to activate downstream targets of PAX3 and PAX7, leading to cell transformation. These translocations are often accompanied by the over-expression of genes such as MYCN, MDM2, CDK4 and GLI1. The molecular basis of the embryonal subtype, the predominant form of rhabdomyosarcoma, remains unclear, but is thought to be characterized by loss of heterozygosity (LOH 11p15) and the disruption of other genes such as IGF2, ATR, ATM, PTEN, PTC, pRB, p16 and TP53.

The aggressive nature of these tumors makes their effective treatment particularly difficult. While rhabdomysarcomas can be observed in genetically-engineered, mammalian disease models, they are often associated with other tumor types. While informative, a more specific model of rhabdomyosarcoma is necessary to elucidate its molecular basis and to identify novel genes that may ultimately be used as targets for the development of novel therapeutic strategies.

Zebrafish develop soft-tissue tumors, both spontaneously and in response to embryonic exposure to mutagens and tissue specific promoters such as MyoD and alpha-actin have been identified, both of which drive strong expression of GFP in developing muscle.

The specific translocations that typify alveolar rhabdomyosarcoma result in the generation of PAX3-FKHR and PAX7-FKHR fusion proteins. Incorporating these fusion genes, and/or the other genes expressed in rhabdomyosarcoma such as MYCN, MDM2, CDK4 and GLI1, into the MyoD and alpha-actin promoter constructs will be useful as a model of rhabdomyosarcoma in the zebrafish.

Alternatively, the PAX3-FKHR and PAX7-FHKR genes may be fused with GFP in order to directly visualize transgene expression in vivo throughout early zebrafish development. The ability to directly visualize the transgene-GFP expression in vivo throughout zebrafish maturation will facilitate the identification and analysis of the tumorigenic phenotype.

Although a zebrafish disease model based upon the fusion proteins found in alveolar rhabdomyosarcoma-associated translocations is probably the most effective way to phenocopy rhabdomyosarcoma, it is possible that the expression of other genes known to be over-expressed in this disease may be necessary to observe tumorigenesis. Therefore, additional transgenic lines will be generated using the muscle-specific promoter constructs, such as those described herein, to drive the expression of individual oncogenes such as MYCN, MDM2, CDK4, GLI1 or a dominant negative form of p53, which have all been shown to be associated with rhabdomyosarcoma. Furthermore, once such transgenic lines are established, they may be tested for the ability to genetically interact with each other by intercrossing them and analyzing their phenotype for synergistic or complementing effects, as described in Example 1 and elsewhere herein.

The development of transgenic models of rhabdomyosarcoma, as well as other types of cancer, will be useful to exploit the forward genetics capacity of this vertebrate model system to identify genes that regulate rhabdomyosarcoma development. Once transgenic lines giving rise to the rhabdomyosarcoma phenotype are generated, they may be used as the basis for an ethyl-nitrosurea (ENU) mutagenesis screen, as described herein. Briefly, male transgenic fish may be treated with, e.g., ENU to induce point mutations in germ cells, and then mated with transgenic female fish, giving rise to $F_1$ progeny that are heterozygous for potential mutations. The eggs are collected from mature $F_1$ females, fertilized with UV-inactivated sperm and undergo 'early pressure'. This results in gynogenetic diploid animals with up to 50% of the offspring being homozygous for alleles carrying mutations that may result in an alteration in the rhabdomyosarcoma phenotype normally seen in the transgenic line. Once potential mutants are identified in the progeny of a particular $F_1$ female, she will be outcrossed to recover a line of heterozygous mutants. These fish may be incrossed and mutant homozygous progeny identified. The mutations may then be genetically mapped to specific linkage groups, such as by using a genome-wide scanning approach. Once a linkage group is determined, polymorphic markers flanking the mutated gene may be identified and other methods well known to those skilled in the art may be used to initiate positional cloning using the physical radiation hybrid map. This process will lead to cloning of the mutated gene by direct sequencing and candidate gene analysis. As in Example 1, numerous types of genetic screens may be designed including, but not limited to, dominant modifier screens, homozygous early pressure screen, or homozygous $F_3$ screens, which are well known to those of skill in the art. The mutagen may be, for example, ENU, EMS, or viral insertion.

The genes identified as a result of this zebrafish disease model represent potential regulators of the molecular-genetic pathway leading to rhabdomyosarcoma and may then be used to identify human homologs. Using this method, novel targets for drug design and developing improved therapies to treat this devastating disease may be determined. Similarly, chemical based screens may identify therapeutic agents that can suppress the phenotypes associated with overexpression of oncogenes in muscle cells. Such chemicals may then be candidates for clinical trials in human patients suffering from rhabdomyosarcoma.

EXAMPLE 5

Transgenic Models of Acute Myeloid Leukemia

The mutations and gene rearrangements commonly seen in acute myeloid leukemias typically result from a chromosomal translocations such as the t(8;21) or t(15;17), generate chimeric oncoproteins by fusing one or two transcription factors (Look, 1997). However, these alterations are not sufficient to explain the induction of acute leukemia. For example, expression of PML-RARα in murine myeloid cells causes leukemia only after a long pre-leukemic phase (He et al., *Proc Natl Acad Sci USA*, 94:5302-5307 (1997) and Grisolano et al., *Blood* 89:376-387 (1997)) indicating that other mutations must occur, particularly affecting pathways involved in apoptosis and cell cycle control. It is now known that activated FLT3 kinase mutations occur in a high percentage of APL patients, possibly providing a second transforming event. FLT3-activating mutations occur in approximately 25% of cases of AML, making them among the most frequent mutations linked to the molecular pathogenesis of human AML. These mutations are either internal tandem repeats (ITD) that occur in the juxtamembrane domain of the FLT3 receptor or point mutations in the negative regulatory loop domain of the kinase (Yamamoto et al., *Blood* 97:2193A (2001)) that causes constitutive activation of FLT3. Although in vitro cell lines and murine models are being developed to study FLT3 activation, the forward genetic capacity of the zebrafish system provides a unique advantage in that it permits the unbiased detection of mutations in many potentially novel genes that lead to leukemia. Recent studies have indicated that the spatio-temporal expression of zebrafish homologues of known mammalian myelopoietic genes and the morphologic and cytochemical features of zebrafish myelopoiesis are remarkably conserved (Bennett et al., *Blood* 98:643-651 (2001), Herbomel et al. *Development* 126:3735-3745 (1999), reviewed in Hsu et al., *Current Opinion in Hematol*, 81:245-251 (2001)).

Studies in the mouse indicate that overexpression of the FLT3-ITD mutated cDNA causes a myeloproliferative disorder (Kelly et al., *Blood*, 99:310-318 (2002)). Furthermore, studies of other tyrosine kinase oncogenes in the mouse, such as BCR/ABL, have demonstrated a lack of differentiation block, more active proliferation, and strong anti-apoptotic activity (Evans et al., *Cancer Res*, 53: 1735-1738, (1993); Laneuville et al., *Cancer Res.*, 54:1360-1366 (1994); Druker et al., *Nat Med*, 2: 561-566 (1996); and Carlesso et al., *Oncogene* 9: 149-156 (1994)). Numerous zebrafish promoters have been identified that drive strong expression of GFP in myeloid cells, as described herein, including the PU.1, MPO, or C/EBPα promoters. Utilizing stable lines of transgenic zebrafish expressing a constitutively activated FLT3, BCR/ABL, and PML-RARα allows for the study of acute myeloid leukemia in the zebrafish, with FLT3 overexpression in myeloid cells resulting in hypercellular kidney marrow, splenomegaly, and neutrophilia resembling a myeloproliferative disorder. Enhancer-suppressor screens, as described herein, will in identifying specific modifier genes that encode targets for the development of small molecule inhibitors that can be used as therapy for clonal myeloid neoplasias.

EXAMPLE 6

Conditional Models of Cancer

Many of the underlying mechanisms that lead to neuorendocrine carcinoma, pancreatic carcinoma, ovarian carcinoma, testicular carcinoma, stomach cancer, colon cancer, renal cancer, melanoma and acute or chronic myeloid leukemia have yet to be fully understood. Identifying the genes mutated in these diseases will lead to new insights into cancer as a whole. Additionally, using a vertebrate model system in which genetic or chemical suppressors can be identified that inhibit or delay disease progression will be necessary to identify new drug targets for the development of targeted chemotherapies.

As described in Example 1, conditional transgenic zebrafish lines may be produced using a CRE/Lox-mediated excision event to drive expression of the EGFP-mMYC transgene, and CRE-mediated recombination was shown to be active in zebrafish. However, use of a site-specific recombination strategy may be more broadly applicable to developing zebrafish models of a variety of other cancers, including but not limited to: neuorendocrine carcinoma, pancreatic carcinoma, ovarian carcinoma, testicular carcinoma, stomach cancer, colon cancer, renal cancer, melanoma and acute or chronic myeloid leukemia.

One strategy may be used to create stable transgenic fish models of cancer in which an oncogene is regulated in any tissue by using a regulatable site-specific recombinase. A transgenic fish whose genome has stably-integrated therein a transgene cassette comprising a Floxed, Loxed or FRTed reporter gene, such as a fluorescent protein gene (e.g., GFP, RFP, BFP, YFP, or dsRED2) or a luciferase gene, which comprises at strong stop-site, is regulated by a ubiquitous gene promoter (e.g., beta-actin or EF1-alpha), and a second transgene (e.g., an oncogene) placed immediately after the reporter gene. The second gene product is adjacent the reporter gene, but is not expressed in the absence of recombinase activity because of the strong transcription stop-site within the reporter gene. A second transgenic fish whose genome has stably integrated therein a flip (for use with FRT) or Cre-recombinase (for use with Flox or Lox) gene operably linked to a heat shock inducible promoter (e.g., HSP-70) is mated to the first transgenic fish. Cells within the offspring are then activated by heating with a laser, as described elsewhere herein. Once specific cells are heated with the laser, recombination is activated causing excision of the fluorescent protein gene and juxtaposition of the ubiquitous gene promoter adjacent to the oncogene. This results in the activation of the oncogene in specific cells and may be targeted to many different T-cell types.

Previous experiments have shown that the HSP-70 promoter is strictly regulatable in transgenic zebrafish by laser-activation of individual cells (Halloran et al., 2000) and that the HSP-70 promoter can drive expression of genes other than GFP in transgenic animals (Xiao et al., 2003). Individual cells can be identified easily because the fish is translucent in development. Additionally, the fish develop most organ systems by 5 dpf, and therefore, nearly all cell types can be targeted by laser-activation. Because this strategy relies on the generation of a transgenic fish in which oncogene activation can be targeted to any cell in the body (i.e., the use of a ubiquitous promoter driving expression of the reporter gene and the second oncogene), new models of cancer in the fish will be able to be developed, which do not require the generation of new transgenic lines with each cancer being studied.

For example, creation of transgenic zebrafish which expresses the loxed-dsRED allele adjacent the EGFP-mMYC transgene, which is regulated by the beta-actin promoter (β-actin-Lox-dsRED-Lox-EGFP-mMYC) may be useful for generating models to study pancreatic beta cell tumors, invasive islet adenocarcinoma, Burkitt's Lymphoma, Acute Myeloid Leukemia, colon carcinoma, glioblastomas, and melanoma all of which have activation of the MYC oncogene. Development of each of these models only requires activation of CRE within the cells that give rise to affected tissues, which is facilitated by laser activation described herein.

While the inventions have been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. In addition, all references cited herein are indicative of the level of skill in the art and are hereby incorporated by reference in their entirety.

What is claimed is:

1. A transgenic fish whose genome comprises a transgene encoding cMYC oncogene operably linked to a RAG2 promoter, wherein the oncogene is expressed in T-lymphocytes and induces T-cell acute lymphoblastic leukemia.

2. The transgenic fish of claim 1, wherein the cMYC oncogene is fused to a reporter gene.

3. The transgenic fish of claim 2, wherein the reporter gene is a fluorescent protein gene.

4. The transgenic fish of claim 3, wherein the fluorescent protein gene is GFP.

5. The transgenic fish of claim 1, wherein the cMYC oncogene is fused to ER.

6. The transgenic fish of claim 5, wherein the ER is tamoxifen-sensitive ER (ER™).

7. The transgenic fish of claim 1, wherein the transgenic fish is a transgenic zebrafish.

8. A method of screening test drugs or agents that suppress cMYC oncogene-induced leukemia, comprising:
   contacting or otherwise exposing a transgenic fish to a test drug or agent, wherein the transgenic fish has a genome that comprises a transgene encoding mouse cMYC oncogene operably linked to a RAG2 promoter, and wherein expression of the oncogene in T-lymphocytes induces T-cell acute lymphoblastic leukemia;
   comparing the leukemia in said transgenic fish after contact or exposure to said test drug or agent relative to the leukemia of said fish prior to contact or exposure with said test drug or agent;
   wherein suppression of the leukemia in said transgenic fish after contact or exposure to said test drug or agent relative to the leukemia of said fish prior to contact or exposure with said test drug or agent is indicative of a test drug or agent that suppresses cMYC-induced leukemia.

9. The method of claim 8, wherein the comparison step comprises measuring the rate of onset of tumor formation resulting from cMYC oncogene-induced leukemia.

10. The method of claim 8, wherein the comparison step comprises measuring the amount or size of tumors resulting from cMYC oncogene-induced leukemia.

11. The method of claim 8, wherein the test drug or agent is antisense DNA, antisense RNA, or small interfering RNA.

12. The method of claim 8, wherein the transgenic fish is a transgenic fish embryo.

13. The method of claim 8, wherein the transgenic fish is a transgenic zebrafish.

14. The method of claim 12, wherein the transgenic fish embryo is a transgenic zebrafish embryo.

* * * * *